(12) United States Patent
Centanni et al.

(10) Patent No.: US 8,092,531 B2
(45) Date of Patent: Jan. 10, 2012

(54) HUMAN SKIN EQUIVALENTS EXPRESSING EXOGENOUS POLYPEPTIDES

(75) Inventors: John M. Centanni, Madison, WI (US); B. Lynn Allen-Hoffmann, Madison, WI (US)

(73) Assignee: Stratatech Corporation, Madison, WI (US)

( * ) Notice: Subject to any disclaimer, the term of this patent is extended or adjusted under 35 U.S.C. 154(b) by 0 days.

(21) Appl. No.: 12/690,160

(22) Filed: Jan. 20, 2010

(65) Prior Publication Data

US 2010/0119495 A1 May 13, 2010

Related U.S. Application Data

(63) Continuation of application No. 10/909,119, filed on Jul. 30, 2004, now Pat. No. 7,674,291.

(60) Provisional application No. 60/491,869, filed on Aug. 1, 2003, provisional application No. 60/493,664, filed on Aug. 8, 2003.

(51) Int. Cl.
*A61F 2/10* (2006.01)
*A01N 1/00* (2006.01)
*A01N 63/00* (2006.01)
*C12N 15/63* (2006.01)
*C07H 21/04* (2006.01)

(52) U.S. Cl. .................. 623/15.12; 435/1.1; 435/320.1; 435/455; 424/93.21; 536/23.5

(58) Field of Classification Search .............. 424/93.21; 435/1.1, 320.1, 455; 536/23.5; 623/15.12
See application file for complete search history.

(56) References Cited

U.S. PATENT DOCUMENTS

| | | | |
|---|---|---|---|
| 4,485,096 A | 11/1984 | Bell | |
| 4,528,265 A | 7/1985 | Becker | |
| 5,536,656 A | 7/1996 | Kemp et al. | |
| 5,658,331 A | 8/1997 | Della Valle et al. | |
| 5,693,332 A | 12/1997 | Hansborough | |
| 5,968,546 A | 10/1999 | Baur et al. | |
| 5,989,837 A | 11/1999 | Hoffmann et al. | |
| 6,039,760 A | 3/2000 | Eisenberg | |
| 6,077,692 A | 6/2000 | Ruben et al. | |
| 6,214,567 B1 | 4/2001 | Hoffmann et al. | |
| 6,485,724 B2 | 11/2002 | Allen-Hoffmann | |
| 6,495,135 B2 | 12/2002 | Hoffmann | |
| 6,514,711 B2 | 2/2003 | Hoffmann | |
| 6,693,077 B1 | 2/2004 | Ruben et al. | |
| 6,846,675 B2 | 1/2005 | Conrad et al. | |
| 6,974,697 B2 | 12/2005 | Comer et al. | |
| 7,247,478 B2 | 7/2007 | Eberhardt et al. | |
| 7,452,864 B2 * | 11/2008 | Stahle-Backdahl et al. ... | 514/1.1 |

FOREIGN PATENT DOCUMENTS

| | | |
|---|---|---|
| WO | 00/72895 | 12/2000 |
| WO | WO 00/07895 A1 | 12/2000 |
| WO | 01/02433 | 1/2001 |
| WO | WO 01/02433 | 1/2001 |
| WO | 02/070729 | 9/2002 |
| WO | 2005/012492 | 10/2005 |
| WO | WO 2005/012492 A3 | 10/2005 |

OTHER PUBLICATIONS

Conrad et al., 2002, US 20020164793 A1.*
Rollman, Ola, et al.; "Platelet Derived Growth Factor (PDGF) Responsive Epidermis Formed from Human Keratinocytes Transduced with the PDGFB Receptor Gene"; Journal of Investigative Dermatology; May 2003; vol. 120, pp. 742-749.
Supp, Dorothy M., et al.; "Expression of human B-defensins HBD-1, HBD-2, and HBD-3 in cultured Keratinocytes and skin substitutes"; Burns (2004); vol. 30, pp. 643-648.
Erdag, Gulsun, et al.; "Allogeneic Versus Xenogeneic Immune Reaction to Bioengineered Skin Grafts"; Cell Transplantation (2004); vol. 13, pp. 701-712.
Pivarcsi, Andor, et al.; "Innate Immunity in the Skin: How Keratinocytes Fight Against Pathogens"; Current Immunology Reviews (2005); vol. 1, pp. 29-42.
Rudinger, J.; "Characteristics of the amino acids as components of a peptide hormone sequence"; Peptide Hormones, (1976) Parsons, University Park Press, Baltimore, US; pp. 1-7.
Kaye, Frederic J., et al.; "A single amino acid substitution results in a retinoblastoma protein defective in phosphorylation and oncoprotein binding"; Proc. Natl. Acad. Sci. USA (Sep. 1990); vol. 87, pp. 6922-6926.
Skolnick, Jeffrey, et al.; "From genes to protein structure and function: novel applications of computation approaches in the genomic era"; Trends in Biotech (Jan. 2000); vol. 18, pp. 34-39.
Chan, Teddy, et al; "Development, characterization, and wound healing of the keratin 14 promoted transforming growth factor-B1 transgenic mouse"; Wound Rep. Reg. (2002); vol. 10, pp. 177-187.
Ghazizadeh, S., et al.; "Durable and stratum-specific gene expression in epidermis"; Gene Therapy (2002); vol. 9, pp. 1278-1285.
Holden and Vogel, "A technical Fix for an Ethical Bind?" Science, 2004, 306: 2174-2176.
Cai et al., "Dedifferentiation: A New Approach in Stem Cell Research," 2007, BioScience, 57: 655-662.
Pera et al., "Human embryonic stem cells," 2000, Journal of Cell Science, 113: 5-10.
Merriam-Webster Medical Dictionary'[online], 2008 [retrieved on Feb. 4, 2008]. Retrieved from the Internet:< URL: http://www2.merriam-webster.com/cgi-bin/mwmednlm?book=Medical&va=multipotent> (1 PG).
Hinsenkam et al., "Effects of Low Frequency Pulsed Electrical Current on Keratinocytes in Vitro," 1997, Bioelectromagnetics, 18: 250-254.
Zuk et al., "Multilineage Cells from Human Adipose Tissue: Implications for Cell-Based Therapies," 2001, Tissue Engineering, 7: 211-228.
Pittenger et al., "Multilineage Potential of Adult Human Mesenchymal Stem Cells," 1999, Science, 284: 143-14.

(Continued)

*Primary Examiner* — Shin-Lin Chen
(74) *Attorney, Agent, or Firm* — Casimir Jones SC

(57) ABSTRACT

The present invention relates generally to compositions for wound closure. More specifically, the present invention provides human skin equivalents engineered to express exogenous polypeptides (e.g., antimicrobial polypeptides and keratinocyte growth factor 2) and compositions and methods for making human skin equivalents engineered to express exogenous polypeptides. In addition, the present invention provides methods for treatment of wounds with human skin equivalents engineered to express exogenous polypeptides.

5 Claims, 22 Drawing Sheets

OTHER PUBLICATIONS

Kobayashi et al., "Formation of Mast Cell Colonies in Methylcellulose my Mouse Peritoneal Cells and Differentiation of these Cloned Cells in Both the Skin and the Gastric Mucosa of W/W Mice: Evidence that a Common Precursor can give rise to both "Connective Tissue-Type" and "Mucosal" Mast Cells" 1986, The Journal of Immunology, 136: 1378-1384.

Barrandon and Green, "Three clonal types of keratinocyte with different capacities for multiplication," 1987, PNAS, USA, 84: 2302-2306.

Allen-Hoffmann et al "Normal Growth and Differentiation in a Spontaneously Immortalized Near-Diploid Human Keratinocyte Cell Line NIKS," Journal of Investigative Dermatology, 2000, vol. 114, pp. 444-455.

Carroll et al, Tissue and Stratum Specific Expression of the Human Involucrin Promoter in Transgenic Mice, Nov. 1993, vol. 90, pp. 10270-10274.

Myers et al, "Transplantation of Keratinocytes in the Treatment of Wounds," A. J. Surg. (1995) 170(1) 75-83.

Leask et al, "Regulation of a human epidermal keratin gene: sequences and nuclear factors Involved in keratinocyte-specific transcription" Genes Dev (1990) 4(11) 1985-1998.

Oren A., et al, "In human epidermis, B-defensin 2 is packaged in lamellar bodies," Exp Mol Pathol, 2003, 74(2) p. 180-2.

Gala, et al., J. Invest. Dermatol. (2001), vol. 117, p. 456 (Abstract).

Jimenez, Pablo A., et al.; "Keratinocyte Growth Factor-2 Accelerates Wound Healing in Incisional Wounds"; Journal of Surgical Research (1999), vol. 81, pp. 238-242.

Kopp, J., et al., "Healing of superficial second degree burn wounds is accelerated by stably in vitro KGF-transfected HaCat6 keratinocytes: Experimental studies in pigs"; European Tissue Repair Society (Online) 2001 & Tenth Annual Meeting of the European Tissue Repair Society; Brussels, Belgium, May 24-27, 2000, retrieved from the Internet, URL: http:/www.etrs.org/bulletin7_2/prize/page2.html; Abstract only (2 pgs.).

Munz, Barbara, et al.; Overexpression of activin A in the skin of transgenic mice reveals new activities of activin in epidermal morphogenesis, dermal fibrosis and wound repair; The EMBO Journal (1999); vol. 18, No. 19, pp. 5205-5215.

Schlegal, Richard, et al.; "Quantitative keratinocyte assay detects two biological activities of human papillomavirus DNA and identifies viral types associated with cerical carcinoma"; The EMBO Journal (1988); vol. 7, No. 10, pp. 3181-3187.

Liu, Xuedong, et al.; "Transforming growth factor B-induced phosphorylation of Smad3 is required for growth inhibition and transcription induction in epithelial cells"; Proc. Natl. Acad. Sci. (1997); Vo. 94, pp. 10669-10674.

Crish, James F.; "The Distal Regulatory Region of the Human Involucrin Promoter is Required for Expression in Epidermis"; The Journal of Biological Chemistry (Nov. 13, 1998); vol. 273, No. 46, pp. 30460-30465.

Okrent, Derek, G., et al.; Direct Cytotoxicity of Polymorphonuclear Leukocyte Granule Proteins to the Human Lung-derived Cells and Endothelial Cells; Am. Rev. Respir (1990); vol. 141, pp. 179-185.

Abiko, et al., 2003, "Upregulated expression of human beta defensin-1 and −3 mRNA during differentiation of keratinocyte immortalized cell lines, HaCaT and PHK16-0b," J Dermatol Sci, 31(3): 225-8.

Allen-Hoffmann et al., 2000, "Normal Growth and Differentiation in a Spontaneously Immortalized Near-Diploid Human Keratinocyte Cell Line NIKS," J Invest Dermatol, 114:444-455.

Asbill et al.,2000, "Evaluation of a human bio-engineered skin equivalent for drug permeation studies," Pharm. Res. 17(9): 1092-97.

Auger et al., 2000, "Multistep production of bioengineered skin substitutes: sequential modulation of culture conditions," In Vitro Cell. Dey. Biol. Animal 36:96-103.

Baden et al, 1987, "Isolation and characterization of a spontaneously arising long-lived line of human keratinocytes (NM 1)," In Vitro Cell. Dev. Biol. 23(3):205-213.

Barrandon and Green, 1987, "Three clonal types of keratinocyte with different capacities for multiplication," PNAS, USA, 84: 2302-2306.

Bensch, K.W., et al., 1995, "hBD-1: a novel beta-defensin from human plasma," FEBS Lett, 368(2): 331-5.

Boman, H.G., 1995, "Peptide antibiotics and their role in innate immunity," Annu Rev Immunol, 13: 61-92.

Boukamp et al., 1988, "Normal keratinization in a spontaneously immortalized aneuploid human keratinocyte cell line," J. Cell. Biol. 106:761-771.

Cal et al., 2007, "Dedifferentiation: A New Approach in Stem Cell Research", BioScience, 57: 655-662.

Carroll et al, 1993, "Tissue and Stratum Specific Expression of the Human Involucrin Promoter in Transgenic Mice," PNAS USA, 90:10270-10274.

Chan et al., Development, Chanracterizationm and Wound Healing of the Keratin 14 Promoted transforming Growth Factor-Betal Transgenic Mouse, Wounds Reg Reg. 2002, Wound Rep. Reg., 10:177-187.

Crish, 1998, "The Distal Regulatory Region of the Human Involucrin Promoter is Required for Expression in Epidermis"; The Journal of Biological Chemistry vol. 273, No. 46, pp. 30460-30465.

Erdag et al. 2004, "Allogeneic versus xenogeneic immune reaction to bioengineered skin grafts", Cell Transplantation, 13:701-712.

Frye et al., 2001, "Expression of human beta-defensin-1 promotes differentiation of keratinocytes," J Mol Med, 2001. 79(5-6): 275-82.

Ganz and Weiss, 1997, "Antimicrobial peptides of phagocytes and epithelia," Semin Hematol, 34(4): p. 343-54.

Garcia, et al, 2001, "Identification of a novel, multifunctional beta-defensin (human beta-defensin 3) with specific antimicrobial activity. Its interaction with plasma membranes of Xenopus oocytes and the induction of macrophage chemoattraction," Cell Tissue Res,306(2): 257-64.

Ghazizadeh et al., 2002, "Durable and stratum-specific gene expression in epidermis", Gene Therapy, vol. 9, p. 1278-1285.

Hancock, 1997, "Peptide Antibiotics," Lancet, 349(9049): p. 418-22.

Harder, et al., 1997, "A peptide antibiotic from human skin," Nature, 1997.387(6636): 861.

Harder, et al., 1997, "Mapping of the gene encoding human beta-defensin-2 (DEFB2) to chromosome region 8p22-p23.1," Genomics, 46(3): p. 472-5.

Harder, et al., 2000, "Mucoid *Pseudomonas aeruginosa*, TNF-alpha, and IL-1beta, but not IL-6, induce human beta-defensin-2 in respiratory epithelia," Am J Respir Cell Mol Bioi,22(6): 714-21.

Hinsenkamp et al., 1997, "Effects of low frequency pulsed electrical current on keratinocytes in vitro," Bioelectromagnetics, 18: 250-254.

Holden and Vogel, 2004, "Cell biology. A technical fix for an ethical bind?" Science, 306: 2174-2176.

Hoover et al., 2003, "Antimicrobial characterization of human beta-defensin 3 derivatives," Antimicrob Agents Chemother, 47:2804-2809.

Jimenez et al.; "Keratinocyte Growth Factor-2 Accelerates Wound Healing in Incisional Wounds"; Journal of Surgical Research (1999), vol. 81, pp. 238-242.

Kaye et al., 1990, "A single amino acid substitution results in a retinoblastoma protein defective in phosphorylation and oncoprotein binding", Proc. Natl. Acad. Sci. USA, vol. 87, pp. 6922-6926.

Kobayashi et al., 1986, "Formation of mast cell colonies in methylcellulose by mouse peritoneal cells and differentiation of these cloned cells in both the skin and the gastric mucosa of W/Wv mice: evidence that a common precursor can give rise to both "connective tissue-type" and "mucosal" mast cells," J Immunol, 136: 1378-1384.

Kopp et al., "Healing of superficial second degree burn wounds is accelerated by stably in vitro KGF-transfected HaCat6 keratinocytes: Experimental studies in pigs"; European Tissue Repair Society (Online) 2001 & Tenth Annual Meeting of The European Tissue Repair Society; Brussels, Belgium, May 24-27, 2000, retrieved from the Internet, URL: http:/www.etrs.org/bulletin7_2/prize/page2.html; Abstract only (2 pgs.).

Lichtenstein, A, et al., 1986, "In vitro tumor cell cytolysis mediated by peptide defensins of human and rabbit granulocytes," Blood, 1986.68(6): p. 1407-10.

Liu et al, 1997, "Transforming growth factor beta-induced phosphorylation of Smad3 is required for growth inhibition and transcriptional induction in epithelial cells," PNAS, USA, 94: 10669-10674.

Liu et al., 2002, "Human beta-defensin-2 production in keratinocytes is regulated by interleukin-1, bacteria, and the state of differentiation," J Invest Dermatol, 118(2): 275-81.

Luterman et al., 1986, "Infections in burn patients," Am J Med, 1986. 81(IA): 45-52.

Meana et al., 1998. "Large surface of cultured human epithelium obtained on a dermal matrix based on live fibroblast-containing fibrin gels," Burns 24:621-30.

Merriam-Webster Medical Dictionary [online], 2008 [retrieved on Feb. 4, 2004]. Retrieved from the Internet<URL: http://www2.merriam-webster.com/cgi-bin/mwmednlm?book=Medical&va=pluripotent>, p. 1.

Merriam-Webster Medical Dictionary'[online], 2008 [retrieved on Feb. 4, 2008]. Retrieved from the Internet< URL: http://www2.merriam-webster.com/cgi-bin/mwmednlm?book=Medical&va=multipotent>, p. 1.

Merriam-Webster's Medication Dictionary. Merriam-Webster, Inc. [online]. 2002 [retrieved on Jun. 22, 2007]. Retrieved from the Internet: URL:http://dictionary.reference.com/cite.html?qh=electroporation&ia=mwmed,pp. 1-3.

Milner and Ortega, 1999, "Reduced antimicrobial peptide expression in human burn wounds," Burns, 25(5): 411-3.

Munz et al, 1999, "Overexpression of activin A in the skin of transgenic mice reveals new activities of activin in epidermal morphogenesis, dermal fibrosis and wound repair," EMBO J, 18: 5205-5215.

Okrent et al.; 1990 Direct Cytotoxicity of Polymorphonuclear Leukocyte Granule Proteins to the Human Lung-derived Cells and Endothelial Cells; Am. Rev. Respir. (); vol. 141, pp. 179-185.

Pardi, A, et al, 1992, "NMR studies of defensin antimicrobial peptides. 2. Three-dimensional structures of rabbit NP-2 and human HNP-1," Biochemistry, 1992.31(46): p. 11357-64.

Pera et al., 2000, "Human embryonic stem cells," J Cell Sci, 113: 5-10.

Pittenger et al., 1999, "Multilineage potential of adult human mesenchymal stem cells," Science, 284: 143-147.

Pivarsci et al., 2005, Current Immunology Reviews, ,1(1): 29-42.

Rollman et al., May 2003, Journal of Investigative Dermatology, vol. 120, p. 742-749.

Rudinger, 1976, Peptide Hormones, Parsons, University Park Press, Baltimore, p. 1-7.

Schibli, OJ., et al, 2002, "The solution structures of the human beta-defensins lead to a better understanding of the potent bactericidal activity of HBD3 against *Staphylococcus aureus*," J Biol Chem,277(10): 8279-89.

Schlegel et al, 1988, "Quantitative keratinocyte assay detects two biological activities of human papillomavirus DNA and identifies viral types associated with cervical carcinoma," EMBO J, vol. 7, No. 10, pp. 3181-3187.

Schroder, 1999, "Epithelial peptide antibiotics," Biochem Pharmacol, 57(2):121-34.

Skolnick et al., 2000, "From genes to protein structure and function: novel applications of computational approaches in the genomic era", Trends in Biotech, vol. 18, p. 34-39.

Soler et al., 1999, "In vivo characterization of keratinocyte growth factor-2 as a potential wound healing agent," Wound Repair Regen. 7(3): 172-178.

Supp et al, 2004, "Expression of human beta-defensins HBD-1, HBD-2, and HBD-3 in cultured keratinocytes and skin substitutes", Burns, 30: 643-648.

Yang, et al.,1999, "Beta-defensins: linking innate and adaptive immunity through dendritic and T cell CCR6," Science, 286(5439): 525-8.

Zimmermann, G.R, et al., 1995, "Solution structure of bovine neutrophil beta-defensin-12: the peptide fold of the beta-defensins is identical to that of the classical defensins," Biochemistry, 34(41): 13663-71.

Zuk et al., 2001, "Multilineage cells from human adipose tissue: implications for cell-based therapies," Tissue Eng, 7: 211-228.

* cited by examiner

Figure 1a

AAGCTTATATTCCATGCTAGGGTTCTGGTGTTGGTGCGTGGGGTTGGGGTGGGACTGCA
GAATTCGCCCTTAAGATTATATTCCATGCTAGGGTTCTGGTGTTGGTGCGTGGGGTTG
GGGTGGGACTGCAGAAGTGCCTTTTAAGATTATGTGATTGACTGATCTGTCATTGGTTC
CCTGCCATCTTTATCTTTTGGATTCCCCTCGGAGGAGGGGAGGAAGGAGTTTCTTTTG
GGTTTTATTGAATGAAATGAAAGGGAAAGTAGAGCTGTTCCTATGTCCCGGGCTCCGGA
GCTTCTATTCCTGATCCCTGCATAAGAAGGAGACATGGTGGTGGTGGTGGTGGGTGGGG
GTGGTGGGGCACAGAGGAAGCCGGTACTGGGCTCTGCACCCCATTCCCGCTCCCAGATC
CCTCTGGACACAGCATTTTCTCCAGTGAGCACAGCCTCCCCTTGCCCCACAGCCAAC
AGCAACATGCCTCCCAACAAAAGCATCTGTCCCTCAGCCAAAACCCCTGTTGCCTCTC
TCTGGGAAATTGTAGGGCTGGGCCAGGGTGGGGGACCATTCTCTGCAGGGAGATTAG
GAGTGTCTGTCAGGGGCGGGTGGAGCGGGGTGGGCCCTGGCTTACTCACATCCTTGAG
AGTCCTTTGCTGGCAGATTTGGGGAGCCCACAGCTCAGATGTCTGTCTCAGCATTGTCT
TCCAAGCTCCTAGGCCACAGTAGTGGGGGGCTCCCTTCTCTGGCTTCTTCTTTGGTGAC
AGTCAAGGTGGGGTTGGGGGTGACAGAGGGTCCTGCTTCTGTACTAGGAGCAGTTGATC
CCAGGAAGAGCATCGGAGCCTCCAGCAGGGGCTGTTGGGGCCTGTCTGAGGAGATAGGA
TGCGTCAGGCAGCCCCAGACACGTTCACATTCCTCTCAACATGCCTGCCGGGGTCTGTG
GAGCCTAGGGGCTGATGGGAGGGTGGGGTGGGGCCGGAAGGGTTTGCTTCGGGAGGTT
GTCTGGGAGATTGCTGAAGTTTTGATATACACACCTCCAAAGCAGGACCAAGTGGACTC
CTAGAAATGTCCCCTGACCCTTGGGGCTTCAGGAGTCAGGGACCCTCGTGTCCACCTCA
CCTTGCCCTTGGCACAGCCCAGCTCCACTCCAGCCTCTACTCCTCCCAGAACATCTCC
TGGGCCAGTTCCACAAGGGGCTCAAACGAGGGCGCCTGAGCTGCCACACTAGGGATGTT
CTGGGGGTCTGAGAAGATATCTGGGCTGGAAGAATAAAAGGCCCCCTAGGCCTGTTCC
TGGATGCAGCTCCAGCCACTTTGGGGCTAAGCCTGGGCTATAACAATGCCAACGAGGCT
TCTTGCCATACTCGGTTTACAAAACCCTTTCACATACATTGTCGCATTGGATTCTCAGA
GCTGACTGCACTAAGCAGAATAGATGGTATGACTCCCACTTTGCAGATGAGAACACTGA
GGCTCAGAGAAGTGCCAAGCCCTGGGTCACAGAGGCGTAAATGGCAGAGCCAGGACCCA
CCTGACTCCAGGCTGGTTCCTGGCCTCCATGAGGCCACCTGCCCTATGGTGTGGTTGAT
GTGAGATCCTCACCATAGGGAGGAGATTAGGGTCTGTGCTCAGGGATGGGGAGGGCTTG
CTGGATTTCTCTTTGATGGGGATGTTGGGGTGGGAATCACGATACACCTGACTAGCTGG
GTGTATTTCAGGGATGGGACAGACTTCTCAGCACAGCATGGGAGGTCAGGCCTGGGAGG

Figure 1b

GCCCCCCAGACCTCCTTGTCTCTAATAGAGGGTCATGGTGAGGGAGGCCTGTCTGTGCC
CAAGGTGACCTTGCCATGCCGGTGCTTTCCAGCCGGGTATCCATCCCCTGCAGCAGCAG
GCTTCCTCTACGTGGATGTTAAAGGCCCATTCAGTTCATGGAGAGCTAGCAGGTAACTA
GGTTTAAGGTGCAGAGGCCCTGCTCTCTGTCACCCTGGCTAAGCCCAGTGCGCGGGTTC
CTGAGGGCTGGGACTCCCAGGGTCCGATGGGAAAGTGTAGCCTGCAGGCCCACACCTCC
CCCTGTGAATCACGCCTGGCGGGACAAGGAAGCCCAAAACACTCCAAACAATGAGTTTC
CAGTAAAATATGACAGACATGATGAGGCGGATGAGAGGAGGGACCTGGCTGGGAGTTGG
CGCTAGCCTGTGGGTGATGAAAGCCAAGGGGAATGGAAAGTGCCAGACCCGCCCCCTAC
CCACGAGTATAAAGCACTCGCATCCCTTTCCAATTTACCCGAGCACCTTCTCTTCACTC
AGCCAACTGCTCGCTCGCTCACCTCCCTCCTCTGCACCAADGGCGAAT

K14 Promoter Luciferase Vector Construction:

Mammalian Expression Vector Design:

Mammalian Expression Construct:

Figure 6

Sequence for Human Beta Defensin 1

```
  1  gtcagctcag cctccaaagg agccagcctc tccccagttc ctgaaatcct gagtgttgcc
 61  tgccagtcgc catgagaact tcctaccttc tgctgtttac tctctgctta cttttgtctg
121  agatggcctc aggtggtaac tttctcacag gccttggcca cagatctgat cattacaatt
181  gcgtcagcag tggagggcaa tgtctctatt ctgcctgccc gatctttacc aaaattcaag
241  gcacctgtta cagagggaag gccaagtgct gcaagtgagc tgggagtgac cagaagaaat
301  gacgcagaag tgaaatgaac tt
```

Figure 7

Sequence for Human Beta Defensin 2

```
  1  ggtgaagctc ccagccatca gccatgaggg tcttgtatct cctcttctcg ttcctcttca
 61  tattcctgat gcctcttcca ggtgtttttg gtggtatagg cgatcctgtt acctgcctta
121  agagtggagc catatgtcat ccagtctttt gccctagaag gtataaacaa attggcacct
181  gtggtctccc tggaacaaaa tgctgcaaaa agccatgagg aggccaagaa gctgctgtgg
241  ctgatgcgga ttcagaaagg gctccctcat cagagacgtg cgacatgtaa accaaattaa
                 301 actatggtgt ccaaagata
```

Figure 8

Sequence for Human Beta Defensin 3

```
1    catccagtct cagcgtgggg tgaagcctag cagctatgag gatccattat cttctgtttg 61   ctttgctctt cctgtttttg gtgcctgttc caggtcatgg aggaatcata aacacattac 121  agaaatatta ttgcagagtc agaggcggcc ggtgtgctgt gctcagctgc cttccaaagg 181  aggaacagat cggcaagtgc tcgacgcgtg gccgaaaatg ctgccgaaga aagaaataaa 241 aaccctgaaa catgacgaga gtgttg
```

Figure 9

Hu Involucrin Promoter sequence- Oligonucleotides used to amplify the promoter sequence are underlined.

```
aagcttct ccatgtgtcatgggatatga gctcatcctt attatgttgg gtggggttgga
cagttacc cagacttgtcatgtggacct ggagcttatg aggtcattca cataggcagtga
aagaacct ctcccatatacgtaatgcc tgtctcccaa atggggcaac ctgtgggcagaa
taagggac ttctcagccctagaatgttg aggtttcccc aacccctccc ttgcatacacac
acacacaa acactccctcagctgtatcc actgcctct ttcccacacc ctagctttgccc
agcagtca aaggctcacacataccatct tctccttaag gctcttatta tgccgtgagtca
gagggcgg gaggcagatctggcagatac tgagccctg ctaacccata agaccggtgtga
cttccttg atctgagtctgctgcccag actgactgtc acgggctggg aagaggcagatt
cccccag atgaagtcagcagcagagca caagggcatc agcgccaaag taaggatgcttg
attagttc ttcagggcagagtgggctgt gcttcctctg ccccagaaaa tggcacagtccc
tgttctat gggaaaaagaatgtgaggtc cctgggtggg ctcagggaac agagaggtcatg
aggagggg atagcactgcagaaaccaag ggtgccttgt gagtcctccc tctgtcttttta
ggcatgat ccaggaacatgacaaaatta gtgctttaaa tagatttact tggggctaagag
aaatgtgc ctgtcaggaaaactatgggg aatcaggaca cttctcaaaa ttagccccactg
agtattgt ctttataattccttctttt ggattagatt gtaaaaaga gagtgtaaatga
atgatgtc catataatgttattagcc aaccattaaa agaaaggga agaaataaatca
gtttggtt tttacacacatacagaca cacacatata aacattgatc aacactgaaatg
tttaatag tcattatttcgggtcgtaa aattcactgt tcttcaatga atacttgtagag
cacatatt atatgcagtagttttgatag gttctagggg tatagtggaa aacataccaggt
atacgctg ctcttagcttattttccagt gggaaagata gacaataagc aagtgaacaaat
gcaaataa attactctagattgttataa gtgaaattaa gtaccaatcc tttagatatggt
acacagag aaggatctctgacagacccc aacattgaca ctgaagctga aaggcataaaag
aaccagag acctggggaggggccggtgg gcagaaggag agcaggtgcc aagcccccaggt
ggagagct ctgggctcatctcaggaacc gaaggcctc agtgaggtaa gaatatacctct
cagggaga gattgacatgaattggggcc ccagaagaag gcagaagcca ggtacccagggt
cttttaaa ccacggcagtgagtttgaat gttatttcaa gtgtgctggt gcactgttggca
cggggag agatgtgctcaaatccccac tctgaaagat ttcttaagct atttctagagta
tgatttac aacaggaaatggatgatttg attctgatct ttataccttc atgcatttaaaa
aagtactt aagaaagtagtttggtttgt cattataaaa agcaatactt attttttatattg
tgtagatt caatcttgtttccttgccta gagtgggccg tgctttggag ttcttatgagca
tggcattc ctgagaacttctctaactgc agcctcgggc atagaggctg ggcagcaagtgg
cagcagca gaggactcctagaagccttc tacttgactc tacttggcct aaagtcaaactc
cctccacc aaagacagagtttatttcca cataggatgg agttaaaaaa tatattctgaga
gaggaagg gcttgtgcccaagagaaca ccccagaaat accacccctt catgggaagtga
ctctatct tcaaacatataacccagcct ggacatcccc gaaagacaca taactttccatt
tcatgccc ttgaaagtgaatcttttggc ctaataatga aacaaactc attttgaaagtg
gaaaaatt gagattcagagcagaagttt gactaaggtc acaaaacagt aggatgcctcac
tcagctcc ctgtgcctaggtcagaaaag catcacagga atagttgagc taccagaatcct
ctggccag gcaggagctgtgtgtccctg ggaaatgggg ccctaaaggg tttgctgcttaa
gatgcctg tggtgagtcaggaagggggtt agaggaagtt gaccaactag agtggtgaaacc
tgtccatcaccttcaacctggagggagg ccaggctgca gaatgatata aagagtgccctga
ctcctgctcagctcagcactccaccaaagcctctgcctcagccttactgtgagtctggtaagtg
tcggatggtagaaccagggttgg gactcgggac ctccaacagc atacgatgtg gtgggggg
tgg gcagctgggtgggggtggg cattactctg gggctggatt cagctggact ttcatt
ctag ggggactcgagtcagagtac tgagagaaaa gtgccttggc acagaagtgc agaac
agaga gtaatcatcctatgtcccat cttttcttgt gaccatattt ttggatttgtgtgtg
agaga gaattatggaagggaggagg ggaatagcat tcaacttctt tcctaaacct cttg
ggtttt gacagaccatcattttgcct tctttatgga gggagaggtt cagggaagag ctt
ctacctt ttggctatgctgcacagagg gatggcagaa tggggaaacc tttctatttggag
aaacctaggcagagctgggacaggaaa actcaactta gaagtataag acttggaaga aca
acctcca actctcagcaaccttccagc tcccgcagcc ccaccccaga cacaaggactgca
```

Figure 9-CONT.

```
gctaaac ctcagaaggtcaggagagaa agcagccctg gggttgaata ggccaacctgctg
gctttac agggggaaaaccaaatccc aggagactaa gtgacatgcc cagaaacacacag
cattcca atgggagattcaggcctaga gcatgtcctg tggctccagt ctggaggtcacac
catgacc tcttaggtcctctctggcac ggcctattgg ttttctagga cttggtgttctcc
aagagac atttcattccctaaggcctt actcctcact gtgacataat cccagaacgcatc
tctgctc cttggtcagtgaagcgatga gggtggacac aaggactaga caagagcagacag
tgagctg gcacctgacccacccttgca gaacagccct gcagacagat ctccttgttggct
ctcacct gggaacaaggaggctcctag gaggaccttt ctctgcccct ccacatttccacc
cttctct ctctgctgcttttgggaaat gatagtccag aggtggtaga acagtaccctgcc
caaggga agaggggatgctaaaaaacc agatacttct gcagattccc aaggtttcatcta
tttcctt tgccttcagcctgtgcatcagacctcttctgtctttcagg **ttgacagtagcttct
aag**
```

Figure 10: Amino acid sequence alignment of the human β-defensins 1-3.

Conserved amino acids are bold.
The conserved six cysteine motif is underlined:

Exon 1:

| | | | | | | | | | | | | | | | | | | |
|---|---|---|---|---|---|---|---|---|---|---|---|---|---|---|---|---|---|---|
| hBD-1 | M | R | T | S | Y | L | L | L | F | T | L | C | L | L | L | S | E | M | A | S | G |
| hBD-2 | M | R | V | L | Y | L | L | F | S | F | L | F | I | F | L | M | P | L | - | P | G |
| hBD-3 | M | R | I | H | Y | L | L | F | A | L | L | F | L | F | L | V | P | V | - | P | G |

Exon 2:

| | | | | | | | | | | | | | | | | | | | | | |
|---|---|---|---|---|---|---|---|---|---|---|---|---|---|---|---|---|---|---|---|---|---|
| hBD-1 | N | F | L | T | G | L | G | H | R | S | D | H | Y | N | C | V | S | S | G | G | Q | C | L | Y |
| hBD-2 | G | V | F | G | G | I | G | - | - | - | D | P | V | T | C | L | K | S | G | A | I | C | H | P |
| hBD-3 | - | - | H | G | G | I | I | N | T | L | Q | K | Y | Y | C | R | V | G | G | R | C | A | V |

Exon 2:

| | | | | | | | | | | | | | | | | | | | |
|---|---|---|---|---|---|---|---|---|---|---|---|---|---|---|---|---|---|---|---|
| hBD-1 | S | A | C | P | I | F | T | K | I | Q | G | T | C | Y | R | G | K | A | K | C | C | K | - | - | - |
| hBD-2 | V | F | C | P | R | R | Y | K | Q | I | G | T | C | G | L | P | G | T | K | C | C | K | - | K | P |
| hBD-3 | L | S | C | L | P | K | E | E | Q | I | G | K | C | S | T | R | G | R | K | C | C | R | R | K | K |

Schematic demonstrating characteristic β-defensin covalent cysteine disulfide bond formation Mammalian Expression Construct:

Figure 18
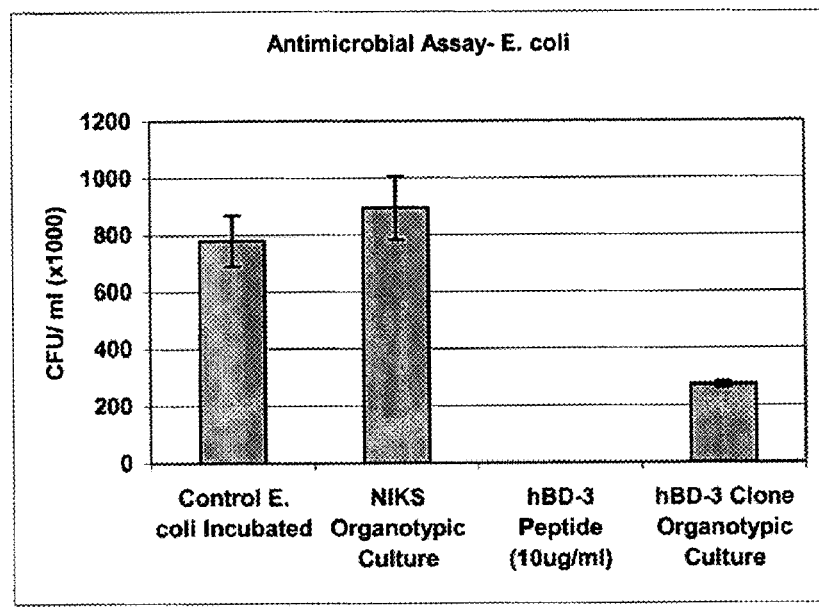
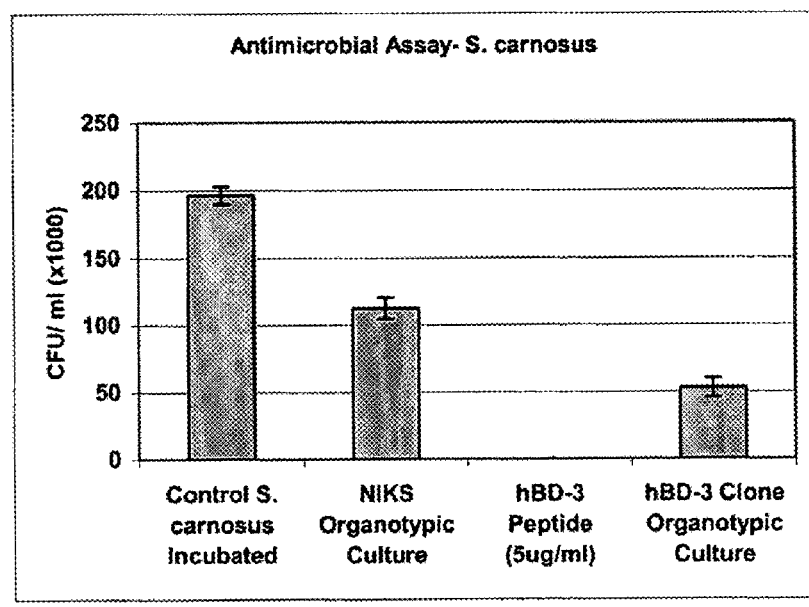

Figure 19
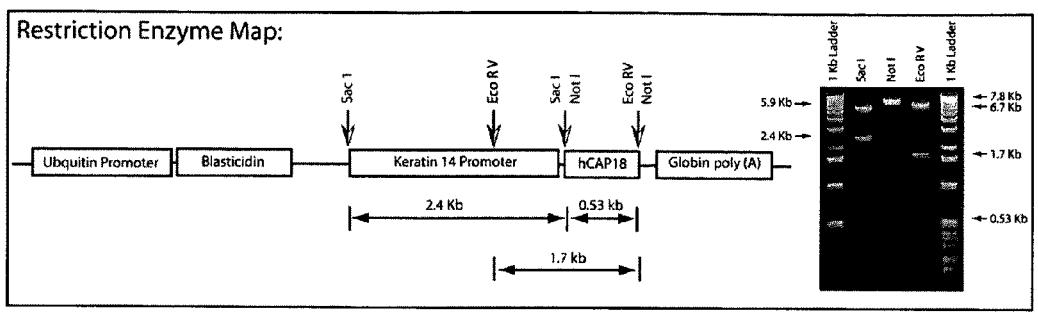
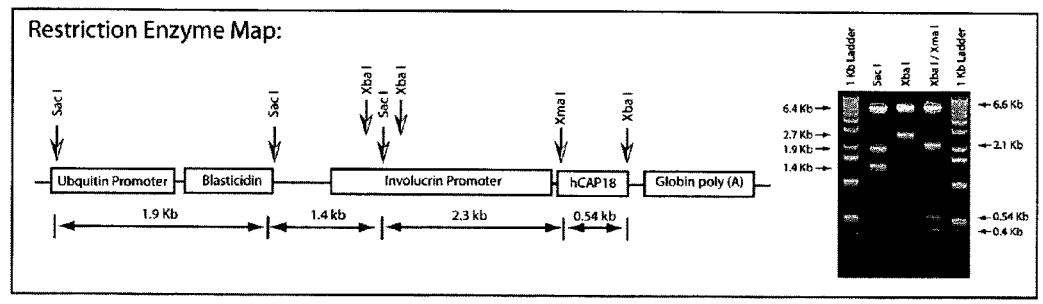

HUMAN SKIN EQUIVALENTS EXPRESSING EXOGENOUS POLYPEPTIDES

CROSS REFERENCE TO RELATED APPLICATIONS

This application is a continuation of U.S. application Ser. No. 10/909,119, filed Jul. 30, 2004 (allowed), which claims priority to provisional patent application Ser. Nos. 60/491,869, filed Aug. 1, 2003, and 60/493,664, filed Aug. 8, 2003, all of which are herein incorporated by reference in their entirety.

STATEMENT REGARDING FEDERALLY SPONSORED RESEARCH OR DEVELOPMENT

This invention was made with government support under STTR Fast-Track Grant Phase I No.: N#1 R41 AR 0530349-01 and Phase II #4 R42 AR 050349-02 awarded by the National Institutes of Health. The government may have certain rights in the invention.

FIELD OF THE INVENTION

The present invention relates generally to compositions for wound closure. More specifically, the present invention provides human skin equivalents engineered to express exogenous polypeptides (e.g., antimicrobial polypeptides and keratinocyte growth factor 2) and compositions and methods for making human skin equivalents engineered to express exogenous polypeptides. In addition, the present invention provides methods for treatment of wounds with human skin equivalents engineered to express exogenous polypeptides.

BACKGROUND

Chronic wounds affect three million people each year in the U.S. Chronic wounds generally involve any break, or ulceration, of the skin that is of long duration or recurs frequently. Such wounds cause pain, loss of function, force changes in an individual's life through potential lack of mobility, take extended periods of time for recovery, and require high amounts of patient compliance for recovery.

Chronic wounds disrupt the integrity of the skin by tearing, cutting, piercing or breaking the tissue. The causes may be structural, such as injury, or physiological, such as an underlying disease. The most frequently occurring skin wounds are venous ulcers, pressure ulcers and diabetic foot ulcers.

Chronic wounds are a serious health concern with substantial morbidity. They also are a source of frustration to both physician and patient, as lengthy treatments, treatment failures and the need for long periods of patient compliance prove challenging. The wounds take so long to heal that compliance drops off and worsens when reversals occur or new ulcers appear.

Chronic wounds occur in individuals with underlying diseases of various types whose medical conditions compromise the body's ability to repair injured tissue on its own. Despite the use of a variety of medical and surgical treatments, chronic wounds can take months or even years to heal and frequently recur. These wounds are often large and unsightly and may be painful in some patients.

Chronic wounds are of three major types: venous stasis ulcers, diabetic ulcers and pressure ulcers. A venous ulcer is an ulceration that develops on the ankle or lower leg in patients with chronic vascular disease. In these patients, blood flow in the lower extremities is impaired, leading to edema (swelling) and mild redness and scaling of the skin that gradually progress to ulceration. Venous ulcers are a condition affecting 500,000-700,000 patients in the US and 1.3 million people in the industrialized world.

A diabetic ulcer is a chronic wound that occurs in patients with diabetes. While the actual cause of the ulcer in these patients is an injury such as a callus, blister or foreign body such as a pebble or splinter, it is the patient's underlying disease that places him or her at high risk for developing an ulcer. Important risk factors include: inadequate local blood supply, which impairs their ability to repair injured tissue and ward off infection, and reduced sensation in the extremities, which causes the initial injury to go unrecognized until it becomes a serious, chronic wound. Diabetic ulcers are a condition affecting just under 500,000 patients in the US and 1.2 million people in the industrialized world.

A pressure ulcer is defined as any lesion caused by unrelieved pressure on tissues that are located over a bony prominence on the body. Pressure ulcers were formerly referred to as bedsores or decubitus ulcers. Pressure ulcers develop in immobile patients whose tissues are subjected to continuous pressure from bones on the interior and hard surfaces such as beds or chairs on the exterior. In addition to their immobility, patients at risk for the development of pressure ulcers typically have poor nutritional status, inadequate hydration, and other underlying medical conditions that compromise their ability to heal injuries. Pressure ulcers affect over 1.6 million people in the US and 4.1 million people in the industrialized world. Estimates of the prevalence of these conditions vary greatly. Estimates as high as 12 million patients have been reported for all types of chronic wounds in the industrialized markets.

Chronic wounds can be of variable sizes and depths. In general, there are four layers of tissue that can potentially sustain injury in a wound, the epidermis, or outermost layer; the dermis; the subcutaneous tissue; and, at the deepest layer, muscle, tendon, and bone. Partial-thickness ulcers involve a loss of skin that is limited to the epidermis and, potentially, part of the dermis. These wounds heal by epithelialization (proliferation and migration of epithelial cells). Full-thickness ulcers involve damage or necrosis of the epidermis, dermis, and subcutaneous tissue, and may extend into the connective tissue below the dermis. These wounds heal by granulation (filling of the wound with connective tissue), contraction, and epithelialization. The most severe category of ulcer involves injury to the epidermis, dermis, subcutaneous tissue, and muscle, tendon, or bone. The wound healing process is not complete even after the wound has closed. The process of rebuilding normal skin and tissue in a wound can take up to two years after the initial injury.

Treatment of chronic wounds varies with the severity of the wound. Partial- and full-thickness wounds are typically treated with dressings and debridement (use of chemicals or surgery to clear away necrotic, or dead, tissue). Antibiotics may be used in the event of an infection. Partial-thickness to full-thickness wounds represent the largest categories of chronic wound patients, the areas of greatest unmet medical need, and the categories most amenable to treatment with prescription growth factor therapy such as Repifermin. Patients with full-thickness wounds extending into muscle, tendon or bone are at significant risk of sepsis and are typically treated with surgery.

Despite the number of conservative therapies available, chronic wounds remain a very frustrating problem for health care practitioners because of the time-consuming nature of treatment regimens and patient non-compliance. What is needed is a therapy that can increase a practitioner's success in healing chronic wounds and/or accelerate the rate of chronic wound healing.

SUMMARY OF THE INVENTION

The present invention relates generally to compositions for wound closure. More specifically, the present invention provides human skin equivalents engineered to express exogenous polypeptides (e.g., antimicrobial polypeptides and keratinocyte growth factor 2) and compositions and methods for making human skin equivalents engineered to express exogenous polypeptides. In addition, the present invention provides methods for treatment of wounds with human skin equivalents engineered to express exogenous polypeptides.

Accordingly, in some embodiments, the present invention provides methods for providing cells expressing heterologous KGF-2 comprising: a) providing a host cell selected from the group consisting of primary keratinocytes and immortalized keratinocytes and an expression vector comprising a DNA sequence encoding KGF-2 operably linked to a regulatory sequence; b) introducing the expression vector to the host cell (e.g., under conditions such that said expression vector is internalized by the host cell); and c) culturing the host cells under conditions such that KGF-2 is expressed. The present invention is not limited to the use of any particular primary or immortalized keratinocytes. In some preferred embodiments, the keratinocytes are NIKS cells or cell derived from NIKS cells. In other embodiments, the keratinocytes are capable of stratifying into squamous epithelia. In still other embodiments, the methods include the step of co-culturing the host cells with cells derived from a patient. The present invention is not limited to the use of any particular expression vector. In some embodiments, the expression vector further comprises a selectable marker. The present invention is not limited to the use of any particular regulatory sequence. In some embodiments, the regulatory sequence is a promoter sequence. The present invention is not limited to any particular promoter sequence. In some embodiments, the promoter sequence is K14 promoter sequence, preferably a full-length K14 promoter sequence. In other embodiments, the promoter is an involucrin promoter. In preferred embodiments, the promoter sequence allows expression in a keratinocyte. In still further embodiments, the present invention provides host cells produced by the foregoing method.

In some embodiments, the present invention provides compositions comprising host cells expressing heterologous KGF-2, wherein the host cells are selected from the group consisting of primary and immortalized keratinocytes. In some embodiments, the host cells are NIKS cells or cell derived from NIKS cells. In further embodiments, the KGF-2 is full length KGF-2.

In further embodiments, the present invention provides methods of treating wounds comprising: a) providing immortalized keratinocytes expressing heterologous KGF-2, and a subject with a wound; and b) contacting the wound with the immortalized cells expressing heterologous KGF-2. The present invention is not limited to any particular type of contacting. Indeed, a variety of ways of contacting are contemplated. In some embodiments, the contacting comprises topical application. In other embodiments, the contacting comprises engraftment. In still other embodiments, the contacting comprises wound dressing. The present invention is not limited to the treatment of any particular type of wound. Indeed, the treatment of a variety of wounds is contemplated, including, but not limited to those selected from the group comprising venous ulcers, diabetic ulcers, pressure ulcers, burns, ulcerative colitis, mucosal injuries, internal injuries, external injuries. In some embodiments, the immortalized keratinocytes are NIKS cells. In further embodiments, the immortalized keratinocytes are incorporated into a human skin equivalent. In still further embodiments, the human skin equivalent further comprises cells derived from a patient. In other embodiments, the methods further comprise the step mixing the keratinocytes expressing heterologous KGF-2 with cells derived from the subject prior to the contacting step.

In still other embodiments, the present invention provides vectors comprising a keratinocyte specific promoter operably linked to a DNA sequence encoding KGF-2. In some embodiments, the keratinocyte specific promoter is the K14 promoter or the involucrin promoter. The present invention also provides host cells and skin equivalents comprising these vectors.

In other embodiments, the present invention provides a method for providing a tissue (e.g., human skin equivalent) expressing an exogenous antimicrobial polypeptide or peptide comprising providing a keratinocyte and an expression vector comprising a DNA sequence encoding an antimicrobial polypeptide or peptide thereof operably linked to a regulatory sequence; introducing the expression vector into the keratinocyte; and incorporating the keratinocyte into a tissue (e.g., human skin equivalent). In some embodiments, the keratinocyte is capable of stratifying into squamous epithelia. In some embodiments, the keratinocyte is selected a primary or immortalized keratinocyte (e.g. preferably NIKS cells). In certain embodiments, the expression vector further comprises a selectable marker. In some preferred embodiments, the regulatory sequence is a promoter sequence (e.g., an involucrin promoter or a keratin-14 promoter). In certain preferred embodiments, the promoter sequence allows antimicrobial polypeptide expression in the host cell. The present invention is not limited to a particular antimicrobial polypeptide. Indeed, a variety of antimicrobial polypeptides is contemplated including, but not limited to, human beta defensin 1, 2, and 3 and human cathelicidin. In some embodiments, the human beta defensin 3 has a mutated amino acid sequence (e.g., one or more single amino acid substitutions). In some preferred embodiments, the one or more single amino acid substitutions comprise Cys40Ala, Cys45Ala, Cys55Ala, Cys62Ala, and Cys63Ala. In other embodiments, the single amino acid substitution is Gly38Ala. In particularly preferred embodiments, the mutated human beta defenin 3 has antimicrobial activity. In other embodiments, the expression vector further comprises a nucleic acid sequence encoding a signal secretion peptide. In preferred embodiments, the skin equivalent exhibits antimicrobial activity. The present invention additionally provides a skin equivalent produced by the method described herein.

In yet other embodiments, the present invention provides a composition comprising keratinocytes (e.g., primary or immortalized keratinocytes) expressing an exogenous antimicrobial polypeptide. In preferred embodiments, the keratinocytes are NIKS cells or cells derived from NIKS cells. The present invention is not limited to a particular antimicrobial polypeptide. Indeed, a variety of antimicrobial polypeptides is contemplated including, but not limited to, human beta defensin 1, 2, and 3 and human cathelicidin. In some embodiments, the human beta defensin 3 has a mutated amino acid sequence (e.g., one or more single amino acid substitutions). In some preferred embodiments, the one or more single amino acid substitutions comprise Cys40Ala, Cys45Ala, Cys55Ala, Cys62Ala, and Cys63Ala. In other embodiments, the single amino acid substitution is Gly38Ala. In some embodiments, the keratinocytes are stratified. In other embodiments, the composition further comprises a dermal equivalent. In yet other embodiments, the present invention provides an organotypic culture of the keratinocytes. In other embodiments, the composition further comprises cells derived from a patient. In still further embodiments, the composition further comprises keratinocytes that do not express the exogenous antimicrobial polypeptide. In yet other embodiments, the composition further comprises keratinocytes expressing at least one additional exogenous (e.g., antimicrobial) polypeptide.

The present invention further provides a method of treating wounds comprising: providing primary or immortalized keratinocytes (e.g., NIKS cells) expressing a exogenous antimicrobial polypeptide, and a subject with a wound; contacting the wound with the immortalized keratinocytes expressing an exogenous antimcrobial polypeptide. The present invention is not limited to a particular antimicrobial polypeptide. Indeed, a variety of antimicrobial polypeptides is contemplated including, but not limited to, human beta defensin 1, 2, and 3 and human cathelicidin. In some embodiments, the human beta defensin 3 has a mutated amino acid sequence (e.g., one or more single amino acid substitutions). In some preferred embodiments, the one or more single amino acid substitutions comprise Cys40Ala, Cys45Ala, Cys55Ala, Cys62Ala, and Cys63Ala. In other embodiments, the single amino acid substitution is Gly38Ala. In some embodiments, the contacting comprises engraftment, topical application, or wound dressing. The present invention contemplates treatment of any type of wound, including, but not limited to, venous ulcers, diabetic ulcers, pressure ulcers, burns, ulcerative colitis, mucousal injuries, internal injuries, and external injuries. In some embodiments, the human skin equivalent further comprises cells derived from a patient.

The present invention additionally provides a vector comprising a keratinocyte specific promoter (e.g., involucrin promoter or the keratin-14 promoter) operably linked to a DNA sequence encoding an antimicrobial polypeptide. The present invention is not limited to a particular antimicrobial polypeptide. Indeed, a variety of antimicrobial polypeptides is contemplated including, but not limited to, human beta defensin 1, 2, and 3 and human cathelicidin. In some embodiments, the human beta defensin 3 has a mutated amino acid sequence (e.g., one or more single amino acid substitutions). The present invention further provides a host cell comprising the vector. The present invention also provides a human tissue (e.g., skin equivalent) comprising the host cell. In some embodiments, the human tissue (e.g., skin equivalent) further comprises cells derived from a patient. In other embodiments, the human tissue (e.g., skin equivalent) further comprises keratinocytes not comprising the vector. In yet other embodiments, the human skin equivalent further comprises keratinocytes expressing at least one additional antimicrobial polypeptide.

In yet other embodiments, the present invention provides a method for providing a human tissue (e.g., skin equivalent) expressing an exogenous KGF-2 and an exogenous antimicrobial polypeptide comprising providing a keratinocyte; a first expression vector comprising a DNA sequence encoding an antimicrobial polypeptide operably linked to a regulatory sequence; and a second expression vector comprising a DNA encoding an exogenous KGF-2 polypeptide; and introducing the expression vector into the keratinocyte; and incorporating the keratinocyte into a human tissue (e.g., skin equivalent).

In still other embodiments, the present invention provides a method of selecting cells with increased pluripotency or multipotency relative to a population, comprising providing a population of cells; electroporating the cells under conditions such that electroporated cells with increased pluripotency or multipotency relative to the population of cells are selected. In some embodiments, the electroporated cells exhibit stem cell like properties. In some embodiments, the population of cells are keratinocytes and the electroporated keratinocytes have holoclone or meroclone cell morphology. In other embodiments, the electroporated cells exhibit extended proliferative capacity. In some embodiments, the population of cells is electroporated with an exogenous nucleic acid expressing a selectable marker. In certain embodiments, the method further comprises the step of culturing the cells under conditions such that only cells expressing the selectable marker are selected for. The present invention additionally provides a cell or population of cells generated by the method.

In certain embodiments, the present invention provides a method of selecting keratinocytes with holoclone or meroclone cell morphology, comprising providing a population of keratinocytes; and electroporating the keratinocytes under conditions such that electroporated keratinocytes with holoclone or meroclone cell morphology are selected. In some embodiments, the holoclone cell morphology comprises one or more properties selected from the group consisting of tightly packed cells, cells uniform in size, colonies with smooth colony edges, and an overall round colony morphology. In some embodiments, the population of keratinocytes is electroporated with an exogenous nucleic acid expressing a selectable marker. In certain embodiments, the method further comprises the step of culturing the keratinocytes under conditions such that only cells expressing the selectable marker are selected for. The present invention also provides a keratinocyte population generated by the method.

A method for providing tissues expressing heterologous KGF-2 and/or antimicrobial polypeptide comprising providing a tissue and an expression vector comprising a DNA sequence encoding KGF-2 and/or antimicrobial polypeptide operably linked to a regulatory sequence; introducing said expression vector to said tissue under conditions such that said expression vector is internalized by a host cell contained in said tissue and said KGF-2 and/or antimicrobial polypeptide is expressed. In some embodiments, the tissue is a human tissue (e.g., a human skin equivalent). In some embodiments, the expression vector is introduced to the tissue by particle bombardment, electroporation, or transfection.

DESCRIPTION OF THE FIGURES

FIG. 1 (SEQ ID NO: 120) provides the consensus sequence of the K14 promoter.

FIG. 6 provides the DNA sequence for human beta defensin 1 (SEQ ID NO:9).

FIG. 7 provides the DNA sequence for human beta defensin 2 (SEQ ID NO:10).

FIG. 8 provides the DNA sequence for human beta defensin 3 (SEQ ID NO:11).

FIG. 9 provides the DNA sequence for the involucrin promoter (SEQ ID NO: 12).

FIG. 10 (SEQ ID NOS: 121-123) provides amino acid sequence alignments of the human β-defensins 1-3

FIG. 18 shows the antimicrobial activity of human β-defensins 3 in an organotypic culture.

FIG. 19 shows a linear map and restriction digest analysis of the hCAP18 vector.

DEFINITIONS

Figure 2:
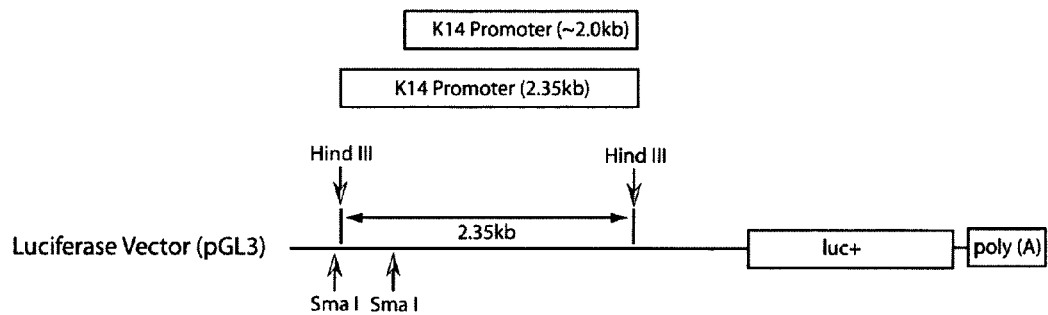
FIG. 2 provides a diagram of the construction of the K14-luciferase vector.

As used herein, the term "growth factor" refers to extracellular molecules that bind to a cell-surface triggering an intracellular signaling pathway leading to proliferation, differentiation, or other cellular response. Examples of growth factors include, but are not limited to, growth factor I, trophic factor, $Ca^{2+}$, insulin, hormones, synthetic molecules, pharmaceutical agents, and LDL.

As used herein, the term "keratinocyte growth factor" or "KGF" refers to a member of a group of structurally distinct proteins known as FGFs that display varying degrees of sequence homology, suggesting that they are encoded by a related family of genes. The FGFs share common receptor sites on cell surfaces. KGF, for example, can bind to FGFR-3.

As used herein, the term "antimicrobial polypeptide" refers to polypeptides and peptides thereof that inhibit the growth of microbes (e.g., bacteria). Examples of antimicrobial polypeptides include, but are not limited to, the polypeptides described in Table 1 below (e.g., defensins or cathelicidins). Antimicrobial polypeptides include peptides synthesized from both L-amino and D-amino acids. "Antimicrobial polypeptides" also include peptide portions of the antimicrobial polypeptide, obtained by any method (e.g., synthesized or enzymatically obtained).

As used herein, the term "defensin" refers to a family of highly cross-linked, structurally homologous antimicrobial peptides that are generally, but not necessarily, found in the azurophil granules of polymorphonuclear leukocytes (PMN's) with homologous peptides being present in macrophages.

As used herein, the terms "human beta-defensin 1" or "hBD1", when used in reference to a protein or nucleic acid refers to a protein or nucleic acid encoding a protein that shares greater than about 50% identity with SEQ ID NO: 13 and also has at least one activity of wild type hBD1. Thus, the term hBD1 protein encompasses both proteins that are identical to wild-type hBD1 protein and those that are derived from wild type hBD1 protein (e.g., variants of hBD1 protein or chimeric genes constructed with portions of hBD1 protein coding regions).

As used herein, the term "activity of hBD1" refers to any activity of wild type hBD1 protein (e.g., antimicrobial activity). The term is intended to encompass all activities of hBD1 protein, alone or in combination.

In particular, the term "hBD1 gene" refers to the full-length hBD1 nucleotide sequence (e.g., contained in SEQ ID NO:9). However, it is also intended that the term encompass fragments of the hBD1 sequence, as well as other domains within the full-length hBD1 nucleotide sequence, as well as variants of hBD1. Furthermore, the terms "hBD1 gene nucleotide sequence" or "hBD1 gene polynucleotide sequence" encompasses DNA, cDNA, and RNA (e.g., mRNA) sequences.

As used herein, the terms "human beta-defensin 2" or "hBD2", when used in reference to a protein or nucleic acid refers to a protein or nucleic acid encoding a protein that shares greater than about 50% identity with SEQ ID NO:14 and also has at least one activity of wild type hBD2. Thus, the term hBD2 protein encompasses both proteins that are identical to wild-type hBD2 protein and those that are derived from wild type hBD2 protein (e.g., variants of hBD2 protein or chimeric genes constructed with portions of hBD2 protein coding regions).

As used herein, the term "activity of hBD2" refers to any activity of wild type hBD2 protein (e.g., antimicrobial activity). The term is intended to encompass all activities of hBD2 protein, alone or in combination.

In particular, the term "hBD2 gene" refers to the full-length hBD1 nucleotide sequence (e.g., contained in SEQ ID NO:10). However, it is also intended that the term encompass fragments of the hBD1 sequence, as well as other domains within the full-length hBD2 nucleotide sequence, as well as variants of hBD1. Furthermore, the terms "hBD2 gene nucleotide sequence" or "hBD1 gene polynucleotide sequence" encompasses DNA, cDNA, and RNA (e.g., mRNA) sequences.

As used herein, the terms "human beta-defensin 3" or "hBD3", when used in reference to a protein or nucleic acid refers to a protein or nucleic acid encoding a protein that shares greater than about 50% identity with SEQ ID NO:15 and also has at least one activity of wild type hBD3. Thus, the term hBD3 protein encompasses both proteins that are identical to wild-type hBD3 protein and those that are derived from wild type hBD3 protein (e.g., variants of hBD3 protein or chimeric genes constructed with portions of hBD3 protein coding regions).

As used herein, the term "activity of hBD3" refers to any activity of wild type hBD3 protein (e.g., antimicrobial activity). The term is intended to encompass all activities of hBD1 protein, alone or in combination.

In particular, the term "hBD3 gene" refers to the full-length hBD3 nucleotide sequence (e.g., contained in SEQ ID NO:11). However, it is also intended that the term encompass fragments of the hBD3 sequence, as well as other domains within the full-length hBD3 nucleotide sequence, as well as variants of hBD3. Furthermore, the terms "hBD3 gene nucleotide sequence" or "hBD3 gene polynucleotide sequence" encompasses DNA, cDNA, and RNA (e.g., mRNA) sequences.

As used herein, the term "NIKS cells" refers to cells having the characteristics of the cells deposited as cell line ATCC CRL-12191.

The term "gene" refers to a nucleic acid (e.g., DNA) sequence that comprises coding sequences necessary for the production of a polypeptide or precursor (e.g., GKLF). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "recombinant DNA molecule" as used herein refers to a DNA molecule that is comprised of segments of DNA joined together by means of molecular biological techniques.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding KGF-2 includes, by way of example, such nucleic acid in cells ordinarily expressing KGF-2 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and antisense strands (i.e., the oligonucleotide or polynucleotide may be double-stranded).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets that specify stop codons (i.e., TAA, TAG, TGA).

As used herein, the term "purified" or "to purify" refers to the removal of contaminants from a sample.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

A "regulatory sequence" refers to a polynucleotide sequence that is necessary for regulation of expression of a coding sequence to which the polynucleotide sequence is operably linked. The nature of such regulatory sequences differs depending upon the host organism. In prokaryotes, such regulatory sequences generally include, for example, a promoter, and/or a transcription termination sequence. In eukaryotes, generally, such regulatory sequences include, for example, a promoter and/or a transcription termination sequence. The term "regulatory sequence" may also include additional components the presence of which are advantageous, for example, a secretory leader sequence for secretion of the polypeptide attached thereto.

"Operably linked" refers to a juxtaposition wherein the components so described are in a relationship permitting them to function in their intended manner. A regulatory sequence is "operably linked" to a coding sequence when it is joined in such a way that expression of the coding sequence is achieved under conditions compatible with the regulatory sequence.

"PCR" refers to the techniques of the polymerase chain reaction as described in Saiki, et al., Nature 324:163 (1986); and Scharf et al., Science 233:1076-1078 (1986); U.S. Pat. No. 4,683,195; and U.S. Pat. No. 4,683,202. As used herein, x is "heterologous" with respect to y if x is not naturally associated with y or x is not associated with y in the same manner as is found in nature.

By "pharmaceutically acceptable carrier," is meant any carrier that is used by persons in the art for administration into a human that does not itself induce any undesirable side effects such as the production of antibodies, fever, etc. Suitable carriers are typically large, slowly metabolized macromolecules that can be a protein, a polysaccharide, a polylactic acid, a polyglycolic acid, a polymeric amino acid, amino acid copolymers or an inactive virus particle. Such carriers are well known to those of ordinary skill in the art. Preferably the carrier is thyroglobulin.

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the KGF-2 mRNA-specific signal observed on Northern blots). The amount of mRNA present in the band corresponding in size to the correctly spliced KGF-2 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA does not integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]) has been modified by several groups to optimize conditions for particular types of cells. The art is well aware of these numerous modifications.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response", when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyl-transferase, Beta-galactosidase, alkaline phosphatase, and horse radish peroxidase.

DETAILED DESCRIPTION

The present invention provides human skin equivalents (e.g., NIKS cells) expressing exogenous polypeptides (e.g., KGF-2 and antimicrobial polypeptides), and compositions and methods for making such cells. In addition, the present invention provides methods for treatment of wounds with such cells.

I. Methods of Generating Host Cells

In some embodiments, the present invention provides methods of generating human tissues such as skin equivalents (e.g., from NIKS cells) expressing exogenous polypeptides (e.g., KGF-2 and antimicrobial polypeptides).

A) Host Cells

Generally, any source of cells or cell line that can stratify into squamous epithelia is useful in the present invention. Accordingly, the present invention is not limited to the use of any particular source of cells that are capable of differentiating into squamous epithelia. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cavaderic donors (Auger et al., In Vitro Cell. Dev. Biol.—Animal 36:96-103; U.S. Pat. Nos. 5,968,546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucamp et al., J. cell. Boil. 106:761-771 (1988)); and NIKS cells (Cell line BC-1-Ep/SL; U.S. Pat. No. 5,989,837, incorporated herein by reference; ATCC CRL-12191). Each of these cell lines can be cultured or genetically modified as described below in order to produce a cell line capable of expressing an exogenous polypeptide.

In particularly preferred embodiments, NIKS cells or cells derived from NIKS cells are utilized. NIKS cells (Cell line BC-1-Ep/SL; U.S. Pat. Nos. 5,989,837, 6,514,711, 6,495, 135, 6,485,724, and 6,214,567; each of which is incorporated herein by reference; ATCC CRL-12191). The discovery of a novel human keratinocyte cell line (near-diploid immortalized keratinocytes or NIKS) provides an opportunity to genetically engineer human keratinocytes for new therapeutic methods. A unique advantage of the NIKS cells is that they are a consistent source of genetically-uniform, pathogen-free human keratinocytes. For this reason, they are useful for the application of genetic engineering and genomic gene expression approaches to provide skin equivalent cultures with properties more similar to human skin. Such systems will provide an important alternative to the use of animals for testing compounds and formulations. The NIKS keratinocyte cell line, identified and characterized at the University of Wisconsin, is nontumorigenic, exhibits a stable karyotype, and undergoes normal differentiation both in monolayer and organotypic culture. NIKS cells form fully stratified skin equivalents in culture. These cultures are indistinguishable by all criteria tested thus far from organotypic cultures formed from primary human keratinocytes. Unlike primary cells however, the immortalized NIKS cells will continue to proliferate in monolayer culture indefinitely. This provides an opportunity to genetically manipulate the cells and isolate new clones of cells with new useful properties (Allen-Hoffmann et al., J. Invest. Dermatol., 114(3): 444-455 (2000)).

The NIKS cells arose from the BC-1-Ep strain of human neonatal foreskin keratinocytes isolated from an apparently normal male infant. In early passages, the BC-1-Ep cells exhibited no morphological or growth characteristics that were atypical for cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3\times10^5$ cells per 100-mm dish and passaged at weekly intervals (approximately a 1:25 split). By passage 15, most keratinocytes in the population appeared senescent as judged by the presence of numerous abortive colonies that exhibited large, flat cells. However, at passage 16, keratinocytes exhibiting a small cell size were evident. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that survived senescence were serially cultivated at a density of $3\times10^5$ cells per 100-mm dish. Typically the cultures reached a cell density of approximately $8\times10^6$ cells within 7 days. This stable rate of cell growth was maintained through at least 59 passages, demonstrating that the cells had achieved immortality. The keratinocytes that emerged from the original senescencing population were originally designated BC-1-Ep/Spontaneous Line and are now termed NIKS. The NIKS cell line has been screened for the presence of proviral DNA sequences for HIV-1, HIV-2, EBV, CMV, HTLV-1, HTLV-2, HBV, HCV, B-19 parvovirus, HPV-16 and HPV-31 using either PCR or Southern analysis. None of these viruses were detected.

Chromosomal analysis was performed on the parental BC-1-Ep cells at passage 3 and NIKS cells at passages 31 and 54. The parental BC-1-Ep cells have a normal chromosomal complement of 46, XY. At passage 31, all NIKS cells contained 47 chromosomes with an extra isochromosome of the long arm of chromosome 8. No other gross chromosomal abnormalities or marker chromosomes were detected. At passage 54, all cells contained the isochromosome 8.

The DNA fingerprints for the NIKS cell line and the BC-1-Ep keratinocytes are identical at all twelve loci analyzed demonstrating that the NIKS cells arose from the parental BC-1-Ep population. The odds of the NIKS cell line having the parental BC-1-Ep DNA fingerprint by random chance is $4\times10^{-16}$. The DNA fingerprints from three different sources of human keratinocytes, ED-1-Ep, SCC4 and SCC13y are different from the BC-1-Ep pattern. This data also shows that keratinocytes isolated from other humans, ED-1-Ep, SCC4, and SCC13y, are unrelated to the BC-1-Ep cells or each other. The NIKS DNA fingerprint data provides an unequivocal way to identify the NIKS cell line.

Loss of p53 function is associated with an enhanced proliferative potential and increased frequency of immortality in cultured cells. The sequence of p53 in the NIKS cells is identical to published p53 sequences (GenBank accession number: M14695). In humans, p53 exists in two predominant polymorphic forms distinguished by the amino acid at codon 72. Both alleles of p53 in the NIKS cells are wild-type and have the sequence CGC at codon 72, which codes for an arginine. The other common form of p53 has a proline at this position. The entire sequence of p53 in the NIKS cells is identical to the BC-1-Ep progenitor cells. Rb was also found to be wild-type in NIKS cells.

Anchorage-independent growth is highly correlated to tumorigenicity in vivo. For this reason, the anchorage-independent growth characteristics of NIKS cells in agar or methylcellulose-containing medium was investigated. After 4 weeks in either agar- or methylcellulose-containing medium, NIKS cells remained as single cells. The assays were continued for a total of 8 weeks to detect slow growing variants of the NIKS cells. None were observed.

To determine the tumorigenicity of the parental BC-1-Ep keratinocytes and the immortal NIKS keratinocyte cell line, cells were injected into the flanks of athymic nude mice. The human squamous cell carcinoma cell line, SCC4, was used as a positive control for tumor production in these animals. The injection of samples was designed such that animals received SCC4 cells in one flank and either the parental BC-1-Ep keratinocytes or the NIKS cells in the opposite flank. This injection strategy eliminated animal to animal variation in tumor production and confirmed that the mice would support vigorous growth of tumorigenic cells. Neither the parental BC-1-Ep keratinocytes (passage 6) nor the NIKS keratinocytes (passage 35) produced tumors in athymic nude mice.

NIKS cells were analyzed for the ability to undergo differentiation in both surface culture and organotypic culture. For cells in surface culture, a marker of squamous differentiation, the formation cornified envelopes was monitored. In cultured human keratinocytes, early stages of cornified envelope assembly result in the formation of an immature structure composed of involucrin, cystatin-α and other proteins, which represent the innermost third of the mature cornified envelope. Less than 2% of the keratinocytes from the adherent BC-1-Ep cells or the NIKS cell line produce cornified envelopes. This finding is consistent with previous studies demonstrating that actively growing, subconfluent keratinocytes produce less than 5% cornified envelopes. To determine whether the NIKS cell line is capable of producing cornified envelopes when induced to differentiate, the cells were removed from surface culture and suspended for 24 hours in medium made semi-solid with methylcellulose. Many aspects of terminal differentiation, including differential expression of keratins and cornified envelope formation can be triggered in vitro by loss of keratinocyte cell-cell and cell-substratum adhesion. The NIKS keratinocytes produced as many as and usually more cornified envelopes than the parental keratinocytes. These findings demonstrate that the NIKS keratinocytes are not defective in their ability to initiate the formation of this cell type-specific differentiation structure.

To confirm that the NIKS keratinocytes can undergo squamous differentiation, the cells were cultivated in organotypic culture. Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy there are striking differences between the architecture of the multilayered sheets formed in tissue culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the parental cells and the NIKS cells. The appearance of flattened squamous cells is evident in the upper layers of keratinocytes and demonstrates that stratification has occurred in the organotypic cultures. In the uppermost part of the organotypic cultures the enucleated squames peel off the top of the culture. To date, no histological differences in differentiation at the light microscope level between the parental keratinocytes and the NIKS keratinocyte cell line grown in organotypic culture have been observed.

To observe more detailed characteristics of the parental (passage 5) and NIKS (passage 38) organotypic cultures and to confirm the histological observations, samples were analyzed using electron microscopy. Parental cells and the immortalized human keratinocyte cell line, NIKS, were harvested after 15 days in organotypic culture and sectioned perpendicular to the basal layer to show the extent of stratification. Both the parental cells and the NIKS cell line undergo extensive stratification in organotypic culture and form structures that are characteristic of normal human epidermis. Abundant desmosomes are formed in organotypic cultures of parental cells and the NIKS cell line. The formation of a basal lamina and associated hemidesmosomes in the basal keratinocyte layers of both the parental cells and the cell line was also noted.

Hemidesmosomes are specialized structures that increase adhesion of the keratinocytes to the basal lamina and help maintain the integrity and strength of the tissue. The presence of these structures was especially evident in areas where the parental cells or the NIKS cells had attached directly to the porous support. These findings are consistent with earlier ultrastructural findings using human foreskin keratinocytes cultured on a fibroblast-containing porous support. Analysis at both the light and electron microscopic levels demonstrate that the NIKS cell line in organotypic culture can stratify, differentiate, and form structures such as desmosomes, basal lamina, and hemidesmosomes found in normal human epidermis.

B) KGF-2

In some embodiments, the present invention provides human skin equivalents (e.g., keratinocytes) that express exogenous KGF-2 protein. KGF-2 is a 208 amino acid protein that influences normal keratinocyte and epithelial cells to proliferate and migrate to wound sites. Protein and nucleic acid sequences for KGF-2 are provided in U.S. Pat. No. 6,077,692; which is incorporated herein by reference.

KGF-2 promotes wound healing in tissues containing keratinocytes and fibroblasts by having a positive proliferative effect on epithelial cells and mediating keratinocyte migration. In addition, KGF-2 promotes wound healing by increasing deposition of granulation tissue and collagen, and maturation of collagen (Soler et al., Wound Repair Regen. 7(3): 172-178 (1999)).

C) Antimicrobial Polypeptides

In some embodiments, the present invention provides human skin equivalents (e.g., keratinocytes) that express exogenous antimicrobial polypeptides. In intact human skin, the stratum corneum serves as the first line of defense against microbial organisms. The stratum corneum is the uppermost, nonviable, desiccated layer of the epidermis that is composed of fully differentiated keratinocytes. The innate immune response prevents invasion of microbial organisms if the outer most layer of the skin barrier is penetrated. This response includes phagocytosis by macrophages and neutrophils and their production of reactive oxygen intermediates that kill microbial agents. Associated with this line of defense are antimicrobial peptides that are naturally expressed and localized to the upper layers of the epidermis. The most thoroughly studied human antimicrobial peptides belong to two subfamilies, the α- and β-defensins, which differ from one another by their disulfide bond pairing, genomic organization and tissue distributions (Ganz, T. and J. Weiss, Semin Hematol, 1997. 34(4): p. 343-54). The β-defensins are characteristically found in epithelial tissues and are expressed in human keratinocytes. This defensin subfamily demonstrates strong antimicrobial activity against a broad spectrum of pathogenic agents, including bacteria, fungi and viruses.

Microorganisms have difficulty acquiring resistance to the defensin peptides, making these peptides very attractive for therapeutic use as antibiotics (Schroder, J. M., Biochem Pharmacol, 1999. 57(2): p. 121-34). In clinical trials, defensin peptides applied to skin have been found to be safe (Hancock, R. E., Lancet, 1997. 349(9049): p. 418-22). The safety of topically-applied defensins is consistent with the finding that human epidermal keratinocytes express defensin peptides in vivo.

Figure 11:
FIG. 11 is a schematic drawing demonstrating characteristic β-defensin covalent cysteine disulfide bond formation.

In the human genome, all known defensin genes cluster to a <1 Mb region of chromosome 8p22-p23; these findings suggest an evolutionary conservation of this gene family. Harder, J., et al., *Mapping of the gene encoding human beta-defensin-2 (DEFB2) to chromosome region 8p22-p23.1.* Genomics, 1997. 46(3): p. 472-5. It is generally accepted that evolutionarily conserved genes maintain some overlap in gene function. The defensin gene family is no exception to this theory. The defensin genes encode small (3-5 kDa), cationic molecules characterized by an amphipathic structure and have six cysteine residues that form three intramolecular disulfide bonds (see FIG. 11). These cationic regions are thought to be attractive to the anionic surfaces of most bacteria. The human defensin gene family is divided into two subfamilies: the α-defensins and β-defensins that differ from one another by their disulfide bond pairing, genomic organization and tissue distributions. The α- and β-defensins share similarity in tertiary structure and both contain triple stranded antiparallel beta sheets (Pardi, A., et al., Bochemistry, 1992. 31(46): p. 11357-64; Zimmermann, G. R., et al., Biochemistry, 1995. 34(41): p. 13663-71). However, their antimicrobial mechanisms of action are distinct from one another.

Historically the α-defensins have been found in storage granules of specialized cell types such as neutrophils and Paneth cells of the small intestine, whereas the β-defensins are expressed in epithelial tissues. The α-defensins also have an inhibitory pro-region in their amino-terminal sequence, which is cleaved off after release from granules. The pro-region is likely to contain a granule targeting motif but may function independently as a protease inhibitor. The broad spectrum of antimicrobial activity is mediated in part by permeabilization of biological membranes. Although extremely potent for killing invading microorganisms, α-defensins have also been shown to be toxic to eukaryotic cell types (Lichtenstein, A., et al., Blood, 1986. 68(6): p. 1407-10; Okrent et al., Am Rev Respir Dis, 1990. 141(1): p. 179-85). The α-defensin-induced pleiotropic cell killing activity makes this subfamily of defensins unattractive as a gene candidate for expression in living human skin substitutes.

Keratinocytes of the skin and other epithelia harbor endogenously expressed members of the β-defensins. To date, there have been six distinct genes identified. Three of these human β-defensin genes, hBD-1, hBD-2 & hBD-3, are expressed in epidermal keratinocytes of the skin. The first exon encodes the signal sequence and propeptide and the second exon encodes the mature peptide. Amino acid sequence alignment highlighting conserved residues and the characteristic six cysteine residues of the human β-defensins 1-3 are shown in FIG. 10. The disulfide covalent bonds required for secondary structure of the active peptide are demonstrated in FIG. 11.

Several factors are thought to contribute to the antimicrobial action of the β-defensins on microbes. First because of their cationic and amphiphilic characteristics, antimicrobial peptides bind and insert into the cytoplasmic membrane, where they assemble into multimeric pores, and destroy the target microbe by changing membrane conductance and altering intracellular function (White, S. H., W. C. Wimley, and M. E. Selsted, Curr Opin Struct Biol, 1995. 5(4): p. 521-7; Boman, H. G., Annu Rev Immunol, 1995. 13: p. 61-92). Most antimicrobial peptides kill microorganisms by forming pores in the cell membrane. These peptides are not toxic to mammalian cells due to the sensitivity of these peptide antibiotics to cholesterol and phospholipids, major components of mammalian cell membranes. The β-defensins are attractive candidates for therapeutic use as antibiotics since it is difficult for microorganisms to acquire resistance to the peptides' bactericidal mechanism of action (Schroder, J. M., Biochem Pharmacol, 1999. 57(2): p. 121-34).

When expressed, the β-defensin peptides appear to initially localize to the cytoplasm of undifferentiated or less differentiated keratinocytes. As these cells differentiate and move closer to the epidermal surface, they secrete these antimicrobial peptides onto the keratinocyte membrane or into the intracellular space. The signal peptide sequence is thought to contribute to the specialized localization of this active peptide. Finally human β-defensin peptides accumulate in the dehydrated cells of the epidermal surface. Studies demonstrate that, although the three β-defensin genes are very similar, their expression is determined by completely different regulatory mechanisms (Frye, M., J. Bargon, and R. Gropp, J Mol Med, 2001. 79(5-6): p. 275-82).

The burn wound is an ideal environment for bacterial growth and provides a pathway for microbial invasion. Luterman and coworkers concluded "Burned skin is a nidus and portal for bacterial invasion, causing burn wound sepsis, the leading cause of death in burn units around the world" (Luterman, A., C. C. Dacso, and P. W. Curreri, Am J Med, 1986. 81(1A): p. 45-52). Infection is further promoted by skin loss and post burn immuno-suppression. As expected, human defensin gene expression is diminished in full thickness burn wounds most probably due to the destruction of the epithelium. For example, human β-defensin gene (hBD-2) expression is virtually undetectable in the burn wound suggesting the loss of defensins due to thermal destruction of the skin (Milner, S. M. and M. R. Ortega, Burns, 1999. 25(5): p. 411-3). A routinely used debridement procedure may also contribute to significant removal of epithelia in a wound bed. Debridement speeds the healing of ulcers, burns, and other wounds by removing dead tissue so that the remaining living tissue can adequately heal. Wounds that contain non-living (necrotic) tissue take longer to heal because necrotic debris is a nutrient source for bacteria in a wound. The debridement procedure introduces a potential risk that surface bacteria may be introduced deeper into the body, causing infection.

Bacteria typically encountered in a burn wound include *E. coli, P. aeruginosa, S. aureus*, and *C. albicans* (Heggers, J. P., Treatment of infection in burns, H. DN, Editor. 1996, WB Saunders: London. p. 98-135). All of these microbes are killed by one or more of the β-defensin antimicrobial peptides.

Some β-defensin family members are upregulated in response to inflammatory stimuli or bacterial invasion. Others remain non-responsive, downregulated or suppressed in response to inflammatory stimuli or bacterial exposure. In unwounded, intact skin, the calculated epidermal concentrations of β-defensin peptides are well within the range needed for their antimicrobial effects. The β-defensins possess chemotactic activity for immature dendritic cells and memory T cells. These chemotactic responses require much lower concentrations than required for antimicrobial activity (Yang, D., et al., Science, 1999. 286(5439): p. 525-8). As a result of this cross-talk, the β-defensins are thought to mediate an important link between innate and adaptive immunity. Therefore, the β-defensins appear to play a multifunctional role by promoting both an adaptive immune response and inflammation, while facilitating wound healing through their antimicrobial activity. Adaptive immunity is promoted through the endogenous antimicrobial peptides in healthy human skin and likely provides an effective shield from microbial infection; however, patients with unhealthy or chronic skin wounds would also benefit from boosted local antimicrobial peptide levels.

The hBD-1 gene encodes for a 3.9 kDa basic peptide that was originally identified in hemofiltrates from human patients with end stage renal disease (Bensch, K. W., et al., FEBS Lett, 1995. 368(2): p. 331-5). hBD-1 bactericidal activity is predominantly against gram negative bacteria such as *E. coli* and *P. aeruginosa*. Constitutive hBD-1 expression has been observed in skin from various sites on the body. The overexpression of hBD-1 in immortalized human skin cells (HaCat) is associated with keratinocyte cell differentiation. Overexpression was confirmed to have no effect on proliferating cells. The present invention is not limited to a particular mechanism. Indeed, an understanding of the mechanism is not necessary to practice the present invention. Nonetheless, it is contemplated that β-defensin gene expression is a consequence of differentiation, rather than an inducer of differentiation in keratinocytes (Frye, M., J. Bargon, and R. Gropp, J Mol Med, 2001. 79(5-6): p. 275-82). hBD-1 expression in differentiated keratinocyte cells is inhibited upon exposure to bacteria. The present invention is not limited to a particular mechanism. Indeed, an understanding of the mechanism is not necessary to practice the present invention. Nonetheless, it is contemplated that this result indicates that this factor is an important mediator of the healing process in regenerating epithelia. These studies confirm the upregulation of hBD-1 expression is a result of factors not associated with an inflammatory response. This antimicrobial peptide is not induced by inflammatory cytokines, which is consistent with the lack of cytokine-responsive transcription factor regulatory elements in the hBD-1 5'regulatory sequences.

hBD-2 peptide was originally identified in desquamated squames of psoriatic skin and hBD-2 gene expression has since been identified in normal human keratinocytes (Harder, J., et al., Genomics, 1997. 46(3): p. 472-5). This gene encodes for a 4 kDa basic peptide. Variable endogenous levels of expression have been observed when comparing skin from various sites on the body, with the most prominent expression observed in facial skin and foreskin. Expression is localized to the suprabasal layers and the stratum corneum of intact skin. Low levels of hBD-2 protein have been detected in the cytoplasm of keratinocytes in basal layers of skin tissue. These proteins are believed to be secreted into the cell membrane or intercellular spaces as the cells achieve a suprabasal position in the tissue and eventually concentrate in the dehydrated cells of the stratum corneum. hBD-2 peptide efficiently combats clinical isolates of gram negative bacteria such as *P. aeruginosa* and *E. coli*, while only having a bacteriostatic effect, at high concentrations, on gram positive bacterial strains such as *S. aureus* (Liu, A. Y., et al., J Invest Dermatol, 2002. 118(2): p. 275-81). Studies show that endogenous expression is triggered by inflammatory cytokines as well as exposure to bacteria. Finally, not only does hBD-2 have antimicrobial activity, it also modulates the inflammatory response in various skin conditions (Garcia, J. R., et al., Cell Tissue Res, 2001. 306(2): p. 257-64).

The hBD-3 gene encodes for a 5 kDa basic peptide that was identified by screening genomic sequences for antimicrobial activity and the ability to activate monocytes. The gene was cloned from differentiated respiratory epithelial cells. Strongest expression has been exhibited in the skin and tonsil. Endogenous expression is triggered by inflammation, and therefore, hBD-3 is not constitutive but rather a readily inducible antimicrobial peptide. This peptide is also a potent chemoattractant for monocytes and neutrophils, which are strongly involved in the innate immune response (Garcia, J. R., et al., Cell Tissue Res, 2001. 306(2): p. 257-64). hBD-3 possesses a broad spectrum antimicrobial peptide activity at low micromolar concentrations, against many potential pathogenic microbes including *P. aeruginosa*, *S. pyrogenes*, multiresistant *S. aureus*, vancomycin-resistant *E. faecium*, and the yeast *C. albicans*. hBD-3 gene expression is also induced in HaCat and cultured skin-derived keratinocytes when stimulated with heat-inactivated bacteria (Harder, J., et al., Nature, 1997. 387(6636): p. 861). It is speculated that some disorders of defective innate immunity, such as unexplained recurrent infections of particular organs, may be caused by abnormalities that reduce expression of one or more genes that encode defensins or other antimicrobial peptides. Synthetic hBD-3 protein exhibits a strong antimicrobial activity against gram-negative and gram-positive bacteria and fungi.

The present invention contemplates that the overexpression of exogenous antimicrobial polypeptides in human skin equivalents speeds wound healing and prevents infection of the wound. In some preferred embodiments, the antimicrobial polypeptide is overexpressed in the human skin equivalent is human beta defensins 1, 2, or 3 or combinations thereof.

The present invention is not limited to the expression of any particular exogenous antimicrobial polypeptide in the human skin equivalents. Indeed, the expression of a variety of antimicrobial polypeptides is contemplated, including, but not limited to the following: following: magainin (e.g., magainin I, magainin II, xenopsin, xenopsin precursor fragment, caerulein precursor fragment), magainin I and II analogs (PGLa, magainin A, magainin G, pexiganin, Z-12, pexigainin acetate, D35, MSI-78A, MG0 [K10E, K11E, F12W-magainin 2], MG2+ [K10E, F12W-magainin-2], MG4+ [F12W-magainin 2], MG6+ [f12W, E19Q-magainin 2 amide], MSI-238, reversed magainin II analogs [e.g., 53D, 87-ISM, and A87-ISM], Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME(1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 [(+/−) 1-(4-aminobutyl)-6-benzylindane], PM2c [(+/−)-6-benzyl-1-(3-carboxypropyl)indane], PM3 [(+/−) 1-benzyl-6-(4-aminobutyl) indane], tachyplesin, buforin I or II, misgurin, melittin, PR-39, PR-26, 9-phenylnonylamine, (KLAKKLA)n (SEQ ID NO: 124), (KLAKLAK)n (SEQ ID NO: 125), where n=1, 2, or 3, (KALKALK)n (SEQ ID NO: 126), (KLGKKLG)n (SEQ ID NO: 127), and (KAAKKAA)n (SEQ ID NO: 128), wherein n=1, 2, or 3, (paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG1, 1bAMP, snakin, lipid transfer proteins, and plant defensins. Exemplary sequences for the above compounds are provided in Table 1. In some embodiments, the antimicrobial peptides are synthesized from L-amino acids, while in other embodiments, the peptides are synthesized from or comprise D-amino acids.

In some preferred embodiments of the present invention, the antimicrobial polypeptide is a defensin. In certain embodiments, the defensin comprises the following consensus sequence: (SEQ ID NO:107—$X_1CN_1CRN_2CN_3ERN_4CN_5GN_6CCX_2$, wherein N and X represent conservatively or nonconservatively substituted amino acids and $N_1=1$, $N_2=3$ or 4, $N_3=3$ or 4, $N_4=1$, 2, or 3, $N_6=5-9$, $X_1$ and $X_2$ may be present, absent, or equal from 1-2.

In certain embodiments, mutant defensins are utilized in the methods and compositions of the present invention. For example, in some embodiments, disulfide bond formation in beta-defensin 3 is disrupted by mutation of one or more cysteine residues. In preferred embodiments, 5 of the 6 cysteine residues (e.g., $Cys_{40}$, $Cys_{45}$, $Cys_{55}$, $Cys_{62}$, and $Cys_{63}$) are mutated to alanine or other uncharged amino acid not capable of forming disulfide bonds. The present invention is not limited to a particular mechanism. Indeed, an understanding of the mechanism is not necessary to practice the present invention. Nonetheless, it is contemplated that disruption of disulfide bond formation in beta-defensin 3 increases the antimicrobial activity of the protein (See e.g., Hoover et al., Antimicrobial agent and chemotherapy 47:2804 (2003) and Wu et al., PNAS 100:8880 (2003)). The hBD-3 mutants of the present invention may have altered (e.g., greater or less) antimicrobial activity than wild type hBD-3 or they may have similar antimicrobial activity. It is further contemplated that the disruption of disulfide bonds reduces or eliminates the ability of hBD-3 to elicit a chemotactic response. The elimination of chemotactic response may be desirable for avoidance of immune response to skin equivalents grafted onto hosts (e.g., human hosts).

In other embodiments, glycine to alanine substitutions are generated in hBD-3 (e.g., Gly38Ala). In some embodiments, the both Gly-Ala and Cys-Ala substitutions are generated in the same hBD-3 polypeptide.

In some embodiments, antimicrobial polypeptides are modified to include a secretion signal peptide at the N-terminus of the antimicrobial peptides to create a chimeric (hybrid) protein. It is contemplated that such signal sequences allow for the free secretion of antimicrobial peptides, rather than facilitating their association with the cell surface. The antimicrobial peptides have an endogenous signal secretion peptide that directs the immature peptide to the golgi apparatus and eventual secretion into intracellular spaces. These peptides appear to be tightly associated with the cell surfaces, and not "freely" secreted. In some embodiments, the IL-2 Signal secretion peptide is used (CTT GCA CTT GTC ACA AAC AGT GCA CCT; SEQ ID NO:108).

In other embodiments, the antimicrobial polypeptide is a human cathelicidin (hCAP18) polypeptide (SEQ ID NO:47).

The present invention is not limited to any particular antimicrobial peptide. Indeed, media comprising a variety of antimicrobial polypeptides are contemplated. Representative antimicrobial polypeptides are provided in Table 1 below.

TABLE 1

Antimicrobial Peptides

| SEQ ID NO: | Name | Organism | Sequence |
|---|---|---|---|
| 13 | beta-defensin 1 | Human | MRTSYLLLFTLCLLLSEMASGGNFLTGLGHR SDHYNCVSSGGQCLYSACPIFTKIQGTCYRG KAKCCK |
| 14 | beta-defensin 2 | Human | MRVLYLLFSFLFIFLMPLPGVFGGIGDPVTCL KSGAICHPVFCPRRYKQIGTCGLPGTKCCKK P |
| 15 | beta-defensin 3 | Human | MRIHYLLFALLFLFLVPVPGHGGIINTLQKYY CRVRGGRCAVLSCLPKEEQIGKCSTRGRKCC RRKK |
| 16 | lingual antimicrobial peptide precursor (Magainin) | Bos taurus | mrlhhlllallflvlsagsgftqgvrnsqscrrnkgicvp ircpgsmrqigtclgaqvkccrrk |
| 17 | antimicrobial peptide PGQ | Xenopus laevis | Gvlsnvigylkklgtgalnavlkq |
| 18 | Xenopsin | Xenopus laevis | mykgiflcvllavicanslatpssdadedndeveryvrgw askigqtlgkiakvglkeliqpkreamlrsaeaqgkrpwil |
| 19 | magainin precursor | Xenopus laevis | mfkglficsliavicanalpqpeasadedmderevrgigk flhsagkfgkafvgeimkskrdaeavgpeafadedldere vrgigkflhsakkfgkafvgeimnskrdaeavgpeafade dlderevrgigkflhsakkfgkafvgeimnskrdaeavgp eafadedlderevrgigkflhsakkfgkafvgeimnskrd aeavgpeafadedfderevrgigkflhsakkfgkafvgei mnskrdaeavgpeafadedlderevrgigkflhsakkfgk afvgeimnskrdaeavddrrwve |
| 20 | tachyplesin I | Tachypleus gigas | kwcfrvcyrgicyrrcr |
| 21 | tachyplesin II | Tachypleus gigas | rwcfrvcyrgicyrkcr |
| 22 | buforin I | Bufo bufo gagarizans | msgrgkqggkvrakaktrssraglqfpvgrvhrllrkgny aqrvgagapvylaavleyltaeilelagnaardnkktrii prhlqlavrndeelnkllggvtiaqggvlpniqavllpkt esskpaksk |
| 23 | buforin II | Bufo bufo gagarizans | trssraglqfpvgrvhrllrk |
| 24 | cecropin A | Bombyx mori | mnfvrilsfvfalvlalgavsaapeprwkftkkiekvgrn vrdglikagpaiavigqakslgk |
| 25 | cecropin B | Bombyx mori | mnfakilsfvfalvlalsmtsaapeprwkifkkiekmgrn irdgivkagpaievlgsakaigk |
| 26 | cecropin C | Drosophila melanogaster | mnfykifvfvalilaisigqseagwlkklgkrierigqht rdatiqglgiaqqaanvaatarg |
| 27 | cecropin P1 | Sus scrofa | swlsktakklensakkrisegiaiaiqggpr |
| 28 | Indolicidin | Bos taurus | ilpwkwpwwpwrr |

TABLE 1-continued

Antimicrobial Peptides

| SEQ ID NO: | Name | Organism | Sequence |
|---|---|---|---|
| 29 | Nisin | Lactococcus lactis | itsislctpgcktgalmgcnmktatchcsihvsk |
| 30 | Ranalexin | Rana catesbeiana | flgglikivpamicavtkkc |
| 31 | lactoferricin B | Bos taurus | fkcrrwqwrmkklgapsitcvrraf |
| 32 | Protegrin-1 | Sus scrofa | rggrlcycrrrfcvcvgrx |
| 33 | Protegrin-2 | Sus scrofa | ggrlcycrrrfcicvg |
| 34 | histatin precursor | Homo sapiens | mkffvfalilalmlsmtgadshakrhhgykrkfhekhhsh rgyrsnylydn |
| 35 | histatin 1 | Macaca fascicularis | dsheerhhgrhghhkygrkfhekhhshrgyrsnylydn |
| 36 | dermaseptin | Phyllomedusa sauvagei | alwktmlkklgtmalhagkaalgaaadtisqtq |
| 37 | dermaseptin 2 | Phyllomedusa sauvagei | alwftmlkklgtmalhagkaalgaaantisqgtq |
| 38 | dermaseptin 3 | Phyllomedusa sauvagei | alwknmlkgigklagkaalgavkklvgaes |
| 39 | Misgurin | Misgurnus anguillicaudatus | rqrveelskfskkgaaarrrk |
| 40 | Melittin | Apis mellifera | gigavlkvlttglpaliswisrkkrqq |
| 41 | pardaxin-1 | Pardachirus pavoninus | gffalipkiisspflftlllsavgsalsssgeqe |
| 42 | pardaxin-2 | Pardachirus pavoninus | gffalipkiisspifltlllsavgsalsssgqe |
| 43 | Bactenecin 5 precursor | Bos taurus | metqraslslgrcslwlllglvlpsasaqalsyreavlr avdqfnersseanlyrlleldptpnddldpgtrkpvsfrv ketdcprtsqqpleqcdfkenglvkqcvgtvtldpsndqf dincnelqsvrfrppirrppirppfyppfrppirppifpp irppfrpplgpfpgrr |
| 44 | bactenecin precursor | Bos taurus | metpraslslgrwslwlllllglalpsasaqalsyreavlr avdqlneqssepniyrlleldqppqddedpdspkrvsfrv ketvcsrttqqppeqcdfkengllkrcegtvtldqvrgnf ditcnnhqsiritkqpwappqaarlcrivvirvcr |
| 45 | ceratotoxin A | Ceratitis capitata | sigsalkkalpvakkigkialpiakaalp |
| 46 | ceratotoxin B | Ceratitis capitata | sigsafkkalpvakkigkaalpiakaalp |
| 47 | cathelicidin antimicrobial peptide | Homo sapiens | mktqrnghslgrwslvlllllglvmplaiiaqvlsykeavl raidginqrssdanlyrlldldprptmdgdpdtpkpvsft vketvcprttqqspedcdtkkdglvkrcmgtvtlnqargs fdiscdkdnkrfallgdffrkskekigkefkrivqrikdf lrnlvprtes |
| 48 | myeloid cathelicidin 3 | Equus caballus | metqrntrclgrwspllllllglvippattqalsykeavlr avdglnqrssdenlyrlleldplpkgdkdsdtpkpvsfmv ketvcprimkqtpeqcdfkenglvkqcvgtvildpvkdyf dascdepqrvkrfhsvgsliqrhqqmirdkseatrhgiri itrpkllllas |
| 49 | myeloid antimicrobial peptide BMAP-28 | Bos taurus | metqraslslgrwslwlllllglalpsasaqalsyreavlr avdqlnekssseanlyrlleldpppkeddenpnipkpvsfr vketvcprtsqqspeqcdfkengllkecvgtvtldqvgsn fditcavpqsvggllrslgrkilrawkkygpiivpiirig |
| 50 | myeloid cathelicidin 1 | Equus caballus | metqrntrclgrwspllllllglvippattqalsykeavlr avdglnqrssdenlyrlleldplpkgdkdsdtpkpvsfmv |

TABLE 1-continued

Antimicrobial Peptides

| SEQ ID NO: | Name | Organism | Sequence |
|---|---|---|---|
| | | | ketvcprimkqtpeqcdfkenglvkqcvgtvilgpvkdhf dvscgepqrvkrfgrlaksflrmrillprrkillas |
| 51 | SMAP 29 | Ovis aries | metqraslslgrcslwllllglalpsasaqvlsyreavlr aadqlneksseanlyrllleldpppkqddensnipkpvsfr vketvcprtsqqpaeqcdfkengllkecvgtvtldqvrnn fditcaepqsvrglrrlgrkiahgvkkygptvlriiriag |
| 52 | BNP-1 | Bos taurus | rlcrivvirvcr |
| 53 | HNP-1 | Homo sapiens | acycripaciagerrygtciyqgrlwafcc |
| 54 | HNP-2 | Homo sapiens | cycripaciagerrygtciyqgrlwafcc |
| 55 | HNP-3 | Homo sapiens | dcycripaciagerrygtciyqgrlwafcc |
| 56 | HNP-4 | Homo sapiens | vcscrlvfcrrtelrvgncliggvsftycctrv |
| 57 | NP-1 | Oryctolagus cuniculus | vvcacrralclprerragfcrirgrihplccrr |
| 58 | NP-2 | Oryctolagus cuniculus | vvcacrralclplerragfcrirgrihplccrr |
| 59 | NP-3A | Oryctolagus cuniculus | gicacrrrfcpnserfsgycrvngaryvrccsrr |
| 60 | NP-3B | Oryctolagus cuniculus | grcvcrkqllcsyrerrigdckirgvrfpfccpr |
| 61 | NP-4 | Oryctolagus cuniculus | vsctcrrfscgfgerasgsctvnggvrhtlccrr |
| 62 | NP-5 | Oryctolagus cuniculus | vfctcrgflcgsgerasgsctingvrhtlccrr |
| 63 | RatNP-1 | Rattus norvegicus | vtcycrrtrcgfrerlsgacgyrgriyrlccr |
| 64 | Rat-NP-3 | Rattus norvegicus | cscrysscrfgerllsgacrlngriyrlcc |
| 65 | Rat-NP-4 | Rattus norvegicus | actcrigacvsgerltgacglngriyrlccr |
| 66 | GPNP | Guinea pig | rrcicttrtcrfpyrrlgtcifqnrvytfcc |
| 67 | theta defensin-1 | Macaca mulatta | rcictrgfcrclcrrgvc |
| 68 | defensin CUA1 | Helianthus annuus | mkssmkmfaallllvvmcllanemggplvveartcesqshk fkgtclsdtncanvchserfsggkcrgfrrrcfctthc |
| 69 | defensin SD2 | Helianthus annuus | mkssmkmfaallllvvmcllanemggplvveartcesqshk fkgtclsdtncanvchserfsggkcrgfrrrcfctthc |
| 70 | neutrophil defensin 2 | Macaca mulatta | acycripaclagerrygtcfymgrvwafcc |
| 71 | 4 KDA defensin | Androctonus australis hector | gfgcpfnqgachrhcrsirrrggycaglflqtctcyr |
| 72 | defensin | Mytilus galloprovincialis | gfgcpnnyqchrhcksipgrcggycggxhrlrctcyrc |
| 73 | defensin AMP1 | Heuchera sanguinea | dgvklcdvpsgtwsghcgssskcsqqckdrehfayggach yqfpsvkcfckrqc |
| 74 | defensin AMP1 | Clitoria ternatea | nlcerasltwtgncgntghcdtqcrnwesakhgachkrgn wkcfcyfnc |
| 75 | cysteine-rich cryptdin-1 homolog | Mus musculus | mkklvllfalvllafqvqadsiqntdeetkteeqpgekdq avsvsfgdpqgsalqdaalgwgrrcpqcprcpscpscprc prcprckcnpk |

TABLE 1-continued

Antimicrobial Peptides

| SEQ ID NO: | Name | Organism | Sequence |
|---|---|---|---|
| 76 | beta-defensin-9 | Bos taurus | qgvrnfvtcrinrgfcvpircpghrrqigtclgpqikccr |
| 77 | beta-defensin-7 | Bos taurus | qgvrnfvtcrinrgfcvpircpghrrqigtclgprikccr |
| 78 | beta-defensin-6 | Bos taurus | qgvrnhvtcriyggfcvpircpgrtrqigtcfgrpvkccrrw |
| 79 | beta-defensin-5 | Bos taurus | qvvrnpqscrwnmgvcipiscpgnmrqigtcfgprvpccr |
| 80 | beta-defensin-4 | Bos taurus | qrvrnpqscrwnmgvcipflcrvgmrqigtcfgprvpccrr |
| 81 | beta-defensin-3 | Bos taurus | qgvrnhvtcrinrgfcvpircpgrtrqigtcfgprikccrsw |
| 82 | beta-defensin-10 | Bos taurus | qgvrsylscwgnrgiclnrcpgrmrqigtclaprvkccr |
| 83 | beta-defensin-13 | Bos taurus | sgisgplscgrnggvcipircpvpmrqigtcfgrpvkccrsw |
| 84 | beta-defensin-1 | Bos taurus | dfaschtnggiclpnrcpghmiqigicfrprvkccrsw |
| 85 | coleoptericin | Zophobas atratus | slqggapnfpqpsqqnggwqvspdlgrddkgntrgqieiq nkgkdhdfnagwgkvirgpnkakptwhvggtyrr |
| 86 | defensin C | Aedes aegypti | atcdllsgfgvgdsacaahciargnrggycnskkvcvcrn |
| 87 | defensin B | Mytilus edulis | gfgcpndypchrhcksipgryggycggxhrlrctc |
| 88 | sapecin C | Sarcophaga peregrina | atcdllsgigvqhsacalhcvfrgnrggyctgkgicvcrn |
| 89 | macrophage antibiotic peptide MCP-1 | Oryctolagus cuniculus | mrtlallaaillvalqaqaehvsvsidevvdqqppqaedq dvaiyvkehessalealgvkagvvcacrralclprerrag fcrirgrihplccrr |
| 90 | cryptdin-2 | Mus musculus | mkplvllsalvllsfqvqadpiqntdeetkteeqsgeedq avsvsfgdregaslqeeslrdlvcycrtrgckrrermngt crkghlmytlcc |
| 91 | cryptdin-5 | Mus musculus | mktfvllsalvllafqvqadpihktdeetnteeqpgeedq avsisfggqegsalheelskklicycrirgckrrervfgt crnlfltfvfccs |
| 92 | cryptdin 12 | Mus musculus | lrdlvcycrargckgrermngtcrkghllymlccr |
| 93 | defensin | Pyrrhocoris apterus | atcdilsfqsqwvtpnhagcalhcvikgykggqckitvchcrr |
| 94 | defensin R-5 | Rattus norvegicus | vtcycrstrcgfrerlsgacgyrgriyrlccr |
| 95 | defensin R-2 | Rattus norvegicus | vtcscrtsscrfgerlsgacrlngriyrlcc |
| 96 | defensin NP-6 | Oryctolagus cuniculus | gicacrrrfclnfeqfsgycrvngaryvrccsrr |
| 97 | beta-defensin-2 | Pan troglodytes | mrvlyllfsflfiflmplpgvfggisdpvtclksgaichp vfcprrykqigtcglpgtkccкkp |
| 98 | beta-defensin-1 | Capra hircus | mrlhhlllvlfflvlsagsgftqgirsrrschrnkgvcal trcprnmrqigtcfgppvkccrkk |
| 99 | beta defensin-2 | Capra hircus | mrlhhlllalfflvlsagsgftqgiinhrscyrnkgvcap arcprnmrqigtchgppvkccrkk |
| 100 | defensin-3 | Macaca mulatta | mrtlvilaaillvalqaqaeplqartdeataaqeqiptdn pevvvslawdeslapkdsvpglrknmacycripaclager rygtcfyrrrvwafcc |
| 101 | defensin-1 | Macaca mulatta | mrtlvilaaillvalqaqaeplqartdeataaqeqiptdn pevvvslawdeslapkdsvpglrknmacycripaclager rygtcfylgrvwafcc |
| 102 | neutrophil defensin 1 | Mesocricetus auratus | vtcfcrrrgcasrerhigycrfgntiyrlccrr |

TABLE 1-continued

Antimicrobial Peptides

| SEQ ID NO: | Name | Organism | Sequence |
|---|---|---|---|
| 103 | neutrophil defensin 1 | *Mesocricetus auratus* | cfckrpvcdsgetqigycrlgntfyrlccrq |
| 104 | Gallinacin 1-alpha | *Gallus gallus* | grksdcfrkngfcaflkcpyltlisgkcsrfhlcckriw |
| 105 | defensin | *Allomyrina dichotoma* | vtcdllsfeakgfaanhslcaahclaigrrggscergvcicrr |
| 106 | neutrophil cationic peptide 1 | *Cavia porcellus* | rrcicttrtcrfpyrrlgtcifqnrvytfcc |

Accordingly, in some embodiments the present invention contemplates the production of keratinocytes and skin equivalents expressing an antimicrobial polypeptide, and compositions and methods for making keratinocytes expressing an exogenous antimicrobial polypeptide. In preferred embodiments, the antimicrobial polypeptide is a defensin or a cathelicidin. In still more preferred embodiments, the defensin is a human beta defensin. In still more preferred embodiments, the human beta defensin is human beta defensin 1, 2 or 3. In some embodiments, the keratinocytes are transfected with more than one defensin selected from the group consisting of human beta-defensin 1, 2 or 3. In preferred embodiments, keratinocytes are induced to express an antimicrobial polypeptide through transfection with an expression vector comprising a gene encoding an antimicrobial polypeptide. An expression vector comprising a gene encoding an antimicrobial polypeptide can be produced by operably linking an antimicrobial polypeptide coding sequence to one or more regulatory sequences such that the resulting vector is operable in a desired host.

In preferred embodiments, the antimicrobial polypeptide is isolated from a DNA source, cloned, sequenced, and incorporated into a selection vector. In certain embodiments, isolation of the antimicrobial polypeptide DNA occurs via PCR by using primer sequences designed to amplify the antimicrobial polypeptide sequence. Primer sequences specific for the desired antimicrobial polypeptide may be obtained from Genbank. Amplification of a DNA source with such primer sequences through standard PCR procedures results in antimicrobial polypeptide cDNA isolation. In preferred embodiments, the source of cDNA is human cDNA.

D) Methods of Generating Host Cells Expressing Exogenous Polypeptides

In some embodiments, the present invention provides methods of generating host cells (e.g., keratinocytes) and skin equivalents expressing one or more exogenous polypeptides (e.g., KGF-2 and/or antimicrobial polypeptides. The present invention is not limited to particular methods for the generation of such cells and skin equivalents. Exemplary methods are described below. Additional methods are known to those skilled in the relevant arts.

In certain embodiments, the antimicrobial polypeptide cDNA is cloned into a cloning vector. A regulatory sequence that can be linked to the antimicrobial polypeptide DNA sequence in an expression vector is a promoter that is operable in the host cell in which the antimicrobial polypeptide is to be expressed. Optionally, other regulatory sequences can be used herein, such as one or more of an enhancer sequence, an intron with functional splice donor and acceptance sites, a signal sequence for directing secretion of the defensin, a polyadenylation sequence, other transcription terminator sequences, and a sequence homologous to the host cell genome. Other sequences, such as origin of replication, can be added to the vector as well to optimize expression of the desired defensin. Further, a selectable marker can be present in the expression vector for selection of the presence thereof in the transformed host cells.

In preferred embodiments, antimicrobial polypeptide is fused to a regulatory sequence that drives the expression of the polypeptide (e.g., a promoter). In preferred embodiments, the regulatory sequence is the involucrin promoter (SEQ ID NO: 12) or the keratin-14 promoter. However, any promoter that would allow expression of the antimicrobial polypeptide in a desired host can be used in the present invention. Mammalian promoter sequences that can be used herein are those from mammalian viruses that are highly expressed and that have a broad host range. Examples include the SV40 early promoter, the Cytomegalovirus ("CMV") immediate early promoter mouse mammary tumor virus long terminal repeat ("LTR") promoter, adenovirus major late promoter (Ad MLP), and Herpes Simplex Virus ("HSV") promoter. In addition, promoter sequences derived from non-viral genes, such as the murine metallothionein gene, ubiquitin and elongation factor alpha (EF-1α) are also useful herein. These promoters can further be either constitutive or regulated, such as those that can be induced with glucocorticoids in hormone-responsive cells.

In some preferred embodiments, host cells (e.g., keratinocytes cells) expressing KGF-2 or antimicrobial polypeptides can be produced by conventional gene expression technology, as discussed in more detail below. The practice of the present invention will employ, unless otherwise indicated, conventional techniques of molecular biology, microbiology, recombinant DNA, and immunology, which are within the skill of the art.

Such techniques are explained fully in the literature, including Sambrook, et al., MOLECULAR CLONING: A LABORATORY MANUAL 2nd ed. (Cold Spring Harbor Laboratory Press, 1989); DNA CLONING, Vol. I and II, D. N Glover ed. (IRL Press, 1985); OLIGONUCLEOTIDE SYNTHESIS, M. J. Gait ed. (IRL Press, 1984); NUCLEIC ACID HYBRIDIZATION, B. D. Hames & S. J. Higgins eds. (IRL Press, 1984); TRANSCRIPTION AND TRANSLATION, B. D. Hames & S. J. Higgins eds., (IRL Press, 1984); ANIMAL CELL CULTURE, R. I. Freshney ed. (IRL Press, 1986); IMMOBILIZED CELLS AND ENZYMES, K. Mosbach (IRL Press, 1986); B. Perbal, A PRACTICAL GUIDE TO MOLECULAR CLONING, Wiley (1984); the series, METHODS IN ENZYMOLOGY, Academic Press, Inc.; GENE TRANSFER VECTORS FOR MAMMALIAN CELLS, J. H. Miller and M. P. Calos eds. (Cold Spring Harbor Laboratory, 1987); METHODS IN ENZYMOLOGY, Vol. 154 and 155, Wu and Grossman, eds., and Wu, ed., respectively (Academic Press, 1987), IMMUNOCHEMICAL METHODS IN CELL AND MOLECULAR BIOLOGY, R. J. Mayer and J. H. Walker, eds. (Academic Press London, Harcourt Brace U.S., 1987), PROTEIN PURIFICATION: PRINCIPLES AND PRACTICE, 2nd ed. (Springer-Verlag, N.Y. (1987), and HANDBOOK OF EXPERIMENTAL IMMUNOLOGY, Vol. I-IV, D. M. Weir et al., (Blackwell Scientific Publications, 1986); Kitts et al., Biotechniques 14:810-817 (1993); Munemitsu et al., Mol. and Cell. Biol. 10:5977-5982 (1990).

The present invention contemplates keratinocytes and skin equivalents expressing KGF-2 and/or antimicrobial polypeptides, and compositions and methods for making such cells. In some embodiments, host cells are induced to express exogenous polypeptides through transfection with an expression vector containing DNA encoding the exogenous polypeptide. An expression vector containing KGF-2 DNA can be produced by operably linking KGF-2 to one or more regulatory sequences such that the resulting vector is operable in a desired host. Cell transformation procedures suitable for use herein are those known in the art and include, for example with mammalian cell systems, dextran-mediated transfection, calcium phosphate precipitation, polybrene-mediated transfection, protoplast fusion, electroporation, encapsulation of the exogenous polynucleotide in liposomes, and direct microinjection of the DNA into nuclei. In preferred embodiments, cells are transfected with a pUB-Bsd expression vector containing exogenous DNA (e.g., KGF-2 and antimicrobial polypeptides) operably linked to promoter (e.g., K14 or involucrin) DNA.

Immunoassays and activity assays that are known in the art can be utilized herein to determine if the transformed host cells are expressing the desired exogenous polypeptide (e.g., KGF-2 and antimicrobial polypeptides). In some embodiments, detection of intracellular production of KGF-2 or antimicrobial polypeptides by transformed host cells is accomplished with an immunofluorescence assay. In preferred embodiments, detection of intracellular production of exogenous polypeptides by transformed host cells is accomplished through a RT-PCR screen. In further embodiments, detection of secreted or extracellular production of KGF-2 or antimicrobial polypeptides by transformed host cells is accomplished through a direct ELISA screen. In some embodiments, the KGF-2 or antimicrobial polypeptide is detected by Western blotting.

In other embodiments, expression vectors comprising exogenous polypeptides are introduced directly into tissues (e.g., human skin equivalents). Expression vectors may be introduced into tissues using any suitable technique including, but not limited to, electroporation, particle bombardment (e.g., U.S. Pat. Nos. 6,685,669, 6,592,545, and 6,004,286; each of which is herein incorporated by reference) and transfection.

II. Selection of Cells by Electroporation

Experiments conducted during the course of development of the present invention (See e.g., Example 26) resulted in the identification of a novel technique for the selection of cells within a population. The experiments demonstrated that cells electroporated in the presence or absence of exogenous nucleic acid and selection demonstrated properties of multipotency. Accordingly, in some embodiments, the present invention provides methods of selecting for cells in a population having desired growth and proliferation properties.

In some embodiments, electroporation is used to select for cells with enhanced pluripotency or multipotency. In other embodiments, electroporation is used to select for cells with enhanced pluripotency or multipotency. As used herein, the term "pluripotent" means the ability of a cell to differentiate into the three main germ layers: endoderm, ectoderm, and mesoderm. In some embodiments, the cells with enhanced pluripotency or multipotency exhibit stem cells like properties.

For example, in some embodiments, electroporation is used to select for cells with stem-cell like properties. Stem cells are undifferentiated cells that can give rise to a succession of mature functional cells. Stem cells can by embryonically derived (See e.g., U.S. Pat. Nos. 5,843,780 and 6,200,806; each of which is herein incorporated by reference) or derived from adult cells. Examples of adult stem cells include hematopoietic stem cells, neural stem cells, mesenchymal stem cells, and bone marrow stromal cells. These stem cells have demonstrated the ability to differentiate into a variety of cell types including adipocytes, chondrocytes, osteocytes, myocytes, bone marrow stromal cells, and thymic stroma (mesenchymal stem cells); hepatocytes, vascular cells, and muscle cells (hematopoietic stem cells); myocytes, hepatocytes, and glial cells (bone marrow stromal cells) and, cells from all three germ layers (adult neural stem cells).

In other embodiments, electroporation is used to select for cells with extended proliferative capacity. For example, experiments conducted during the course of development of the present invention demonstrated that electroporated cells were typically the larger surviving colonies.

In yet other embodiments, electroporation is used to select for keratinocytes having holoclone or meroclone cell morphology (e.g., a colony morphology of tightly packed, uniform cells, smooth colony edges, overall round colony morphology).

III. Treatment of Wounds with Keratinocytes Cells Transfected with Exogenous Polypeptides Successful treatment of chronic skin wounds (e.g., venous ulcers, diabetic ulcers, pressure ulcers) is a serious problem. The healing of such a wound often times takes well over a year of treatment. Treatment options currently include dressings and debridement (use of chemicals or surgery to clear away necrotic tissue), and/or antibiotics in the case of infection. These treatment options take extended periods of time and high amounts of patient compliance. As such, a therapy that can increase a practioner's success in healing chronic wounds and accelerate the rate of wound healing would meet an unmet need in the field.

In some embodiments, the present invention contemplates treatment of skin wound with keratinocytes and skin equivalents expression exogenous antimicrobial and/or KGF-2 polypeptides.

KGF-2 is associated with skin wound healing. In skin, KGF-2 is naturally expressed in the dermal compartment. Topical application of KGF-2 to skin wounds increases dermal cell proliferation. In addition, KGF-2 manifests strong mitogenic activity in dermal cells and stimulates granulation tissue formation in full thickness excisional wounds. KGF-2 accelerated wound closure is transient and does not cause scar formation after complete wound healing (Yu-Ping et al. 1999). Local protein administration, however, has been shown to be ineffective due to enzymes and proteases in the wound fluid (Jeschke et al. 2002). KGF-2 selectively induces normal epithelial cell proliferation, differentiation and migration, while having no in vitro or in vivo proliferative effects on KGFR (+) human epithelial-like tumors. (Alderson et al.

2002). As such, KGF-2 is an attractive candidate for therapeutic use to enhance wound healing.

The present invention contemplates treatment of skin wounds with keratinocytes or skin equivalents expressing KGF-2 and/or antimicrobial polypeptides. In some embodiments, cells expressing KGF-2 and/or antimicrobial polypeptides are topically applied to wound sites. In some embodiments, the keratinocytes are applied via a spray, while in other embodiments, the keratinocytes are applied via a gel. In other embodiments, cells expressing KGF-2 and/or antimicrobial polypeptides are used for engraftment on partial thickness wounds. In other embodiments, cells expressing KGF-2 and/or antimicrobial polypeptides are used for engraftment on full thickness wounds. In other embodiments, cells expressing KGF-2 and/or antimicrobial polypeptides are used to treat numerous types of internal wounds, including, but not limited to, internal wounds of the mucous membranes that line the gastrointestinal tract, ulcerative colitis, and inflammation of mucous membranes that may be caused by cancer therapies. In still other embodiments, cells expressing KGF-2 and/or antimicrobial polypeptides are used as a temporary or permanent wound dressing.

Cells expressing KGF-2 and/or antimicrobial polypeptides find use in wound closure and burn treatment applications. The use of autografts and allografts for the treatment of burns and wound closure is described in Myers et al., A. J. Surg. 170(1):75-83 (1995) and U.S. Pat. Nos. 5,693,332; 5,658,331; and 6,039,760, each of which is incorporated herein by reference. In some embodiments, the skin equivalents may be used in conjunction with dermal replacements such as DERMAGRAFT. In other embodiments, the skin equivalents are produced using both a standard source of keratinocytes (e.g., NIKS cells) and keratinocytes from the patient that will receive the graft. Therefore, the skin equivalent contains keratinocytes from two different sources. In still further embodiments, the skin equivalent contains keratinocytes from a human tissue isolate. Accordingly, the present invention provides methods for wound closure, including wounds caused by burns, comprising providing cells expressing KGF-2 and/or antimicrobial polypeptides and a patient suffering from a wound and treating the patient with the cells under conditions such that the wound is closed.

Detailed methods for producing the skin equivalents of the present invention are disclosed in the following Experimental section. However, the present invention is not limited to the production of skin equivalents by the methods. Indeed, a variety of organotypic culture techniques may be used to produce skin equivalents, including those described in U.S. Pat. Nos. 5,536,656 and 4,485,096, both of which are incorporated herein by reference. In some embodiments, different populations of keratinocytes are used to construct the skin equivalent. Accordingly, in some embodiments, the skin equivalents of the present invention are formed from keratinocytes derived from an immortalized cell line (e.g., NIKS cells) and cell derived from a patient. In other embodiments, the skin equivalents of the present invention are formed from at least a first population of keratinocytes derived from an immortalized cell line that express a exogenous antimicrobial polypeptide and/or KGF-2 and a second population of keratinocytes derived from an immortalized cell line that do not express a exogenous antimicrobial polypeptide. It is contemplated that varying the ratio of the two populations the dose of antimicrobial polypeptide and/or KGF-2 delivered can be varied. In still other embodiments, the skin equivalents are formed from at least a first population of keratinocytes expressing a first exogenous antimicrobial polypeptide (e.g., hBD-1) and at least a second population of keratinocytes expressing a second exogenous antimicrobial polypeptide (e.g., hBD-2 or hBD-3). Again, the ratios of the cell populations can be varied to vary the dose. In still other embodiments, the skin equivalents are formed from at least a first population of keratinocytes expressing a first exogenous antimicrobial polypeptide (e.g., hBD-1), at least a second population of keratinocytes expressing a second exogenous antimicrobial polypeptide (e.g., hBD-2 or hBD-3), and keratinocytes derived from a patient.

In a further embodiment, the KGF-2 and/or antimicrobial polypeptide or a conjugate thereof can be mixed with a pharmaceutically acceptable carrier to produce a therapeutic composition that can be administered for therapeutic purposes, for example, for wound healing, and for treatment of hyperproliferative diseases of the skin and tumors, such as psoriasis and basal cell carcinoma.

In still further embodiments, the cells expressing KGF-2 and/or antimicrobial polypeptides are engineered to provide a therapeutic agent to a subject. The present invention is not limited to the delivery of any particular therapeutic agent. Indeed, it is contemplated that a variety of therapeutic agents may be delivered to the subject, including, but not limited to, enzymes, peptides, peptide hormones, other proteins, ribosomal RNA, ribozymes, and antisense RNA. These therapeutic agents may be delivered for a variety of purposes, including but not limited to the purpose of correcting genetic defects. In some particular preferred embodiments, the therapeutic agent is delivered for the purpose of detoxifying a patient with an inherited inborn error of metabolism (e.g., aminoacidopathesis) in which the graft serves as wild-type tissue. It is contemplated that delivery of the therapeutic agent corrects the defect. In some embodiments, the cells expressing KGF-2 and/or antimicrobial polypeptides are transfected with a DNA construct encoding a therapeutic agent (e.g., insulin, clotting factor IX, erythropoietin, etc) and the cells grafted onto the subject. The therapeutic agent is then delivered to the patient's bloodstream or other tissues from the graft. In preferred embodiments, the nucleic acid encoding the therapeutic agent is operably linked to a suitable promoter. The present invention is not limited to the use of any particular promoter. Indeed, the use of a variety of promoters is contemplated, including, but not limited to, inducible, constitutive, tissue specific, and keratinocyte specific promoters. In some embodiments, the nucleic acid encoding the therapeutic agent is introduced directly into the keratinocytes (i.e., by calcium phosphate co-precipitation or via liposome transfection). In other preferred embodiments, the nucleic acid encoding the therapeutic agent is provided as a vector and the vector is introduced into the keratinocytes by methods known in the art. In some embodiments, the vector is an episomal vector such as a plasmid. In other embodiments, the vector integrates into the genome of the keratinocytes. Examples of integrating vectors include, but are not limited to, retroviral vectors, adeno-associated virus vectors, and transposon vectors.

IV. Testing Methods

The host cells and cultured skin tissue of the present invention may be used for a variety of in vitro tests. In particular, the host cells and cultured skin tissue find use in the evaluation of: skin care products, drug metabolism, cellular responses to test compounds, wound healing, phototoxicity, dermal irritation, dermal inflammation, skin corrosivity, and cell damage. The host cells and cultured skin tissue are provided in a variety of formats for testing, including 6-well, 24-well, and 96-well plates. Additionally, the cultured skin tissue can be divided by standard dissection techniques and then tested. The cultured skin tissue of the present invention may have both an epidermal layer with a differentiated stratum corneum and dermal layer that includes dermal fibroblasts. As described above, in preferred embodiments, the epidermal layer is derived from immortalized NIKS cells. Other preferred cell lines, including NIKS cells are characterized by; i) being immortalized; ii) being nontumorigenic; iii) forming cornified envelopes when induced to differentiate; iv) undergoing normal squamous differentiation in organotypic culture; and v) maintaining cell type-specific growth requirements, wherein said cell type-specific growth requirements include 1) exhibition of morphological characteristics of normal human keratinocytes when cultured in standard keratinocyte growth medium in the presence of mitomycin C-treated 3T3 feeder cells; 2) dependence on epidermal growth factor for growth; and 3) inhibition of growth by transforming growth factor β1.

The present invention encompasses a variety of screening assays. In some embodiments, the screening method comprises providing a host cell or cultured skin tissue of the present invention and at least one test compound or product (e.g., a skin care product such as a moisturizer, cosmetic, dye, or fragrance; the products can be in any from, including, but not limited to, creams, lotions, liquids and sprays), applying the product or test compound to the host cell or cultured skin tissue, and assaying the effect of the product or test compound on the host cell or cultured skin tissue. A wide variety of assays are used to determine the effect of the product or test compound on the cultured skin tissue. These assays include, but are not limited to, MTT cytotoxicity assays (Gay, The Living Skin Equivalent as an In Vitro Model for Ranking the Toxic Potential of Dermal Irritants, Toxic. In Vitro (1992)) and ELISA to assay the release of inflammatory modulators (e.g., prostaglandin E2, prostacyclin, and interleukin-1-alpha) and chemoattractants. The assays can be further directed to the toxicity, potency, or efficacy of the compound or product. Additionally, the effect of the compound or product on growth, barrier function, or tissue strength can be tested.

In particular, the present invention contemplates the use of host cells or cultured skin tissue for high throughput screening of compounds from combinatorial libraries (e.g., libraries containing greater than $10^4$ compounds). In some embodiments, the cells are used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, host cells or cultured skin tissue is treated with a compound or plurality of compounds (e.g., from a combinatorial library) and assayed for the presence or absence of a second messenger response. In some preferred embodiments, the cells (e.g., NIKS cells) used to create cultured skin tissue are transfected with an expression vector encoding a recombinant cell surface receptor, ion-channel, voltage gated channel or some other protein of interest involved in a signaling cascade. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, IP3, cAMP, arachidonic acid release) due to stimulation of membrane receptors and ion channels (e.g., ligand gated ion channels; see Denyer et al., Drug Discov. Today 3:323-32 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the cells comprising cultured skin tissue are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75-80 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The host cells and cultured skin tissue of the present invention are also useful in reporter gene assays. Reporter gene assays involve the use of host cells transfected with vectors encoding a nucleic acid comprising transcriptional control elements of a target gene (i.e., a gene that controls the biological expression and function of a disease target or inflammatory response) spliced to a coding sequence for a reporter gene. Therefore, activation of the target gene results in activation of the reporter gene product. This serves as indicator of response such an inflammatory response. Therefore, in some embodiments, the reporter gene construct comprises the 5' regulatory region (e.g., promoters and/or enhancers) of a protein that is induced due to skin inflammation or irritation or protein that is involved in the synthesis of compounds produced in response to inflammation or irritation (e.g., prostaglandin or prostacyclin) operably linked to a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

In other preferred embodiments, the host cells or cultured skin tissue find use for screening the efficacy of drug introduction across the skin or the affect of drugs directed to the skin. In these embodiments, cultured skin tissue or host cells are treated with the drug delivery system or drug, and the permeation, penetration, or retention or the drug into the skin equivalent is assayed. Methods for assaying drug permeation are provided in Asbill et al., Pharm Res. 17(9): 1092-97 (2000). In some embodiments, cultured skin tissue is mounted on top of modified Franz diffusion cells. The cultured skin tissue is allowed to hydrate for one hour and then pretreated for one hour with propylene glycol. A saturated suspension of the model drug in propylene glycol is then added to the cultured skin tissue. The cultured skin tissue can then be sampled at predetermined intervals. The cultured skin tissue is then analyzed by HPLC to determine the concentration of the drug in the sample. Log P values for the drugs can be determined using the ACD program (Advanced Chemistry Inc., Ontario, Canada). These methods may be adapted to study the delivery of drugs via transdermal patches or other delivery modes.

It is contemplated that cultured skin tissue of the present invention is also useful for the culture and study of tumors that occur naturally in the skin as well as for the culture and study of pathogens that affect the skin. Accordingly, in some embodiments, it contemplated that the cultured skin tissue of the present invention is seeded with malignant cells. By way of non-limiting example, the cultured skin tissue can be seeded with malignant SCC13y cells as described in U.S. Pat. No. 5,989,837, which is incorporated herein by reference, to provide a model of human squamous cell carcinoma. These seeded cultured skin tissue can then be used to screen compounds or other treatment strategies (e.g., radiation or tomotherapy) for efficacy against the tumor in its natural environment. Thus, some embodiments of the present invention provide methods comprising providing cultured skin tissue comprising malignant cells or a tumor and at least one test compound, treating the cultured skin tissue with the compound, and assaying the effect of the treatment on the malignant cells or tumors. In other embodiments of the present invention, methods are provided that comprise providing cultured skin tissue comprising malignant cells or a tumor and at least one test therapy (e.g., radiation or phototherapy, treating the cultured skin tissue with the therapy, and assaying the effect of the therapy on the malignant cells or tumors.

In other embodiments, cultured skin tissue is used to culture and study skin pathogens. By way of non-limiting example, cultured skin tissue is infected with human papilloma virus (HPV) such as HPV18. Methods for preparing cultured skin tissue infected with HPV are described in U.S. Pat. No. 5,994,115, which is incorporated herein by reference. Thus, some embodiments of the present invention provide methods comprising providing cultured skin tissue infected with a pathogen of interest and at least one test compound or treatment and treating the cultured skin tissue with the test compound or treatment. In some preferred embodiments, the methods further comprise assaying the effect the test compound or treatment on the pathogen. Such assays may be conducted by assaying the presence, absence, or quantity of the pathogen in the cultured skin tissue following treatment. For example, an ELISA may be performed to detect or quantify the pathogen. In some particularly preferred embodiments, the pathogen is viral pathogen such as HPV.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); °C. (degrees Centigrade); U (units), mU (milliunits); min. (minutes); sec. (seconds); % (percent); kb (kilobase); bp (base pair); PCR (polymerase chain reaction); BSA (bovine serum albumin); Pfu (*Pyrococcus furiosus*).

Example 1

Keratin 14 Promoter Cloning and Characterization

This Example describes the method used to isolate, clone and characterize the K14 promoter DNA. Primer sequences were designed based on the published K14 Promoter sequence available at Genbank (Genbank Accession #U11076). In order to amplify the 2.35 kb full length K14 promoter sequence, the following PCR primers were used:

```
                                             (SEQ ID NO: 1)
Fwd  5'-AAGCTTATATTCCATGCTAGGGTTCTG-3'      (ST080)

(SEQ ID NO: 2)
Rev  5'-GGTGCAGAGGAGGGAGGTGAGCGA-3'         (ST081)
```

Human genomic DNA (Promega) was amplified with these primers using Amplitaq DNA polymerase (Promega). Following a denaturation at 95° C. for 4 minutes, samples were subjected to the following for 30 cycles: denaturation at 95° C. for 1 minute, annealing conditions at 58° C. for 1 minute, extension at 72° C. for 3 minutes. A final extension at 72° C. for 7 minutes was followed by a 4° C. hold. The expected PCR product of 2.35 kb was observed. This PCR product was gel purified and subsequently used for cloning into a TA cloning vector. The pCR 2.1-TOPO TA Cloning Kit (Invitrogen/LifeTechnologies) was used according to the standard protocol conditions.

Although thorough sequencing of this promoter has been problematic (typically encountered when sequencing promoter regions presumably due to the high GC content), the cloned promoter sequence is different than the published K14 promoter sequence (Genbank sequence Accession #U110776). The consensus sequence of the cloned Keratin 14 promoter fragment (SEQ ID NO:3) is provided in FIG. 1a.

In order to confirm the functionality of the K14 promoter sequence, a luciferase reporter gene expression system was used. The K14 promoter fragment was shuttled into the Hind III site of the pGL3 firefly luciferase vector multiple cloning site. After subcloning this full length K14 promoter Hind III fragment an opportunity to truncate the promoter fragment by approximately 300 bp was easily accomplished using a single Sma I restriction enzyme site upstream in the multiple cloning site to release a 300 bp 5' promoter fragment. Published experiments demonstrate a similar 5' truncation of the K14 promoter reduces the promoter activity by about 30% (Leask et al., Genes Dev. 4(11):1985-1998 (1990)). The full length promoter fragment (2.3 kb) firefly luciferase activity was compared to that of the 5' truncated Promoter fragment (~2.0 kb) activity. The K14 Promoter Luciferase Vector Construction is described in FIG. 2

Results of luciferase reporter gene expression are as follows. The co-expression of Renilla Luciferase was used to correct for any variability introduced by potentially different transfection efficiencies or possible differences in cell numbers. After normalization, the firefly luciferase reporter gene results demonstrate strong promoter activity from the full length (2.3 kb) K14 promoter fragment and approximately a 30% reduction in firefly luciferase activity in the truncated promoter fragment. This result is consistent with that reported by Leask et al.

Next, the full length K14 promoter was shuttled into the blasticidin selection vector.

Example 2

KGF-2 Cloning and Characterization

This Example describes the isolation, cloning and characterization of KGF-2. Primer sequences were designed based on the published KGF-2 sequence available at Genbank. In order to amplify the 627 bp full length KGF-2 sequence, the following PCR primer sequences (BamH I-EcoR V) were used:

```
                                         (SEQ ID NO: 4)
Fwd  5'-CGCGGATCCGCGATGTGGAAATGGATACTG-3' (ST127)

(SEQ ID NO: 5)
Rev  5'-GGGATATCCTATGAGTGTACCACCATTGGA-3' (ST128)
```

Pfu Turbo DNA Polymerase (Stratagene) was used to minimize the risk of PCR induced errors. Human Universal QUICK-Clone cDNA (CLONTECH) was used as the template for PCR amplification of the full length KGF-2 cDNA. Following a denaturation at 94° C. for 4 minutes, samples were subjected to the following for 30 cycles: denaturation at 94° C. for 30 seconds, annealing conditions at 51° C. for 30 seconds, extension at 72° C. for 1 minute. A final extension at 72° C. for 7 minutes was followed by a 4° C. Hold. The expected PCR product of 627 bp was observed. After amplification, the addition of 3' A-overhangs to the Pfu PCR product was necessary to allow for efficient TA cloning. The PCR product was gel purified using a Matrix Gel Extraction System (Marligen BioScience Inc.). Gel purified PCR products were cloned into a commercially available TA cloning kit. The pCR 2.1-TOPO TA Cloning Kit (Invitrogen/Lifetechnologies) was used according to the standard protocol conditions.

Sequencing reactions were performed using each of the two sequencing primers that span the cloning site (M13 forward and reverse primers). Additionally, overlapping sequence was obtained using the KGF-2 specific primers used to PCR amplify the cDNA (Primers ST127 and ST128). The cDNA sequence was identical to Genbank accession #U67918.

Next, the TA cloned KGF-2 cDNA was shuttled into a pIRES vector. The TA clone containing the correct KGF-2 cDNA sequence was digested with BamHI (5') and EcoRV (3') to release a 627 bp KGF-2 cDNA. This product was cloned directly into the BamHI and EcoRV sites of the mammalian expression pIRESpuro clonal selection vector.

A re-amplification and TA cloning step was necessary to obtain the desired restriction enzyme sites for directional cloning into the pUB-Bsd clonal selection vector. The primer sequences used to amplify the KGF-2 cDNA that contain the Not I and Sal I restriction enzyme sites are as follows.

```
                                         (SEQ ID NO: 109)
Fwd  5'-GCGGCCGCATGTGGAAATGGATACTG-3'     (ST133)

(SEQ ID NO: 110)
Rev  5'-GTCGACCTATGAGTGTACCACCATTGGA-3'   (ST134)
```

The PCR conditions were the same as listed above. Pfu polymerase (Stratagene) was used, but fewer PCR cycles were required because the previous TA clone containing the KGF-2 gene was used as the starting template for this additional round of amplification.

The PCR product contained strategically placed Not I and Sal I restriction enzyme sites. This PCR product was cloned with the pCR 2.1-TOPO TA Cloning Kit (Invitrogen/Lifetechnologies) according to the standard protocol conditions.

The newly cloned KGF-2 cDNA was sequenced, and the sequence was confirmed to be identical to the KGF-2 cDNA sequence (Genbank accession #U67918).

The KGF-2 cDNA clone was shuttled out of the TA cloning vector by digestion with a 5' Not I and a 3' Sal I (ligates to Xho I restriction enzyme cleavage site) restriction enzyme. This fragment was directionally cloned between the K14 promoter and the globin polyA sequences in the pUB-Bsd vector using the Not I and Xho I restriction enzyme sites.

Example 3

Mammalian Expression Vector Design

Figure 3:
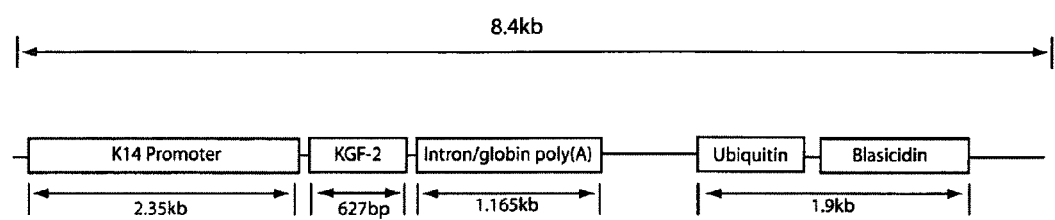
FIG. 3 provides a diagram of the K14-KGF-2 vector.

This Example presents a mammalian expression vector utilized in the present invention. The vector is described in FIG. 3 and comprises the following elements: K14 promoter (2.35 kb)/KGF-2 cDNA (627 bp)/globin intron & poly(A) (1.165 kb)/pUB-Bsd (4.245 kb).

Example 4

KGF-2 mRNA Expression Diagnostic Screen (RT-PCR)

This Example describes the KGF-2 mRNA expression diagnostic screen utilized in the present invention. NIKS cells were transfected using Trans-It Keratinocyte Transfection Reagent (Mirus Corp.) and grown in either EpiLife Medium (Cascade Biologics) or NIKS STRATALIFE medium (Stratatech Corporation). Supernatants were collected for three days and used in the development of a direct KGF-2 ELISA Assay. After three days the cells were lysed with Trizol Reagent (Invitrogen) for RNA isolation. First strand cDNA synthesis was performed using total RNA isolated form these transiently transfected NIKS cells. The following primer sequences were utilized:

```
                                         (SEQ ID NO: 6)
Fwd
5'-TGCTGTTCTTGGTGTCTTCCG-3'              (ST135)

(SEQ ID NO: 7)
KGF-2 Specific Rev
5'-CAACCAGCACGTTGCCCAGG-3'               (ST124)

(SEQ ID NO: 8)
Globin fragment Specific Oligo d(T)
5'TGTTACCAATCTGAAGTGGGAGC                (ST112)

GGCCGCCCTTTTTTTTTTTTTTTTTT-3'
```

Next, reverse transcriptase reactions were conducted under the following conditions: RNA Priming Reaction—2.5 ug total RNA (Template), 0.5 mM dNTP mix, Oligo dT (0.5 ug)—Incubate 65 for 5 minutes, on ice 3 minutes. First strand cDNA synthesis reaction (added to the RNA Priming Reaction)—1×RT buffer (Promega Corp.), Rnase Out (40 U) (Invitrogen), M-MLV RT (200 U) (Promega), 42 degrees for 50 minutes, heat 70 degrees for 15 minutes. One microliter (1 ul) of RT reaction template was used for the subsequent PCR reaction.

Figure 4:
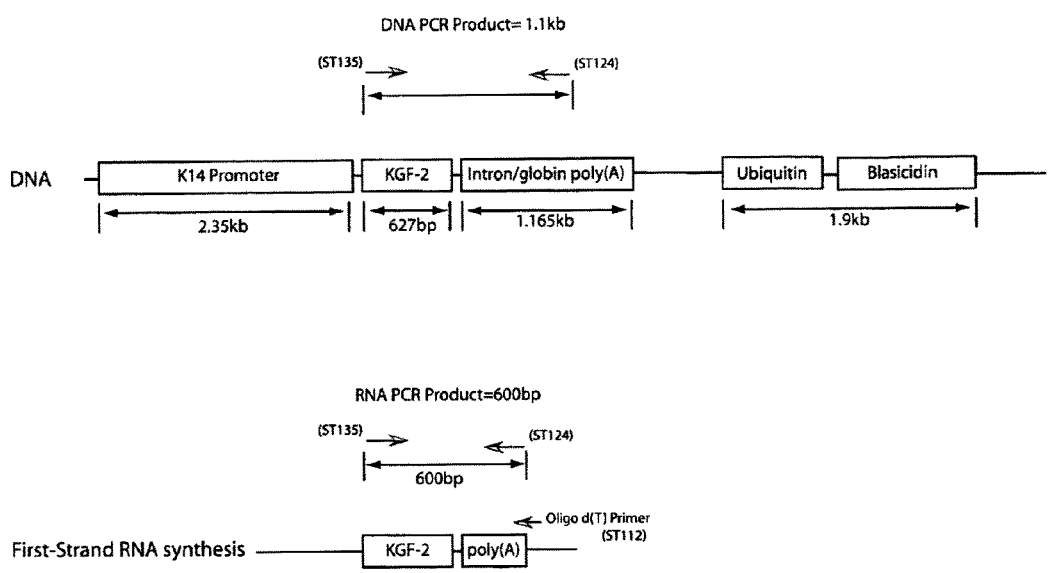
FIG. 4 provides a diagram of the RT-PCR strategy.

Next, PCR was conducted. Following a denaturation at 95° C. for 5 minutes, samples were subjected to the following for 35 cycles: Denaturation at 94° C. for 30 seconds, Annealing conditions at 60° C. for 30 seconds, Extension at 72° C. for 1 minute. A final Extension at 72° C. for 7 minutes was followed by a 4° C. Hold. The RT-PCR strategy is diagrammed in FIG. 4.

A DNA vector specific product of 1.1 kb was observed along with the specific product associated with first strand cDNA synthesis (KGF-2 RNA specific Product) of approximately 600 bp was observed. No KGF-2 RNA specific product was observed in either the mock (vector w/o KGF-2 cDNA insert) control plasmid transfection or the reverse transcriptase minus control reaction.

Example 5

KGF-2 Protein Expression Diagnostic Screen (Direct ELISA)

This Example describes the KGF-2 protein expression diagnostic screen used in the present invention.

NIKS cells were transfected using Trans-It Keratinocyte Transfection Reagent (Mirus Corp.) and grown in either EpiLife Medium (Cascade Biologics) or NIKS medium (Stratatech Corporation). Supernatants were collected for three days and used in the development of a direct KGF-2 ELISA Assay. The 100 ul supernatants were incubated in plate (Nunc Immunoassay plate) over night; at a minimum samples were plated in duplicate. The next day, the samples were washed 3×(1×PBS/0.05% Tween-20) 300 ul/well; blocked plate (1×PBS/1% BSA/5% Sucrose) 300 ul/well @ rt for 30 minutes; washed 3×(1×PBS/0.05% Tween-20) 300 ul/well; incubated with rabbit anti-huKGF-2 Ab (0.2 ug/well) @ rt for 2 hours; washed 3×(1×PBS/0.05% Tween-20) 300 ul/well; incubated with goat anti-rabbit HRP (0.8 mg/ml) Ab—use at 1:1000 dilution @ rt for 30 minutes; washed 3×(1×PBS/0.05% Tween-20) 300 ul/well; prewarmed TMB @ rt 100 ul/well for 30 minutes at room temperature; added 50 ul of 2N H2SO4; read O.D. 450 nm and 620 nm; corrected for plate imperfections (450 nm-620 nm).

This experiment demonstrates elevated KGF-2 protein levels are detected in the supernatants of transiently transfected NIKS cells, when compared to either mock transfection (empty vector) or medium alone controls.

Example 6

Isolation of NIKS Cells Expressing Exogenously Introduced Full Length Human KGF-2 Protein This Example describes the isolation of NIKS cells that express KGF-2.

A. Clonal Isolation Strategy—

Vector Construct—Keratin 14 promoter/KGF-2 cDNA/pUb-Bsd plasmid. A DNA fragment encoding KGF-2 was isolated by PCR and sequenced to verify the identity and integrity of the PCR product. The DNA fragment was identical to previously reported sequences for KGF-2. The DNA fragment encoding KGF-2 was cloned into a mammalian expression vector containing a blasticidin resistant cassette. Blasticidin has been used to select for stably transfected keratinocytes, which are subsequently able to undergo normal differentiation.

To provide for constitutive expression of KGF-2 in keratinocytes of the basal epidermal layer, constructs were generated in which expression of KGF-2 is under the control of the human keratin-14 (K14) promoter. A 2.3 kb genomic DNA fragment containing the K14 promoter was amplified and its activity was confirmed by the ability to promote luciferase expression from the pGL3 reporter plasmid (Promega) in NIKS cells. The 2.3 kb K14 promoter was then cloned into the pUb-bsd vector (Invitrogen). Subsequently, the KGF-2 coding region was cloned downstream of the K14 promoter and a DNA fragment containing the rabbit β-globin intron and poly (A) signal was inserted downstream of the KGF-2 coding region to complete this mammalian expression vector construction.

The structure of the final vector was confirmed by restriction enzyme mapping and DNA sequencing. Oligonucleotide primers were synthesized and used to examine the expression of this construct in NIKS keratinocyte cells using semi-quantitative RT-PCR analysis. The primers were designed to span an intron in the rabbit β-globin fragment, such that PCR products generated from a spliced RNA template is approximately 500 bp smaller than the corresponding fragment amplified from genomic DNA.

Transfection—Transit-Keratinocyte (Minis) transfection reagent was used to introduce the KGF-2 vector DNA into monolayer NIKS cell cultures. Twenty-four to forty-eight hours post transfection the NIKS cells were plated onto a blasticidin feeder layer of cells and fed with blasticidin selection medium.

Selection—NIKS keratinocyte clones were cocultured in the presence of blasticidin resistance feeder cells and selected for growth in presence of NIKS™ medium containing 2.5 ug/ml blasticidin. Only those colonies that continued to grow in the presence of blasticidin selection for duration of selection (a minimum of 18 days) were isolated and expanded for further characterization.

Clone Isolation—A traditional "Ring cloning" method to isolate blasticidin resistant colonies re-plated to individual tissue culture plates (p35 and p100) containing mouse fibroblast feeder cells. When these cultures reach 80-90% confluence, the p35 cultures are harvested for expression analysis and the p100 cultures are used for the subsequent expansion phase.

Characterization of Stably-transfected NIKS keratinocytes—Stable NIKS keratinocyte colonies that survived the selection scheme therefore are presumed to contain the K14-KGF-2 expression construct. To confirm the presence of the KGF-2 transgene, genomic DNA was isolated from each clone and amplified with vector specific primers. This PCR screen was designed to reconcile products derived from transgene DNA from that of potential endogenous KGF-2 DNA products. Multiple clones were obtained using this construct and associated selection scheme.

Expansion—The results of expression analysis obtained from the p35 cultures dictate which clones will be expanded for further characterization. The p100 plates from cultures identified as having positive expression are grown to approximately 50-80% confluence then expanded onto several plates containing mouse fibroblast feeder cells.

B. Results

Twenty-nine NIKS clonal isolates that survived drug selection were isolated and characterized. Four of the 29 originally identified clones did not survive the expansion phase. The remaining 25 clones were successfully expanded and confirmed to express KGF-2, at the level of transcription, determined using RT-PCR. Total RNA isolated from previous transient transfections served as positive RT-PCR controls. Negative controls were identical reactions run in the absence of reverse transcriptase. The presence of a KGF-2 transgene present in the genome of any clone yielded an anticipated PCR product of approximately 1 Kb in size with the use of a transgene specific primer set. Clones were categorized by semi-quantitative expression analysis into categories representing low, medium or high expression levels.

Example 7

KGF-2 RNA and Protein Expression in Monolayer Cultures

This example describes experiments analyzing the expression of KGF-2 in monolayer cell cultures. Each of the confirmed RT-PCR positive clones were assayed for protein expression; this effort resulted in the detection of KGF-2 protein over expression in supernatants. Commercially available KGF-2 specific antibodies were used to investigate protein levels of secreted KGF-2 protein detected in supernatants. Western Blot and ELISA analysis was performed on cell culture supernatants of clones and compared to native NIKS cell supernatants. A cell growth assay is being developed to investigate possible biological effects of conditioned media from cultured NIKS KGF-2 clones compared to endogenous NIKS cell supernatants.

A. RT-PCR

Transgene specific PCR products were semi-quantitatively reported relative to GAPDH specific products. The transgene specific PCR primer set was designed to produce a product utilizing the rabbit β-globin intron sequence region restricted to the transgene; as a result this product is easily distinguishable from endogenous KGF-2 product.

Transfected cultures were assayed for mRNA expression levels approximately 24 hours post-transfection. A commercially available RNA isolation kit was used to isolate total cellular RNA (Invitrogen, Carlsbad, Calif.). Total RNA provided a suitable template for the subsequent first strand cDNA synthesis (reverse-transcriptase) reaction followed by the polymerase chain reaction (RT-PCR). Amplification products are resolved on an ethidium bromide stained agarose gel. The anticipated PCR products specific for the transgene DNA and mRNA product is 1.0 Kb and 550 bp respectively.

An additional RT-PCR primer set was designed to specifically amplify the KGF-2 gene mRNA product, however this primer set does not distinguish between endogenous and transgene messages. Despite the inability to distinguish endogenous mRNA from transgene mRNA intensities were semi-quantitatively compared using the endogenous control samples (untransfected and transfected with empty vector) as a point of reference.

To compare the level of KGF-2 RNA expressed from the K14-KGF-2 construct with KGF-2 RNA from the endogenous gene, RT-PCR analysis was performed using primers that will amplify KGF-2 RNA regardless of its origin. Under these conditions endogenous KGF-2 has not been identified using these RT-PCR conditions, therefore, KGF-2 does not appear to be expressed in NIKS keratinocytes. To date, no KGF-2 RT-PCR products from non-transfected NIKS cell total RNA controls have been identified. The anticipated 550 bp fragment is routinely observed in NIKS cells transfected with the KGF-2 transgene. The KGF-2 expressed from the K14-KGF-2 construct gives rise to the 550 bp RT-PCR product. RT-PCR analysis of two K14-KGF-2 clones show that the 550 bp KGF-2 RNA product is overexpressed compared to non-detected endogenous KGF-2 levels. No PCR products were seen in control reactions in which reverse transcriptase was omitted, demonstrating that these products are derived from RNA and not from template contamination of the PCR reactions. These results demonstrate that NIKS clones stably-transfected with the K14-KGF-2 expression construct specifically overexpress the KGF-2 transgene.

B. Western Blot

Western blot analysis demonstrates specific products at anticipated gel positions that correspond to post translational modification forms of KGF-2 reported in the literature. Prominent KGF-2 specific protein bands are observed between 19 and 30 kDa. Specific KGF-2 band product intensities observed in Western blot analysis corroborate the semi-quantitative RT-PCR expression results. Endogenous KGF-2 is not detected in unmodified NIKS control cultures; these findings are consistent with results obtained from semi-quantitative mRNA expression analysis. A positive control (recombinant human KGF-2) protein was used at concentrations ranging from 0.3 to 0.5 ng/lane that routinely corresponds with the 19 kDa KGF-2 protein band.

To quantify KGF-2 protein expression in stably-transfected K14-KGF-2 clones, a KGF-2 Sandwich ELISA (Polyclonal antibodies from R&D Systems and Santa Cruz) was developed to compare KGF-2 levels between various K14-KGF-2 clones and untransfected NIKS cells. Supernatants from several K14-KGF-2 clones contain elevated levels of KGF-2 compared to unmodified NIKS cell control samples. This increase in KGF-2 protein expression is consistent with the increase seen by RT-PCR analysis. These results demonstrate that NIKS cells can be engineered to stably express and secrete elevated levels of KGF-2 protein.

C. ELISA

A Sandwich assay was developed to compare secreted KGF-2 levels; assay results are reported as amount of protein detected per milliliter of cell supernatant. The level of KGF-2 protein detected in supernatants is well above levels detected in unmodified NIKS cell supernatants (negative control) samples. ELISA values were obtained for individual clones and used to assign relative expression levels.

Taken together, the expression analysis compiled from each of these assays was used to group clones into relative expression levels when compared to one another.

Example 8

KGF-2 RNA and Protein Expression in Organotypic Cultures

This example describes experiments analyzing the expression of KGF-2 in organotypic cultures.

A. RT-PCR—Comparison of Biopsy Samples (Clones Versus NIKS)

The expression of KGF-2 mRNA was examined by RT-PCR in skin tissue generated from stable clones. Total RNA was extracted from skin tissue and subjected to RT-PCR using primers that detect mRNA expressed from the KGF-2 transgene, but not from an endogenous KGF-2 gene. KGF-2 mRNA was detected in skin tissue prepared from a K14-KGF-2 clone, but was not detected in RNA from skin tissue prepared from untransfected NIKS cells. These results demonstrate that the K14-KGF-2 construct is expressed within the context of stratified epidermis.

B. Western Blot

Results were similar to those obtained for the monolayer cell cultures.

C. ELISA

Results were similar to those obtained for the monolayer cell cultures.

D. Histology—Biopsy of Clones Versus NIKS

To verify that stably-transfected clones containing the K14-KGF-2 expression constructs undergo normal epidermal differentiation, cultured skin tissue containing these clones was prepared. After two weeks in organotypic culture, K14-KGF-2 clones formed cultured skin tissue with normal epidermal morphology. These findings indicate that elevated expression of KGF-2 does not interfere with the ability of NIKS cells to undergo normal epidermal differentiation.

Example 9

Use of Skin Equivalents Expressing Exogenous KGF-2 to Close Wounds

This Example describes preliminary experimental results obtained when skin equivalents expressing exogenous KGF-2 were used to close wounds in a mouse wound model. In this experiment, organotypic cultured skin (i.e., skin equivalents) were grafted onto the denuded back of athymic nude mice. Skin equivalents containing native NIKS cells were compared to genetically modified skin equivalents expressing KGF-2. All tissues were meshed (2:1 ratio) immediately prior to being grafted onto mice. Interstitial wound space closure was monitored in the mice. Each observation time point included recording micrometer measurements of the wound area; these measurements were supplemented with digital photography. At post operative day 3 (POD 3), complete wound closure of interstitial spaces have been observed in the mice with the genetically modified NIKS organotypic skin tissue (KGF-2), but not observed in mice grafted with the NIKS culture tissue control.

Example 10

Mammalian Expression Vector Design

Figure 5:
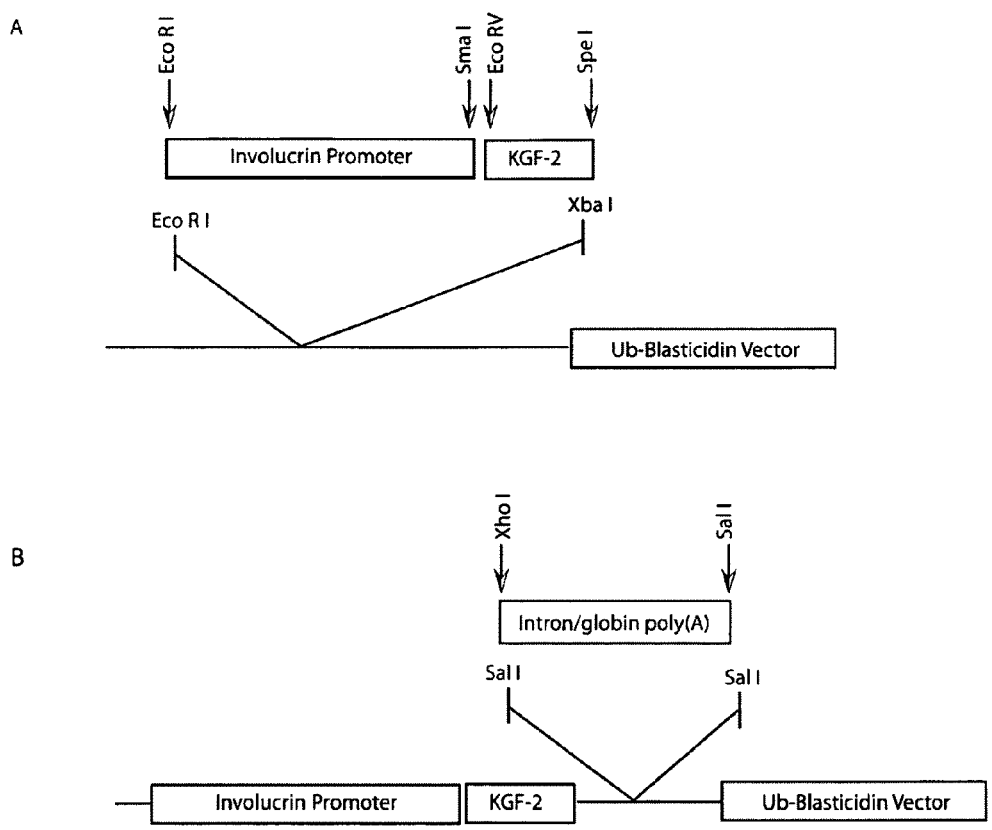
FIG. 5 provides a diagram of a vector for the expression of KGF-2 by the Involucrin promoter.

This Example describes a mammalian expression vector utilized in some embodiments of the present invention. The vector is described in FIG. 5 and comprises the following elements: Involucrin promoter (3.7 kb)/KGF-2 cDNA (627 bp)/globin intron & poly(A) (1.165 kb)/pUB-Bsd (4.245 kb).
Construction of Expression Vector A genomic DNA fragment containing the human involucrin promoter sequence was isolated using PCR primers based on published sequences (Crish et al., J Biol Chem, 1998. 273(46): p. 30460-5). The integrity of the cloned involucrin promoter PCR product was confirmed by restriction enzyme analysis and DNA sequencing using involucrin specific primers. The involucrin promoter is not expressed in undifferentiated keratinocytes, but is specifically activated in differentiated keratinocytes. It is preferable to direct overexpression of the KGF-2 to differentiated keratinocytes to avoid interfering with normal keratinocyte differentiation.

The coding region for the KGF-2 gene is cloned into the pUB-Bsd expression vector (Invitrogen, Carlsbad, Calif.). This vector is modified by inserting the involucrin promoter upstream of the multiple cloning site. This vector contains the blasticidin drug selection cassette that utilizes the ubiquitin promoter sequence driving blasticidin gene expression. Briefly, gene specific primers for KGF-2 were designed to contain terminal restriction enzyme sites (5'-Eco RV and 3'-Spe I). These primers were used in a PCR reaction containing TA cloned cDNA template. The modified KGF-2 PCR product (containing terminal restriction enzyme sites) was cloned into the TA cloning vector (Invitrogen) then sequenced. The KGF-2 cDNA gene product was shuttled from the TA cloning vector into a mammalian expression vector. Complete mammalian expression vector construction required a two step vector assembly approach shown in FIG. 5.

KGF-2 mRNA Expression Diagnostic Screen (RT-PCR)

A mRNA expression screen was performed as described in Example 4.
Involucrin Promoter/KGF-2 Expression Construct
1) Electroporation transfection method results—

TABLE 1

Summary of clonal selection and mRNA expression results.

| Experiment | Clones Picked | Clones Survived | Positive |
|---|---|---|---|
| 54:29 | 4 | 4 | 4 |
| 54:31 | 2 | 2 | 2 |
| 68:31 | 5 | 3 | 2 |

2) Trans-IT Keratinocyte Transfection Method Results—

TABLE 2

Summary of clonal selection and mRNA expression results.

| Experiment | Clones Picked | Clones Survived | Positive |
|---|---|---|---|
| 58:51 (TransIT) | 16 | 2 | 2 |

Isolation of NIKS Cells Expressing Exogenously Introduced Full Length Human KGF-2 Protein A. Clonal Isolation Strategy—
Vector Construct—This clonal isolation strategy includes the use of a DNA maxiprep (Qiagen) of the Involucrin/KGF-2 cDNA/Globin poly(A) fragment/pUb-Bsd plasmid.

TransIT-keratinocyte Transfection Method—Transit-Keratinocyte (Minis) transfection reagent was used to introduce the KGF-2 vector DNA into monolayer NIKS cell cultures. Twenty-four to forty-eight hours post transfection the NIKS cells were plated onto a blasticidin feeder layer of cells and fed with blasticidin selection medium.

Electroporation Transfection Method—Early passage NIKS cells were harvested at @ approximately 50-70% confluence. Cells were pelleted and the pellet resuspended ($2\times10^6$ cells/800 ul) in F-12/DME (5:1).

800 ul of NIKS cell suspension was placed in 0.4 cm electroporation cuvette, DNA was added (10-30 ug, linear or supercoiled), placed in cuvette holder of the GenePulser and started. All steps were done at room temperature; the cells were not placed on ice at any time during this procedure. The actual voltage and capacitance values were recorded Electroporated NIKS cells were removed from the cuvette and diluted into 25-50 mls of fresh NIKS medium, mixed well by pipetting, and plated (5-10 mls) per p150 containing blasticidin resistant feeders (using either 5 or 10 p150's per transfection reaction).

The following day, the medium is replaced on the p150's with blasticidin containing medium (2.5 ug/ml blasticidin).
BioRad GenePulser Electroporation Settings:
Exponential Pulse Program
270 volts
950 uF
∞ ohms
0.4 cm cuvette
Selection—NIKS keratinocyte clones were cocultured in the presence of blasticidin resistance feeder cells and selected for growth in presence of NIKS medium containing 2.5 ug/ml blasticidin. Only those colonies that continued to grow in the presence of blasticidin selection for duration of selection (a minimum of 18 days) were isolated and expanded for further characterization.

Clone Isolation—A traditional "Ring cloning" method to isolate blasticidin resistant colonies re-plated to individual tissue culture plates (p35 and p100) containing mouse fibroblast feeder cells. When these cultures reach 80-90% confluence, the p35 cultures are harvested for expression analysis and the p100 cultures are used for the subsequent expansion phase.

Characterization of Stably-transfected NIKS keratinocytes—Stable NIKS keratinocyte colonies that survived the selection scheme therefore are presumed to contain the Involucrin-KGF-2 expression construct. To confirm expression of the KGF-2 transgene, total RNA was isolated from each clone to provide a template for RT-PCR analysis. Multiple clones were obtained using this construct and associated selection scheme.

Expansion—The results of expression analysis obtained from the p35 cultures dictate which clones will be expanded for further characterization. The p100 plates from cultures identified as having positive expression are grown to approximately 50-80% confluence and then expanded onto several plates containing mouse fibroblast feeder cells.

B. Results—

TransIT-Kerationcyte method of transfection for clonal selection—Sixteen NIKS clonal isolates that survived drug selection were isolated and characterized. Only two of the 16 originally identified clones survived the expansion phase. These two clones were successfully expanded and confirmed to express KGF-2, at the level of transcription, determined using RT-PCR. Total RNA isolated from previous transient transfections served as positive RT-PCR controls. Negative controls were identical reactions run in the absence of reverse transcriptase. The presence of a KGF-2 transgene present in the genome of any clone yielded an anticipated PCR product of approximately 1 Kb in size with the use of a transgene specific primer set. Clones were categorized by semi-quantitative expression analysis into categories representing low, medium or high expression levels.

Electroporation method transfection for clonal selection—In one selection experiment, Four NIKS clonal isolates that survived drug selection were isolated and characterized. All four originally identified clones survived the expansion phase. In a second experiment, Two NIKS clonal isolates that survived drug selection were isolated and characterized. Both originally identified clones survived the expansion phase. In a third experiment, Five NIKS clonal isolates that survived drug selection were isolated and characterized. All five originally identified clones survived the expansion phase.

All clones generated in this series of selection experiments were successfully expanded and confirmed to express KGF-2, at the level of transcription, determined using RT-PCR. Total RNA isolated from previous transient transfections served as positive RT-PCR controls. Negative controls were identical reactions run in the absence of reverse transcriptase. The presence of a KGF-2 transgene present in the genome of any clone yielded an anticipated PCR product of approximately 1 Kb in size with the use of a transgene specific primer set. Clones were categorized by semi-quantitative expression analysis into categories representing low, medium or high expression levels.

Example 11

Expression of Endogenous Human Beta Defensins in NIKS Cells

This example provides an analysis of endogenous human beta defensin (hBD) expression in NIKS cells. Since it was unknown if NIKS cells express hBDs, RT-PCR analysis was performed to verify detectable levels of hBD-1, hBD-2, and hBD-3 in both monolayer and organotypic cultures of NIKS keratinocytes. Specifically, reverse transcriptase reactions were performed on both monolayer and organotypic NIKS cell cultures for each of the human β-defensin genes being studied. Reverse transcriptase reactions were performed using total RNA isolated from both NIKS cell monolayer and organotypic cultures using an oligonucleotide d(T) primer. One microliter of RT reaction template was used in a 20 ul PCR reaction containing gene specific primers. PCR reactions were conducted as follows—Denaturation at 95° C. for 5 minutes, samples were subjected to the following for 35 cycles: Denaturation at 94° C. for 30 seconds, Annealing conditions at 58° C. for 30 seconds, Extension at 72° C. for 30 seconds. A final Extension at 72° C. for 7 minutes was followed by a 4° C. Hold. Fifteen microliters of a 20 ul PCR reaction was resolved on a 1% agarose gel containing ethidium bromide. The gels were analyzed for the anticipated PCR product sizes of 275 bp, 205 bp & 290 bp corresponding to hBD-1, hBD-2 & hBD-3 respectively.

Intact human skin is reported to express all three human hBDs and their expression levels are increased in response to injury and inflammation. To date there have been no reports on the expression of hBDs in primary human keratinocytes in monolayer and only one report on hBD-2 protein expression in a nontherapeutic product, Matek's EpiDerm. A thorough analysis of the RNA expression levels of all three hBDs in both monolayer and organotypic cultures of NIKS keratinocytes was conducted. Organotypic culture of NIKS keratinocytes results in enhanced levels of all hBDs relative to monolayer culture conditions, although the magnitude of induction varied among the hBDs. In monolayers of NIKS cells the steady state mRNA expression levels of hBD-2 and hBD-3 were below the limit of detection. hBD-3, a broad spectrum antimicrobial peptide, was poorly expressed even in organotypic culture supporting the notion that overexpression of hBD-3 in NIKS keratinocytes will result in enhanced antimicrobial properties especially in bioengineered human skin tissue generated by organotypic culture techniques.

Example 12

Cloning of Human Beta Defensin

This example describes the cloning of hBD-1, h-BD2, and hBD3 from NIKS cells. The reverse transcriptase-polymerase chain reaction products described in Example 1 were cloned into the TA cloning vector (Invitrogen) and sequenced to confirm their genetic identity. A summary of the sequencing results for each of the cloned cDNA products is as follows. Human β-defensin-1 cDNA sequence was confirmed to be identical to Genbank Accession #U73945 for hBD-1. Sequence of the human β-defensin-2 cDNA reveled a point mutation at amino acid position #48 (Lys→Arg) when compared to Genbank Accession #AF040153 for hBD-2. The sequence was amplified, using Pfu proof-reading polymerase, and cloned. The sequence was confirmed to be identical to the GenBank sequence.

The sequence of the human β-defensin-3 cDNA clone was originally found to contain two point mutations at amino acid positions #57 (Thr→Met) and #62(Cys→Tyr). Pfu polymerase (proof-reading enzyme) was used to successfully re-amplify the hBD-3 cDNA which was cloned into the TA cloning vector and sequenced. The sequence of this new clone is identical to that reported in the Genbank Accession #AF295370 for hBD-3.

Example 13

Construction of Expression Vectors

The example describes the construction of hBD expression vectors. A genomic DNA fragment containing the human involucrin promoter sequence was isolated using PCR primers based on published sequences. Crish, J. F., T. M. Zaim, and R. L. Eckert, *The distal regulatory region of the human involucrin promoter is required for expression in epidermis*. J Biol Chem, 1998. 273(46): p. 30460-5. The integrity of the cloned involucrin promoter PCR product was confirmed by restriction enzyme analysis and DNA sequencing using involucrin specific primers. The involucrin promoter is not expressed in undifferentiated keratinocytes, but is specifically activated in differentiated keratinocytes. In previous studies, we have demonstrated the use of this involucrin promoter fragment support expression in monolayer cultures of NIKS keratinocytes. It is preferable to direct overexpression of the β-defensins to differentiated keratinocytes to avoid interfering with normal keratinocyte differentiation.

Figure 12:
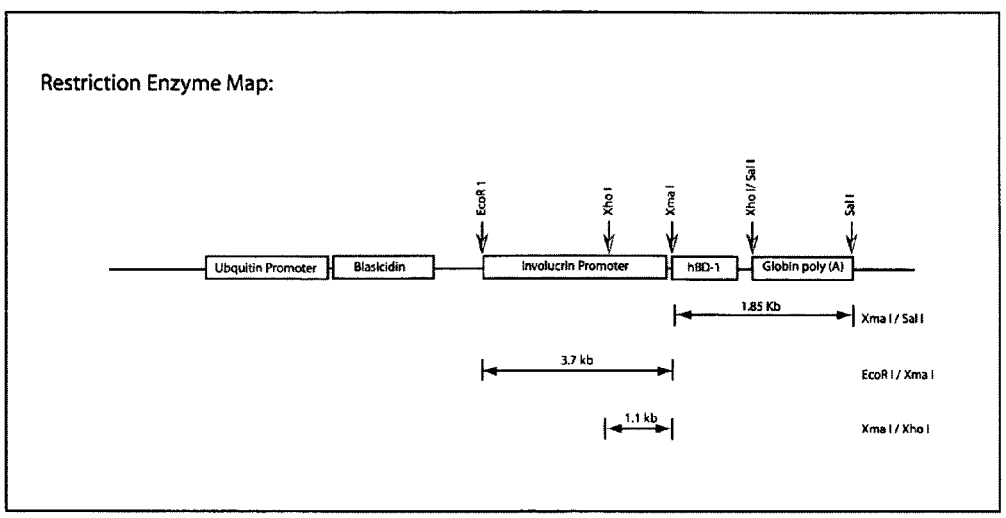
FIG. 12 is a restriction enzyme map of the human β-defensin-1 mammalian expression vector.
Figure 13:
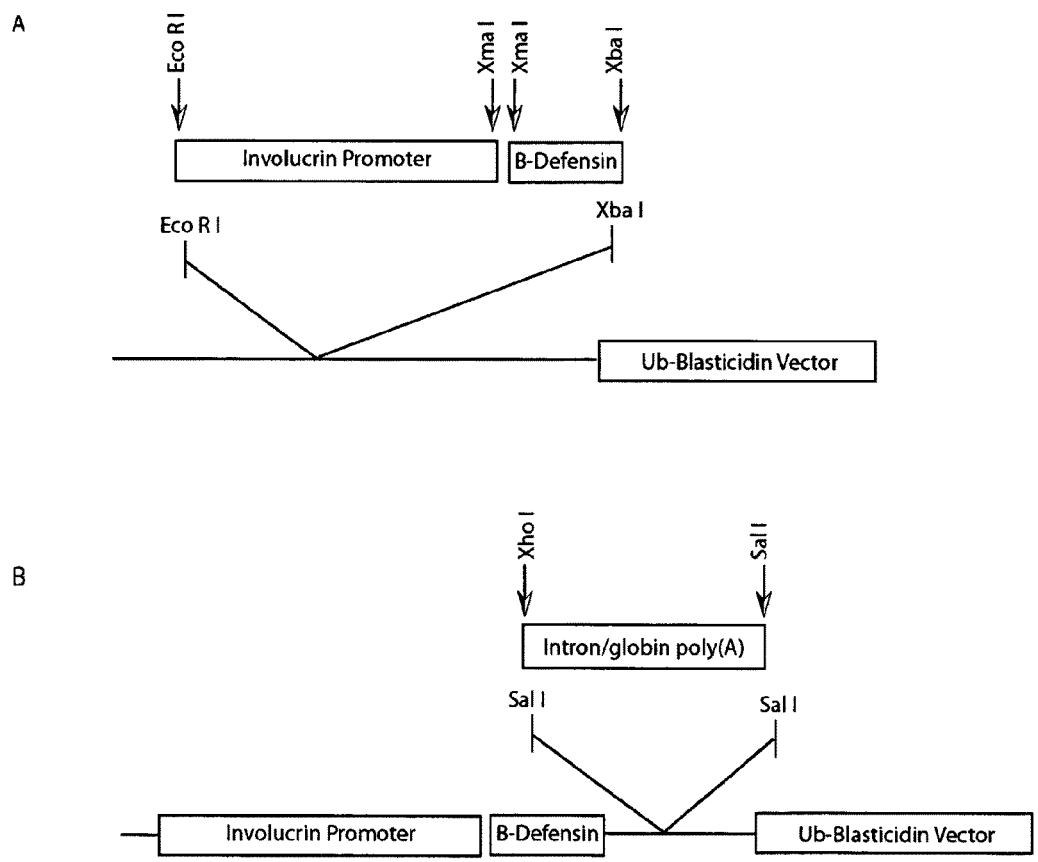
FIG. 13 provides the cloning strategy for the human β-defensin vectors.

The coding region for each of the β-defensin genes is cloned into the pUB-Bsd expression vector (Invitrogen, Carlsbad, Calif.). This vector is modified by inserting the involucrin promoter upstream of the multiple cloning site. This vector contains the blasticidin drug selection cassette that utilizes the ubiquitin promoter sequence driving blasticidin gene expression. A restriction enzyme map of the hBD1 vector is provided in FIG. 12. Briefly, gene specific primers for hBD-1 were designed to contain terminal restriction enzyme sites (5'-Xma I and 3'-Xba I). These primers were used in an RT-PCR reaction containing total cellular RNA isolated from NIKS cells. The hBD-1 PCR product was cloned into the TA cloning vector (Invitrogen) then sequenced. The defensin cDNA gene product was shuttled from the TA cloning vector into a mammalian expression vector. Complete mammalian expression vector construction required a two step vector assembly approach shown in FIG. 13. A similar cloning strategy was used to generate the hBD-2 and hBD-3 mammalian expression constructs.

Example 14

Expression of Exogenous hBD in NIKS Cells

Purified DNA from each of the Involucrin-β-defensin-UB-Bsd vectors was introduced into NIKS cells. Specifically, NIKS cells were transfected using TransIt-Keratinocyte reagent (Mirus Corporation), which has been used to efficiently transfect NIKS cells. Negative control samples included mock transfected (no DNA) or empty vector (no β-defensin) transfected populations of NIKS cells.

mRNA analysis: Transfected cultures were assayed for mRNA expression levels approximately 24 hrs post-transfection. A commercially available RNA isolation kit was used to isolate total cellular RNA (Invitrogen, Carlsbad, Calif.). Total RNA provided a suitable template for the subsequent first strand cDNA synthesis (reverse-transcriptase) reaction followed by the polymerase chain reaction (RT-PCR). Amplification products were resolved on an ethidium bromide stained agarose gel. The anticipated PCR products specific for the transgene DNA and mRNA is as follows—hBD-1 (720 bp and 220 bp), hBD-2 (700 bp and 200 bp), and hBD-3 (710 bp and 210 bp) respectively.

Results of this experiment confirm the anticipated RT-PCR product sizes, for each of the three defensins. Also, as anticipated in the reverse transcriptase minus control reactions a single robust signal was detected which corresponds to the amplification of the transgene DNA. No specific PCR products were observed in the mock transfected control reactions.

Protein analysis: Culture medium from cells transiently transfected with each of the three candidate β-defensin transgenes is assayed for β-defensin peptide production using an Enzyme-Linked Immunosorbent Assay (ELISA) and Western Blotting assays using anti-β-defensin antibodies (Santa Cruz Biotechnology, Santa Cruz, Calif.). A comparison is made to endogenous levels from non-transfected NIKS cells. A synthetic peptide, positive control, is included in these assays. Cell lysates may be required for analysis as β-defensin protein may remain associated with the outer membranes of the cells rather than freely secreted into the culture medium.

Example 15

Isolation of NIKS Cells Expressing Exogenously Introduced Full Length hBD-1 Protein This Example describes the isolation of NIKS cells that express hBD-1.

A. Clonal Isolation Strategy

Vector Construct—Involucrin promoter/hBD-1 cDNA/pUb-Bsd plasmid. A DNA fragment encoding hBD-1 was isolated by PCR and sequenced to verify the identity and integrity of the PCR product. The DNA fragment was identical to previously reported sequences for hBD-1. The DNA fragment encoding hBD-1 was cloned into a mammalian expression vector containing a blasticidin resistant cassette. Blasticidin has been used to select for stably transfected keratinocytes, which are subsequently able to undergo normal differentiation.

To provide for constitutive expression of hBD-1 in keratinocytes of the stratified epidermal layer, constructs were generated in which expression of hBD-1 is under the control of the human Involucrin promoter. A 3.7 kb genomic DNA fragment containing the Involucrin promoter was amplified then cloned into the pUb-bsd vector (Invitrogen). The hBD-1 coding region was cloned downstream of the Involucrin promoter and a DNA fragment containing the rabbit β-globin intron and poly (A) signal was inserted downstream of the hBD-1 coding region to complete this mammalian expression vector construction.

The structure of the final vector was confirmed by restriction enzyme mapping and DNA sequencing. Oligonucleotide primers were synthesized and used to examine the expression of this construct in NIKS keratinocyte cells using semi-quantitative RT-PCR analysis. The primers were designed to span an intron in the rabbit β-globin fragment, such that PCR products generated from a spliced RNA template are approximately 500 bp smaller than the corresponding fragment amplified from genomic DNA.

Transfection—Transit-Keratinocyte (Minis) transfection reagent was used to introduce the hBD-1 vector DNA into monolayer NIKS cell cultures. Twenty-four to forty-eight hours post transfection the NIKS cells were plated onto a blasticidin feeder layer of cells and fed with blasticidin selection medium.

Selection—NIKS keratinocyte clones were cocultured in the presence of blasticidin resistance feeder cells and selected for growth in presence of NIKS medium containing 2.5 ug/ml blasticidin. Only those colonies that continued to grow in the presence of blasticidin selection for duration of selection (a minimum of 18 days) were isolated and expanded for further characterization.

Clone Isolation—A traditional "Ring cloning" method was used to isolate blasticidin resistant colonies re-plated to individual tissue culture plates (p35 and p100) containing mouse fibroblast feeder cells. When these cultures reach 80-90% confluence, the p35 cultures are harvested for expression analysis and the p100 cultures are used for the subsequent expansion phase.

Characterization of Stably-transfected NIKS keratinocytes—Stable NIKS keratinocyte colonies that survived the selection scheme therefore are presumed to contain the Involucrin-hBD-1 expression construct. To confirm the presence of the hBD-1 transgene, total RNA was isolated from each clone and RT-PCR amplified with transgene specific primers. This PCR screen was designed to reconcile products derived from transgene total RNA from that of potential endogenous hBD-1 expression products. Multiple clones were obtained using this construct and associated selection scheme.

Expansion—The results of expression analysis obtained from the p35 cultures dictate which clones were expanded for further characterization. The p100 plates from cultures identified as having positive expression were grown to approximately 50-80% confluence then expanded onto several plates containing mouse fibroblast feeder cells.

B. Results

Thirty NIKS clonal isolates that survived drug selection were isolated and characterized. Ten of the 30 originally identified clones did not survive the expansion phase. The remaining 20 clones were successfully expanded and confirmed to express hBD-1, at the level of transcription, determined using RT-PCR. Total RNA isolated from previous transient transfections served as positive RT-PCR controls. Negative controls were identical reactions run in the absence of reverse transcriptase. The presence of a hBD-1 transgene detected in the genome of any clone yielded an anticipated PCR product of approximately 720 bp in size with the use of a transgene specific primer set. Clones were categorized by semi-quantitative expression analysis into categories representing low, medium or high expression levels.

NIKS cell expression of exogenously introduced full length hBD-3 protein have also been isolated in the same fashion as described above.

Example 16 hBD Activity in NIKS Cells

This Example describes assays for hBD activity. To determine if transient expression of β-defensins in NIKS monolayer cultures results in enhanced bactericidal activity, a modified in vitro inhibition zone assay is utilized. Hultmark, D., et al., *Insect immunity. Attacins, a family of antibacterial proteins from Hyalophora cecropia*. Embo J, 1983. 2(4): p. 571-6. Briefly, thin (1 mm) agarose plates are seeded with a microbe of choice (*E. coli, S. aureus, P. aeruginosa, S. pyogenes* or *C. albicans*). The melted agarose (1%) contains Luria-Bertani broth with or without supplemented salt. Vogel, H. J., *Acetylornithinase of Escherichia coli: partial purification and some properties*. J Biol Chem, 1956. 218: p. 97-106. The test organism, (~5×10$^4$ log-phase cells/ml) is added just before pouring the plate. Small wells (3 mm diameter) are punched in the assay plates and loaded with 3 ul of harvested culture medium conditioned for at least 24 hours by untransfected NIKS, NIKS transiently transfected with the empty expression construct, or NIKS transiently expressing each β-defensin. Alternatively, discs are loaded with 3 ul of harvested conditioned medium described above and placed on a plate containing the seeded microbial lawn. A positive control sample of a synthetic hBD-3 peptide (2-30 ug/ml) or an antibiotic such as streptomycin (100 ug/ml) is added to the conditioned medium and assayed, along with a negative control (unconditioned medium sample). After overnight incubation at 30° C., the inhibition zones are recorded using a ruler and if necessary a magnifying glass. The units of activity are read from a standard curve with the zones obtained by a dilution series for the synthetic β-defensin peptide (i.e., hBD-3 synthetic peptide). Garcia, J. R., et al., *Identification of a novel, multifunctional beta-defensin (human beta-defensin 3) with specific antimicrobial activity. Its interaction with plasma membranes of Xenopus oocytes and the induction of macrophage chemoattraction*. Cell Tissue Res, 2001. 306(2): p. 257-64. Antimicrobial potency is measured and compared to published standards (hBD-3 synthetic peptide or streptomycin). Ideally, the square of the diameter of the inhibition zone is proportional to the log of the concentration of an antibacterial factor. Frohm, M., et al., *Biochemical and antibacterial analysis of human wound and blister fluid*. Eur J Biochem, 1996. 237(1): p. 86-92. This cost effective assay is standardly used as a measure of antimicrobial activity, however it provides only semi-quantitative results of antibacterial activity.

A minimum inhibitory concentration (MIC) assay is also performed. The smallest amount of conditioned medium from NIKS cells transiently transfected with each of the β-defensin genes required to inhibit the growth of the test organism is determined. In this assay a series of culture tubes (or wells of a multi-well plate) containing bacterial growth medium with varying concentrations of NIKS conditioned medium is inoculated with the test organism. After an incubation period the turbidity is measured and the MIC is determined. Synthetic antimicrobial β-defensin peptides are used as positive controls. The MIC results are compared to those previously published by others (i.e., stimulated concentration range 15-70 ug/gm tissue or 3.5-16 uM. Harder, J., et al., *Mucoid Pseudomonas aeruginosa, TNF-alpha, and IL-1 beta, but not IL-6, induce human beta-defensin-2 in respiratory epithelia*. Am J Respir Cell Mol Biol, 2000. 22(6): p. 714-21. These relative ranges are only intended to provide guidance in an effort to achieve a reasonable point of reference.

Example 17

Organotypic Culture

This Example describes assays for hBD expression in organotypically cultured NIKS cells. Stable genetically-modified NIKS clones that demonstrate greater than two fold higher expression levels and enhanced antimicrobial activity over endogenous β-defensin gene expression in NIKS monolayer cultures are candidates of further characterization efforts. These efforts include preparing organotypic cultures to assess in vitro skin tissue for normal tissue morphology. A range of β-defensin expression levels are examined because expression levels that are too high may hinder the ability to obtain normal tissue morphology.

NIKS cell clones that exhibit several different increased β-defensin expression levels are used to prepare human skin substitute tissues using organotypic culturing techniques.

See, e.g., U.S. application Ser. No. 10/087,388; 10/087,346; 10/087,641 and PCT Application US 02/06088, all of which are incorporated herein by reference. The organotypic cultures consist of dermal and epidermal compartments. The dermal compartment is formed by mixing normal human neonatal fibroblasts with Type I collagen in Ham's F-12 medium containing 10% fetal calf serum and penicillin/streptomycin and allowing contraction. The epidermal compartment is produced by seeding NIKS cells on the contracted collagen gel in 25 µl of a mixture of Ham's F-12:DME (3:1, final calcium concentration 1.88 mM) supplemented with 0.2% FCS, 0.4 µg/ml hydrocortisone, 8.4 ng/ml cholera toxin, 5 µg/ml insulin, 24 µg/ml adenine, and 100 units/ml P/S. Cells are allowed to attach 2 hours at 37° C., 5% $CO_2$ before flooding culture chamber with media (day 0). On day 2 cells are fed with fresh medium. On day 4, cells are lifted to the air/medium interface on the surface of a media-saturated cotton pad, which allows the cultures to be fed from below. Organotypic cultures are incubated at 37° C., 5% $CO_2$, 75% humidity and are fed fresh medium every 2 days. By day 10, the NIKS cells stratify to form the basal, spinous, granular and cornified epidermal layers.

Histological sections of skin substitutes tissues formed by genetically modified NIKS cells are compared to cultures prepared from unmodified NIKS cells. Tissue sections are stained with hematoxylin and eosin to visualize the stratified epidermal layers. Cultures are examined for tissue morphology. Only those β-defensin-expressing clones that exhibit normal tissue organization and histology are used.

The organotypic cultures in the initial expression studies are prepared using cells expressing individual β-defensin transgenes. However, chimeric organotypic cultures ca be prepared by mixing NIKS cells overexpressing different β-defensins to achieve a broader range of antimicrobial activities. The cells expressing β-defensin transgenes can be used in conjunction with cells derived from a patient (See, e.g., U.S. Appl. 2002/0192196) or in conjunction with untransfected NIKS cells so that potency can be adjusted. This strategy provides further flexibility in protein expression profiles in skin tissue.

Example 18

Analysis of Stable hBD mRNA Expression in Organotypic Cultures

This Example describes assays for hBD mRNA. Total cellular RNA is isolated from whole tissue samples. This total RNA is used as a template for the subsequent first strand cDNA synthesis (reverse-transcriptase) reaction followed by the polymerase chain reaction (RT-PCR). Amplification products are resolved on an ethidium bromide stained agarose gel. The anticipated PCR products specific for the transgene DNA and mRNA product is 1.5 Kb and 720 bp respectively.

Example 19

Analysis of hBD Protein Expression in Organotypic Cultures

To monitor changes in β-defensin expression in cultured skin substitute tissue, media underlying the cultures are harvested at various times. When organotypic cultures are 10 days old, they are incubated for 48 hours in fresh medium. After 48 hours media is harvested every 12 hours for four days and the levels of β-defensin protein in the media is determined by ELISA and/or Western Blot analysis. A comparison is made to endogenous gene expression levels of cultured skin substitute tissues made with untransfected NIKS cells. In some experiments, tissue lysates are generated in order to detect β-defensin protein.

Example 20

Antimicrobial Analysis of Stable β-Defensin Clones in Organotypic Cultures Inhibition Zone Assay of Antimicrobial Activity To determine if human skin substitute tissue generated from β-defensin-expressing NIKS cells results in enhanced bactericidal activity, a modified in vitro inhibition zone assay is utilized. Both the conditioned medium and biopsy punches from 14, 21, and 28 day old skin substitute tissues are analyzed for antimicrobial activity. Briefly, thin (1 mm) agarose plates are seeded with a microbe of choice (*E. coli, S. aureus, P. aeruginosa, S. pyogenes* or *C. albicans*). The melted agarose (1%) contains Luria-Bertani broth with or without supplemented salt. The test organism, ($\sim 5 \times 10^4$ log-phase cells/ml) is added just before pouring the plate. To assay for β-defensin activity in conditioned medium from skin substitute tissues small wells (3 mm diameter) are punched in the assay plates and loaded with 3 ul of harvested culture medium conditioned for at least 24 hours by human skin substitutes generated with untransfected NIKS or NIKS clones stably expressing each β-defensin. Alternatively, discs may be loaded with 3 ul of harvested conditioned medium described above and placed on a plate containing the seeded microbial lawn. A positive control sample of a synthetic hBD-3 peptide (2-30 ug/ml) or an antibiotic such as streptomycin (100 ug/ml) will be added to the conditioned medium and assayed, along with a negative control (unconditioned medium sample). To assay the human skin substitute directly, four 8 mm punches are collected from each 44 $cm^2$ circular skin substitute tissue. As described above, each biopsy punch is homogenized (PowerGen Homogenizer), and placed on a plate containing the seeded microbial lawn. After overnight incubation at 30° C., the inhibition zones are recorded using a ruler and if necessary a magnifying glass. The units of activity are read from a standard curve with the zones obtained by a dilution series for the synthetic β-defensin peptide (i.e., hBD-3 synthetic peptide). Antimicrobial potency is measured and compared to published standards (hBD-3 synthetic peptide or streptomycin). Ideally, the square of the diameter of the inhibition zone is proportional to the log of the concentration of an antibacterial factor. Frohm, M., et al., *Biochemical and antibacterial analysis of human wound and blister fluid*. Eur J Biochem, 1996. 237(1): p. 86-92. This cost effective assay is standardly used as a measure of antimicrobial activity, however it will provide only semi-quantitative results of antibacterial activity.

Micro-broth Dilution Assay: A minimum inhibitory concentration (MIC) assay is performed. The smallest amount of conditioned medium and biopsy punches from 14, 21, and 28 day old skin substitutes from NIKS cells stably transfected with each of the β-defensin genes required to inhibit the growth of the test organism are determined. In this assay, a series of culture tubes (or wells of a multi-well plate) containing bacterial growth medium with varying concentrations of conditioned medium from skin substitute tissues is inoculated with the test organism. To assay the human skin substitute directly, four 8 mm punches are collected from each 44 $cm^2$ circular skin substitute tissue. As described above each biopsy punch is homogenized (PowerGen Homogenizer), and varying concentrations are incubated with the test organism. After an incubation period the turbidity is measured and the MIC is determined. Synthetic antimicrobial β-defensin peptides are used as positive controls. The MIC results are compared to those previously published by others (i.e., stimulated concentration range 15-70 ug/gm tissue or 3.5-16 uM. These relative ranges are only intended to provide guidance in an effort to achieve a reasonable point of reference.

Bacterial Growth Assay: To evaluate antimicrobial effects of β-defensins on microbes, cell culture supernatants from stable NIKS clones (either monolayer or organotypic cultures) will be evaluated for the ability to inhibit bacterial growth. Cell culture supernatants will be inoculated with approximately $4 \times 10^6$ c.f.u. of bacteria, in triplicate, and incubated for 1-4 hours at 37 degrees. Cell culture media supernatant collected from a native NIKS cell culture (i.e. non-genetically modified) will serve as an experimental control. NIKS cell culture supernatants spiked with purified β-defensin peptide titrations will be used as positive controls for antimicrobial activity. Immediately following the 1-4 hour incubation period, serial dilutions of each culture condition will be plated on LB/agar plates and incubated at 37 degrees for 18-20 hours. Triplicate plates for each serial dilution are assessed for colony forming units.

Example 21

Expression of Defensins in NIKS Cells

Figure 14:
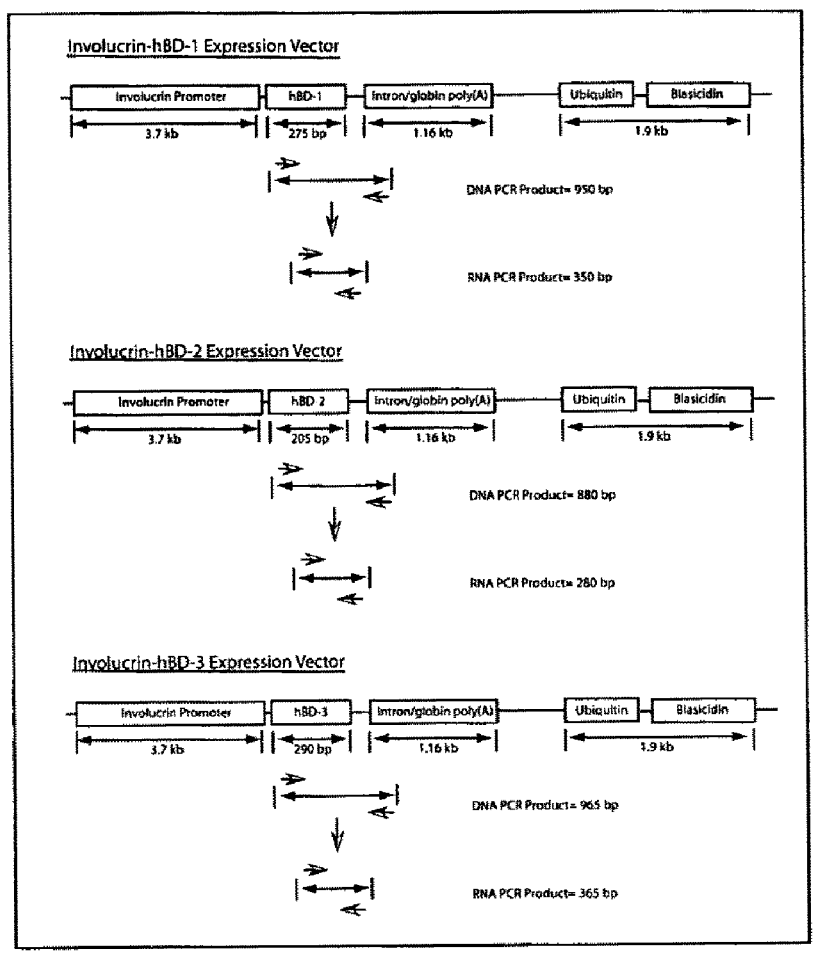
FIG. 14 describes expression vectors for expression of human β-defensin.

This example describes elevated β-defensin expression levels in transiently transfected NIKS cell monolayer cultures. Purified DNA from each of the Involucrin-β-defensin-Ub-Bsd vectors (FIG. 14) was introduced into NIKS cells using TransIt-Keratinocyte reagent (Mirus Corporation, Madison, Wis.). Mock transfected (no DNA) or empty vector (no β-defensin) transfected populations of NIKS cells were also analyzed for endogenous expression levels.

Figure 15:
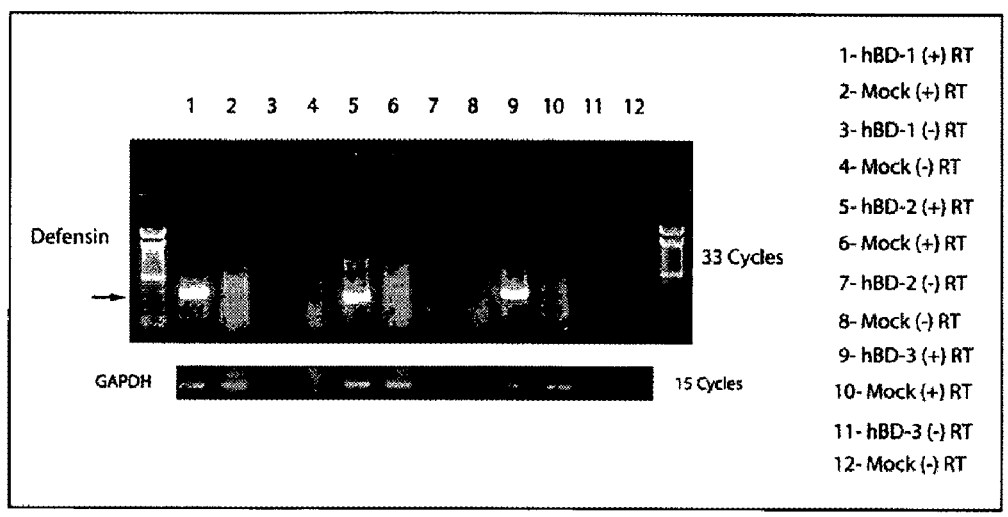
FIG. 15 provides the results of a RT-PCR assay for expression of human β-defensin mRNA.

Characterization of Transient β-Defensin Transgene Expression in Monolayer NIKS Cell Cultures Expression of β-defensin mRNA from the involucrin expression constructs was detected in transiently-transfected NIKS monolayer cell cultures by RT-PCR (FIG. 15). Primers were designed to amplify only the β-defensin transgene transcripts from the involucrin expression vectors and do not detect endogenous β-defensin expression mRNA. Also, to minimize amplification from DNA template, DNase treatment was performed on each of the total mRNA samples prior to the first strand cDNA synthesis (reverse transcriptase) reaction. β-defensin specific expression mRNA products (arrowhead) can be distinguished from PCR products amplified from expression vector DNA in that they lack the rabbit β-globin intron and are therefore 600 bp smaller than products amplified from DNA (see FIG. 14).

The ability to achieve expression of each β-defensin transgene was examined using transient transfections. NIKS keratinocyte monolayer cells ($1 \times 10^6$ per well) were transfected with the Involucrin-β-defensin-Ub-Bsd plasmid (10 μg) overnight using TransIT-keratinocyte reagent (Mirus Corporation, Madison, Wis.). A control mock transfection that contained NIKS cells without the addition of plasmid DNA was also included. One day post transfection, cells were collected. Total RNA was isolated using Trizol reagent (Invitrogen, Carlsbad, Calif.) and was analyzed by RT-PCR to monitor β-defensin gene expression from each of the Involucrin-β-defensin-Ub-Bsd constructs.

Results of the RT-PCR analysis of β-defensin gene expression are shown in FIG. 15. PCR primers were designed to amplify β-defensin mRNA expressed from the transgene construct, but not endogenous hBD mRNA. These primers also amplify DNA from the Involucrin-β-defensin-Ub-Bsd plasmids, but this product can be distinguished from the spliced mRNA product because it contains the rabbit β-globin intron and so is 600 bp larger than the spliced product (see FIG. 14). A prominent PCR product corresponding to spliced β-defensin mRNA (arrowhead) is detected for hBD-1, hBD-2 and hBD-3 (FIG. 15 lanes 1, 5, and 9 respectively). This product is not seen in control reactions lacking reverse transcriptase (FIG. 15 lanes 3, 7, and 11), demonstrating that it is derived from mRNA. These results also show that each of the hBD expression constructs is expressed in NIKS keratinocyte cell cultures.

Expression of Exogenous β-Defensin Protein in NIKS Cells

Culture medium from cells transiently transfected with each of the three β-defensin constructs was assayed for overexpression of protein by immunoblot analysis using anti-β-defensin antibodies specific for hBD-1, hBD-2 (Santa Cruz Biotechnology, Santa Cruz, Calif.) and hBD-3 (SAGE BioVentures, Carlsbad, Calif.).

Conditioned medium and cell lysates from transiently transfected monolayer of NIKS keratinocyte cultures were analyzed separately by SDS-PAGE under denaturing, reducing conditions and the levels of hBD-3 protein assessed by immunoblot analysis. Transient transfection of NIKS monolayer cultures was performed and one day post transfection, monolayer culture supernatants and cell lysates were collected as previously described for mRNA expression analysis. A BCA protein assay kit (Pierce, Rockford, Ill.) was used to establish a predetermined amount of protein to be loaded into each well of a 16% Tricine Novex pre-cast gel (Invitrogen, Carlsbad, Calif.) and then electroblotted onto a PVDF (0.2 μm pore size) filter. After blocking with 4% skim milk in phosphate-buffered saline for 1 hour, the filter was incubated overnight with a rabbit polyclonal antibody purified against amino acid residues 23-33 of the human β-defensin-3 protein (1:500). The filter was then incubated with goat anti-rabbit IgG horseradish peroxidase-conjugated secondary antibody (1:5000) for 1 hour. Products were detected by incubating blots with enhanced chemiluminescence (ECL) immunoblotting detection system (Amersham Pharmacia Biotech, Sunnyvale, Calif.) and exposing to film.

The anticipated product size of hBD-3 protein is 5 kDa. However recent studies have reported that hBD-3 protein exhibits a molecular weight of approximately 14 kDa, consistent with the formation of a dimer (Schibli, D. J., et al., J Biol Chem, 2002. 277(10): p. 8279-89). This difference in weight may be in part explained by post-translational modification of proteins (i.e., glycosylation) or is due to dimers of hBD-3 present as a result of non-reduced disulfide bonds. Synthetic, control hBD-3 (90 ng) was detected by immunoblot analysis (FIG. 16, lane 1). hBD-3 protein of the expected molecular weight (5 kDa or 14 kDa) was not detected in conditioned medium harvested from transfected or mock (untransfected) NIKS (see FIG. 16, lanes 4 & 5). The presence of the high molecular weight band observed in lanes 4 and 5 appears to be dependent on the presence of serum in the conditioned medium. Only a very faint high molecular weight band was observed in serum-free conditioned medium harvested from transfected or mock (untransfected) NIKS keratinocytes.

Figure 16:
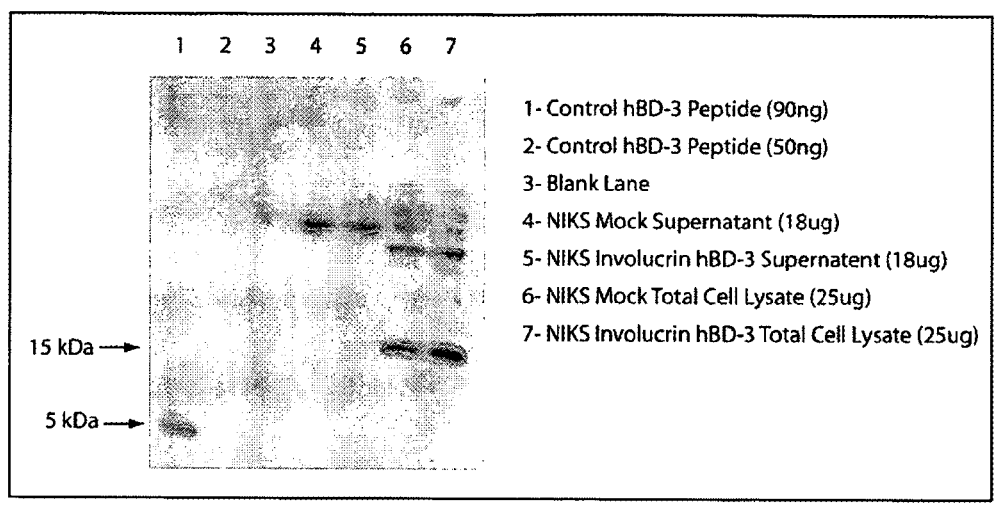
FIG. 16 provides the results of immunoblot detection of human β-defensin protein.

A 14 kDa protein recognized by the anti-hBD-3 antibody in cell lysates from both transiently transfected and mock transfected NIKS cell lysates was detected (FIG. 16, lanes 6 and 7). NIKS transiently transfected with the hBD-3 transgene produce increased levels of hBD-3 protein. These cell lysate results indicate that, although hBD-3 protein is over-expressed in transiently-transfected NIKS cells, it remains associated with the cells or extracellular matrix and does not appear to be secreted into the medium. The secretory signals for the granules that contain sequestered β-defensin peptide appear to be tightly associated with late stages of squamous differentiation (Oren, A., et al., Exp Mol Pathol, 2003. 74(2): p. 180-2).

Example 22

Figure 17:
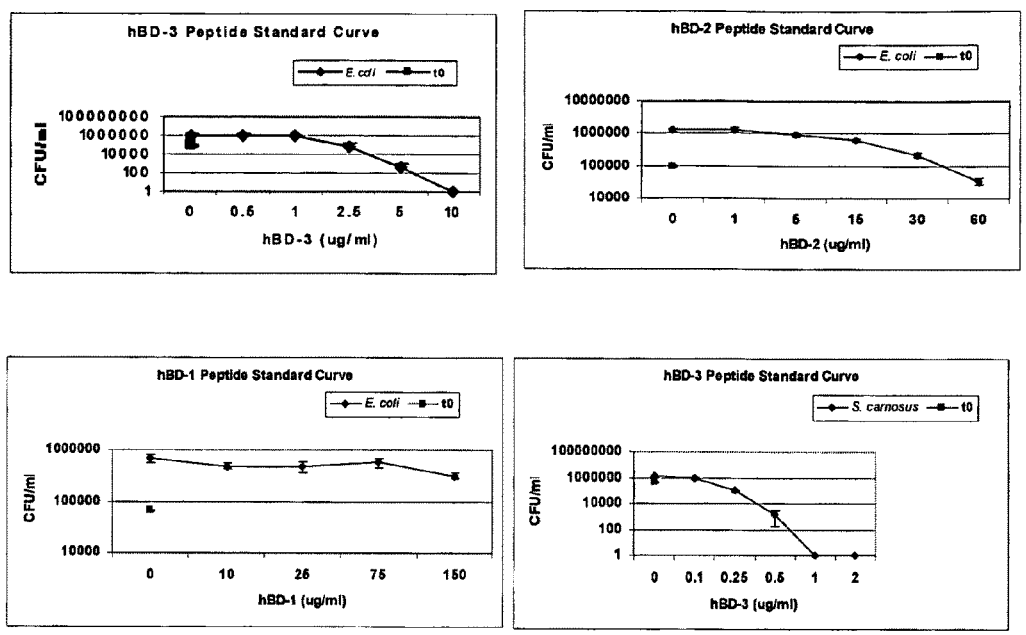
FIG. 17 shows the antimicrobial activity of human β-defensins 1, 2, and 3.

Antimicrobial Activity of β-Defensin in Transiently Transfected NIKS Cell Monolayer Cultures This Example describes antimicrobial activity of defensins in cell culture.
Development of an Antimicrobial Assay Used to Detect Biological β-Defensin Activity
The antimicrobial activity assay employed *Escherichia coli* and *Staphylococcus carnosus* and is a modification of the protocol described by Porter and coworkers (Porter, E. M., et al., Infect Immun, 1997. 65(6): p. 2396-401). Briefly, gram-positive or gram-negative bacteria are grown overnight. The following day the test organisms are subcultured for 2.5 hr and working dilutions of $10^4$ bacteria/ml for *Escherichia coli* or $10^5$ bacteria/ml of *Staphylococcus carnosus* in 10 mM sodium phosphate (pH 7.4)-1% TSB are created. All the reactions mix 50 µl of experimental reagent (lysis, supernatants or purified protein) with 50 µl of bacterial suspension. These reactions are then incubated at 37° C. for 1.5 hr. The reactions are diluted 100-fold in 10 mM sodium phosphate (pH 7.4)-1% TSB and plated on TSB plates using a spiral plater (Spiral Biotech, Norwood, Mass.). The plates are then incubated for 12 to 16 hr at 37° C. Colonies on these plates are counted and the number of viable bacteria is determined and expressed as colony forming units per milliliter (CFU/ml).
Standard Curves for Antimicrobial Activity of Synthetic hBD-1, hBD-2 and hBD-3 Peptides
Standard curves for the antimicrobial activity of hBD-1, hBD-2, and hBD-3 are shown in FIG. 17. Among the hBD proteins, hBD-3 exhibited the most antimicrobial activity with the concentration necessary to kill 50% ($LC_{50}$) of *E. coli* at 2.4 µg/ml (FIG. 17a). Both hBD-2 and hBD-1 were less potent than hBD-3 against *E. coli* (FIG. 17b and c). hBD-2 had an $LC_{50}$ of 12.2 µg/ml for *E. coli* and hBD-1 had an $LC_{50}$ of 102 µg/ml. The gram-positive bacteria, *S. carnosus*, appears to be even more sensitive to hBD-3 with an $LC_{50}$ of 0.19 µg/ml (FIG. 17d).
Neither conditioned medium nor cell lysates from monolayer cultures of NIKS cells transiently transfected with hBD transgenes or controls exhibited antimicrobial activity in the antimicrobial assay. Endogenous expression of hBD-2 and hBD-3 is observed only in organotypic cultures of NIKS keratinocytes not monolayer cultures. Therefore, the monolayer culture conditions compromise the ability to use transient expression experiments to assay for antimicrobial activities of the hBD-2 and hBD-3 proteins. Although hBD-1 is expressed in monolayer and organotypic cultures of NIKS keratinocytes, hBD-1 exhibits the lowest antimicrobial activity in test organisms. In addition, it is possible that the transient transfection efficiency of NIKS cells, which is generally 20-30%, may not be sufficient to support the hBD levels necessary to exhibit antimicrobial activity. These findings led us to the generation of clones of NIKS keratinocytes stably expressing an hBD transgene and to conducting antimicrobial activity assays using organotypic cultures of these NIKS clones.

Isolation of Stably Transfected NIKS Keratinocytes
Based on the lack of antimicrobial activity observed in the transiently transfected NIKS keratinocytes, stably-transfected NIKS clones expressing hBD transgenes were isolated. The present invention is not limited to a particular mechanism. Indeed, an understanding of the mechanism is not necessary to practice the present invention. Nonetheless, it is contemplated that higher levels of hBD expression would be achieved in clones stably-transfected with the hBD transgenes. In addition, it was observed that both endogenous hBD mRNA and protein levels were enhanced by organotypic culture NIKS keratinocytes and that stratification and/or late stage differentiation events associated with the development of barrier function may be necessary for hBD processing or secretion. Transiently transfected NIKS keratinocytes cannot be assayed following organotypic culture because full stratification and barrier function requires at least 11 days to develop and transient expression of hBDs would be exhausted.
Stable clones of NIKS keratinocytes expressing hBD-3 were first generated. hBD-3 was selected because it demonstrates the most potency against the two test organisms and exhibits antimicrobial activity against both gram positive and gram negative bacteria. Multiple independent clones expressing the hBD-3 transgene were obtained by transfecting NIKS cells and selecting stably-transfected cells using growth medium containing blasticidin (2.5 µg/ml). Elevated β-defensin mRNA expression was verified using RT-PCR analysis of total RNA isolated from each NIKS clonal cell line and served as an initial screen for relative expression levels between different clones.
NIKS clones stably expressing the hBD-3 transgene have been isolated and screened. To quantify relative β-defensin expression levels in stably-transfected NIKS Involucrin-Defensin-3-Ub-Bsd clones, total cellular RNA was isolated from blasticidin-resistant clones. RT-PCR analysis was performed on all blasticidin-resistant NIKS clones transfected with the Involucrin-Defensin-3-Ub-Bsd expression construct.
Conditioned Medium from Organotypic Cultures of NIKS™ Clones Stably Expressing the hBD-3 Transgene Exhibit Enhanced Antimicrobial Activity
The antimicrobial activity of conditioned medium harvested from organotypic cultures of the stably-transfected NIKS keratinocyte clone expressing the highest level of hBD-3 mRNA was assayed using the method described above. FIG. 18 shows that 70% of the *E. coli* and up to 52% of the *S. carnosus* bacteria were killed following exposure to conditioned medium from organotypic cultures of NIKS keratinocytes stably expressing the hBD-3 transgene when compared to conditioned medium harvested from organotypic cultures generated from untransfected NIKS keratinocytes. Conditioned medium from control NIKS organotypic cultures exhibit detectable, but low levels of antimicrobial activity, consistent with a link between squamous differentiation and endogenous hBD-3 expression (Abiko, Y., et al., J Dermatol Sci, 2003. 31(3): p. 225-8.).

Example 23

Defensin Mutants

This example describes site-directed mutagenesis of hBD3. Five (5) of six Cys were mutated to Ala (i.e., $Cys_{40}$, $Cys_{45}$, $Cys_{55}$, $Cys_{62}$, $Cys_{63}$). In another mutant, $Gly_{38}$ is mutated to $Ala_{38}$).

Site-Directed Mutagenesis—

A commercially available kit, QUIKCHANGE Multi Site-Directed Mutagenesis kit (Stratagene, LaJolla, Calif.) was used to create amino acid substitutions in the native hBD-3 polypeptide. The hBD-3 cDNA TopoTA DNA vector was used as the parental DNA template for the site-directed mutagenesis reactions using the manufacturer specifications. Briefly, a thermocycling reaction included—double stranded DNA template, two or more synthetic phosphorylated oligonucleotide primers that contain the desired mutation(s), enzyme blend containing PfuTurbo DNA polymerase. First the mutagenic primers are annealed to the denatured DNA template. PfuTurbo DNA polymerase was used to extend the mutagenic primer(s) generating double stranded DNA molecules with one strand bearing the wanted mutation(s). In Step 2, the thermocycling reaction products were treated with Dpn I restriction endonuclease. The Dpn I endonuclease is specific for methylated and hemimethylated DNA and is used to digest parental DNA template. DNA isolated from almost all *E. coli* strains is dam methylated and therefore susceptible to this digestion. In Step 3, the reaction mixture, enriched for mutated single stranded DNA is transformed into ultracompetent cells (dam+), where the mutant closed circle ss-DNA is converted to duplex form in vivo. Double stranded plasmid DNA is prepared from the transformants and clones are identified that contain the wanted mutation(s).

Synthetic phosphorylated oligonucleotide primers—The mutated codon sequence is underlined.

1) Gly$_{38}$→Ala mutation oligonucleotide sequence

```
                                          (SEQ ID NO: 115)
(ST262)
5'-Phos-GCA GAG TCA GAG GCG CCC GGT GTG CTG TGC

TCA GC-3'
```

2) Cys$_{(40,45,55,62,63)}$→Ala mutation oligonucleotide sequences

```
                                          (SEQ ID NO: 116)
(ST258) 5'-Phos-CCTCCTTTGGAAGGGCGCTGAGCACAGC

AGCCCGGCCGCC-3'

(SEQ ID NO: 117)
(ST259) 5'-Phos-CTTTCTTCGGGC GGCTTTTCGGCCACGCGTCGA

GGCCTTGCCGATC-3'
```

Final mutant amino acid sequences—The site-directed substitutions are highlighted.

1) Amino Acid Sequence (Gly38→Ala)

```
                                          (SEQ ID NO: 118)
MRIHYLLFALLFLFLVPVPGHGGIINTLQKYYCRVRGARCAVLSCLPKEE

QIGKCSTRGRKCCRRKK
```

2) Amino Acid Sequence (5Cys→Ala)

```
                                          (SEQ ID NO: 119)
MRIHYLLFALLFLFLVPVPGHGGIINTLQKYYCRVRGGRAAVLSALPKEE

QIGKASTRGRKAARRKK
```

Expression Vector Constructs—

| Involucrin promoter | hBD-3 mutant cDNA | Globin poly(A) |

Electroporation Transfection Method—Early passage NIKS cells were harvested at @ approximately 50-70% confluence. Cells were pelleted and the pellet resuspended ($1\times10^6$-$3\times10^6$ cells/800 ul) in F-12/DME (5:1).

800 ul of NIKS cell suspension was placed in 0.4 cm electroporation cuvette, DNA was added (10-30 ug, linear or supercoiled), placed in cuvette holder of the GenePulser and started. All steps were done at room temperature; the cells were not placed on ice at any time during this procedure. The actual voltage and capacitance values were recorded Electroporated NIKS cells were removed from the cuvette and diluted into 25-50 mls of fresh NIKS medium, mixed well by pipetting, and plated (5-10 mls) per p150 containing blasticidin resistant feeders (using either 5 or 10 p150's per transfection reaction).

In the next 24-48 hours, the medium is replaced on the p150's with blasticidin containing medium (2.5 ug/ml blasticidin).

BioRad GenePulser Electroporation Settings:
Exponential Pulse Program
270 volts
950 uF
∞ ohms
0.4 cm cuvette Selection—NIKS keratinocyte clones were cocultured in the presence of blasticidin resistance feeder cells and selected for growth in presence of NIKS medium containing 2.5 ug/ml blasticidin. Only those colonies that continued to grow in the presence of blasticidin selection for duration of selection (a minimum of 18 days) were isolated and expanded for further characterization.

Clone Isolation—A traditional "Ring cloning" method is to isolate blasticidin resistant colonies. The clones are first picked onto a feeder layer in individual plates (p60) and allowed to grow until they are between 80-90% confluent. The clones are then passed and re-plated to two individual tissue culture plates (p60 and p100). The p100 contains mouse fibroblast feeder cells and the p60 does not. When these cultures reach 80-90% confluence, the p60 cultures are harvested for expression analysis and the p100 cultures are used for the subsequent expansion phase.

Characterization of Stably-transfected NIKS keratinocytes—Stable NIKS keratinocyte colonies that survived the selection scheme therefore are presumed to contain the Involucrin hBD-3 expression construct. To confirm the presence of the hBD-3 transgene, RNA was isolated from each clone and cDNA products were generated using reverse transcription (RT). The RT products were then used as templates in subsequent PCR reactions. This PCR screen was designed to reconcile products derived from transgene cDNA from that of potential endogenous hBD-3 DNA products. Multiple clones were obtained using the hBD-3 constructs (Gly38→Ala substitution and 5 Cys→Ala substitution) and associated selection scheme.

Expansion—The results of expression analysis obtained from the p60 cultures dictate which clones were expanded for further characterization. The p100 plates from cultures identified as having positive expression were grown to approximately 90% confluence then harvested and frozen at −80° C. in media containing 10% glycerol.

Results are shown below.

| Experiment # | (Clones picked/Positive) |
|---|---|
| Exp 1-Gly→ Ala* | 10/10 |
| Exp 2-Gly→ Ala | 14/16 |
| Exp 3-Gly→ Ala | 11/11 |
| Cys→ Ala** | 0/2 |
| Exp 4-Cys→ Ala | 2/2 |
| Exp 5-Cys→ Ala | 4/4 |
| Exp 6-Cys→ Ala | 3/3 (two more yet to be screened) |
| Exp 7-Cys→ Ala | 25/26 (five clones yet to be screened) |

*Mutant construct (Gly→ Ala)-hBD-3 amino acid substation
**Mutant construct (Cys→ Ala)-hBD-3 amino acid substation five of six cysteines to alanines.

Example 24

Design and Construction of hCAP18 Expression Vectors

This example describes the design and construction of human cathelicidin (hCAP18) mammalian expression vectors.

The human cathelicidin (hCAP18) cDNA was cloned from a commercially available human cDNA library. PCR products were amplified sequenced to confirm the genetic identity. This hCAP18 cDNA sequence was confirmed to be identical to that sequence deposited in Genbank for hCAP18.

Two hCAP18 mammalian expression vectors were generated. The first vector contains the tissue specific kertain-14 promoter, and the second vector utilizes the involucrin promoter as an alternative promoter strategy. A linear map and diagnostic digests of the hCAP18 mammalian expression vectors are shown in FIG. 19. The diagnostic restriction enzyme digests demonstrate correct banding patterns of the appropriate sizes. Taken together these results account for the overall integrity of the mammalian expression constructs. Sequencing across all of the cloning junctions on both final assembled constructs (K14 hCAP18 and involucrin hCAP18) was also performed to verify the sequence integrity of each expression vector.

Expression of hCAP18 from Expression Constructs

Figure 20:
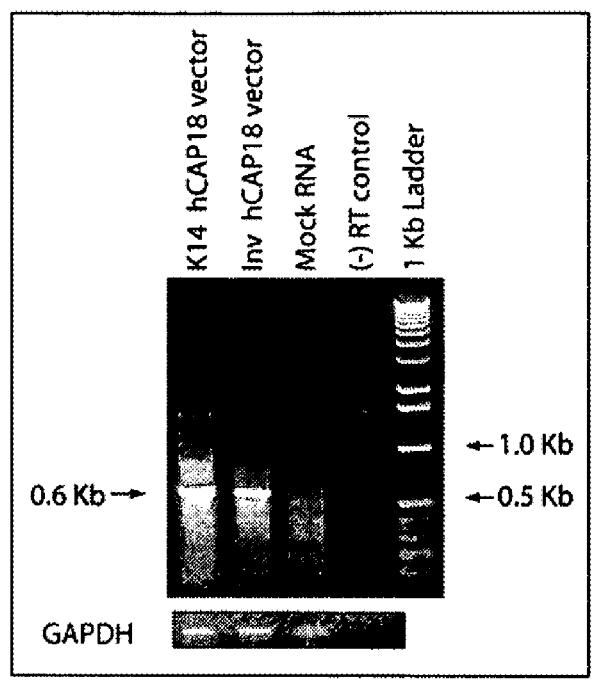
FIG. 20 shows the results of a RT-PCR assay for expression of hCAP18.

RT-PCR analysis was conducted to verify overexpressed levels of hCAP18 from both expression constructs (FIG. 20). Reverse transcriptase reactions were performed on monolayer NIKS cell cultures transiently transfected with each of the human cathelicidin expression vectors or mock transfected. The anticipated PCR product size of 0.6 kb corresponding to hCAP18 is shown in transfected cells and as expected this hCAP18 product is not seen in RNA from Mock transfected monolayer NIKS cell cultures. An additional set of PCR primers specific for an endogenous house keeping gene (GAPDH) was used on the RT reactions to control for RNA integrity and first strand cDNA synthesis reactions.

Example 25 hCAP18/LL-37 Antimicrobial Activity

This example describes the development of an assay to detect LL-37 antimicrobial activity. In developing this assay a standard kill curve was produced using a commercially available LL-37 peptide (Phoenix Pharmaceuticals, Belmont, Calif.). The assay is a modification of the antimicrobial assay developed to assess biological activity of other antimicrobial peptides described above. A standard curve for the antimicrobial activity of LL-37 was determined for gram-positive bacteria, *S. carnosus* using this synthetic peptide. Results indicated that LL-37 exhibited potent antimicrobial activity with a concentration necessary to kill 50% ($LC_{50}$) of the *S. carnosus* at 0.9 ug/ml.

Example 26

Electroporation of Cells

This Example describes the use of electroporation to introduce nucleic acids into keratinocytes. This Example further describes the use of electroporation to select for pluripotent and multipotent cells in a population.

Protocol:

Harvest early passage NIKS cells @ approximately 50-70% confluence. Pellet cells and resuspend NIKS cell pellet ($2 \times 10^6$ cells/800 ul) in F-12/DME (5:1). This same protocol electroporating $1 \times 10^6$ NIKS cells in 800 ul with the same success.

Place 800 ul of NIKS cell suspension in 0.4 cm electroporation cuvette, add DNA (10-30 ug, linear or supercoiled) place in cuvette holder of the GenePulser and push button. All steps are done at room temperature; the cells are not placed on ice at any time during this procedure. Record actual voltage and capacitance values (these values are indicative of reproducible electroporation experimental conditions and may be useful for future reference).

Electroporated NIKS cells are removed from the cuvette and diluted into 25-50 mls of fresh NIKS medium, cells are mixed well by pipetting, and plated (5-10 mls) per p150 containing blasticidin resistant feeders (using either 5 or 10 p150's per transfection reaction).

The following day replace medium on the p150's with blasticidin containing medium (2.5 ug/ml blasticidin). Clonal selection of NIKS keratinocytes is typically carried out for 18-20 days in blasticidin media (with fresh medium changes every other day).

The traditional electroporation conditions for mammalian cells as provided by the manufacturer (BioRad) are described below. These conditions need to be optimized; they are equipment specific and cell type specific.

Electroporation Medium recommended to be minimal or TE at 0.5-0.8 mls.

| | |
|---|---|
| Cell Density (single cell suspension) | $6\text{-}8 \times 10^6$ |
| Volume of Cells | 0.4-0.8 mls |
| DNA | 20-200 ug |

Gene Pulser (BioRad) Technical Services Recommended Ranges Using an Exponential Protocol.

| Gene Pulser Settings | |
|---|---|
| Voltage (V) | 200-350 |
| Capacitance (μF) | 500-1000 |
| Resistance (Ω) | ∞ |
| Cuvette (mm) | 0.4 |

Experiments conducted resulted in the following optimized protocol for electroporation:

| Cell Density (single cell suspension) | 1-2 × 10⁶ |
|---|---|
| Volume of Cells* | 0.8 mls |
| DNA** | 10-20 ug |

*F-12/DME minimal medium (50 mls:10 mls)
**Linear or supercoiled DNA (Qiagen Maxiprep DNA purification) All steps performed at ambient temperature Gene Pulser Settings

| Voltage (V) | 270 |
|---|---|
| Capacitance (μF) | 950 |
| Resistance (Ω) | ∞ |
| Cuvette (mm) | 0.4 |

The above protocol was used to select for cells in a populations of cells that have stem-cell-like keratinocyte populations. In some embodiments, a drug selection cassette was electroporated. In other embodiments, the cells are electroporated in the absence of any exogenous nucleic acids. The results are described below.

I. Clonally selected cell population observations (Drug selection cassette containing DNA electroporated and cell populations under drug selection for >18 days):
  1) Selected for keratinocytes having holoclone or meroclone cell morphology-colony morphology of tightly packed, uniform cells, smooth colony edges, overall round colony morphology.
  2) Selected for cells with stem-cell-like properties
  3) Selected for cells that exhibit extended proliferative capacity—in creation of stable cell lines, these colonies are typically the only surviving colonies after >18 days under drug selection pressure.
  4) Selected for cells with enhanced pluripotency or multipotency.
  5) Colonies without holoclone or meroclone morphology remain smaller and tend to stop growing. These colonies do not share the same characteristics as does the small tightly packed uniform cells within each large colony. These colonies die-off and most detach from the plate during the selection process.

II. Electroporation population observations (Exposed to electroporation conditions w/o DNA and not placed under selection):
  1) Selected for keratinocytes having holoclone or meroclone cell morphology-colony morphology of tightly packed, uniform cells, smooth colony edges, overall round colony morphology.
  2) Selected for cells with stem-cell-like properties
  3) Selected for cells that exhibit extended proliferative capacity—these colonies are typically the larger surviving colonies
  4) Selected for cells with enhanced pluripotency or multipotency.
  5) Colonies without holoclone or meroclone morphology remain smaller and tend to stop growing. These colonies do not share the same characteristics as does the small tightly packed uniform cells within each large colony.

The results of this experiment demonstrated that populations of cell can be electroporated with or without exogenous nucleic acid and cells with the above described properties are selected for. In addition, Transgene expression from NIK stable clones obtained using the electroporation method of selection have higher expression levels when compared to those clones obtained using the Trans-IT keratinocyte (Minis) transfection method as demonstrated with semi-quantitative RT-PCR analysis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, biochemistry, or related fields are intended to be within the scope of the following claims.

We claim:

1. A method of treating wounds comprising:
a) Providing an organotypic human skin equivalent comprising stratified squamous epithelia produced from immortalized human keratinocytes stably transfected with a vector comprising a nucleotide sequence encoding cathelicidin polypeptide and the nucleotide sequence is operably linked to a promoter sequence selected from the group consisting of the involucrin promoter and the keratin-14 promoter, and a human subject with a wound;
b) contacting said wound with said organotypic human skin equivalent comprising stratified squamous epithelia produced from immortalized keratinocytes expressing the exogenous cathelicidin polypeptide.

2. The method of claim 1, wherein said contacting comprises a technique selected from the group consisting of topical application, engraftment and wound dressing.

3. The method of claim 1, wherein said wounds are selected from the group consisting of venous ulcers, diabetic ulcers, pressure ulcers, burns, ulcerative colitis, mucosal injuries, internal injuries, and external injuries.

4. The method of claim 1, wherein said keratinocytes are NIKS cells.

5. The method of claim 1, wherein said human skin equivalent further comprises keratinocytes from a patient.

* * * * *

SEQUENCE LISTING

```
<160> NUMBER OF SEQ ID NOS: 128

<210> SEQ ID NO 1
<211> LENGTH: 27
<212> TYPE: DNA
<213> ORGANISM: Artificial Sequence
<220> FEATURE:
<223> OTHER INFORMATION: Synthetic

<400> SEQUENCE: 1
aagcttatat tccatgctag ggttctg                                27

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
ggtgcagagg agggaggtga gcga                                   24
```

<210> SEQ ID NO 3
<211> LENGTH: 1767
<212> TYPE: DNA
<213> ORGANISM: Artificial Sequence
<220> FEATURE:
<223> OTHER INFORMATION: Synthetic

<400> SEQUENCE: 3

| | | | | | |
|---|---|---|---|---|---:|
| aagcttatat | tccatgctag | ggttctggtg | ttggtgcgtg | ggttggggt | 60 |
| aattcgccct | taagattata | ttccatgcta | gggttctggt | gttggtgcgt | 120 |
| tgggactgca | gaagtgcctt | ttaagattat | gtgattgact | gatctgtcat | 180 |
| ccatctttat | cttttggatt | ccctcggag | aggggagg | aaggagttc | 240 |
| tattgaatga | aatgaaaggg | aaagtagagc | tgttcctatg | tcccgggctc | 300 |
| attcctgatc | cctgcataag | aaggagacat | ggtggtggtg | gtggtgggtg | 360 |
| ggcacagagg | aagccggtac | tgggctctgc | accccattcc | cgctcccaga | 420 |
| cacagcattt | ttctccagtg | agcacagcct | cccttgccc | cacagccaac | 480 |
| ctcccaacaa | aagcatctgt | ccctcagcca | aaaccctgt | tgcctctctc | 540 |
| gtagggctgg | gccagggtgg | ggggaccatt | ctctgcaggg | agattaggag | 600 |
| gggcgggtgg | agcggggtgg | ggccctggct | tactcacatc | cttgagagtc | 660 |
| agatttgggg | agcccacagc | tcagatgtct | gtctcagcat | tgtcttccaa | 720 |
| cacagtagtg | gggggctccc | ttctctggct | tcttctttgg | tgacagtcaa | 780 |
| ggggtgacag | agggtcctgc | ttctgtacta | ggagcagttg | atcccaggaa | 840 |
| gcctccagca | ggggctgttg | gggcctgtct | gaggagatag | gatgcgtcag | 900 |
| acacgttcac | attcctctca | acatgcctgc | cggggtctgt | ggagcctagg | 960 |
| agggtgggt | ggggccgga | agggtttgct | tcgggaggtt | gtctgggaga | 1020 |
| tttgatatac | acacctccaa | agcaggacca | agtggactcc | tagaaatgtc | 1080 |
| tggggcttca | ggagtcaggg | accctcgtgt | ccacctcacc | ttgcccttgg | 1140 |
| ctccactcca | gcctctactc | ctccccagaa | catctcctgg | gccagttcca | 1200 |
| aaacgagggc | gcctgagctg | ccacactagg | gatgttctgg | gggtctgaga | 1260 |
| ggctggaaga | ataaaaggcc | ccctaggcct | gttcctggat | gcagctccag | 1320 |
| gctaagcctg | ggctataaca | atgccaacga | ggcttcttgc | catactcggt | 1380 |
| cttttcacata | cattgtcgca | ttggattctc | agagctgact | gcactaagca | 1440 |
| tatgactccc | actttgcaga | tgagaacact | gaggctcaga | gaagtgccaa | 1500 |
| acagaggcgt | aaatggcaga | gccaggaccc | acctgactcc | aggctggttc | 1560 |
| tgaggccacc | tgccctatgg | tgtggttgat | gtgagatcct | caccataggg | 1620 |
| ggtctgtgct | cagggatggg | gagggcttgc | tggatttctc | tttgatgggg | 1680 |
| gggaatcacg | atacacctga | ctagctgggt | gtatttcagg | gatgggacag | 1740 |
| acagcatggg | aggtcaggcc | tgggagg | | | 1767 |

<210> SEQ ID NO 4
<211> LENGTH: 30
<212> TYPE: DNA
<213> ORGANISM: Artificial Sequence
<220> FEATURE:
<223> OTHER INFORMATION: Synthetic

<400> SEQUENCE: 4

```
cgcggatccg cgatgtggaa atggatactg                                       30

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
gggatatcct atgagtgtac caccattgga                                       30

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
tgctgttctt ggtgtcttcc g                                                21

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
caaccagcac gttgcccagg                                                  20

<210> SEQ ID NO 8
<211> LENGTH: 50
<212> TYPE: DNA
<213> ORGANISM: Artificial Sequence
<220> FEATURE:
<223> OTHER INFORMATION: Synthetic

<400> SEQUENCE: 8
tgttaccaat ctgaagtggg agcggccgcc cttttttttt tttttttttt                  50

<210> SEQ ID NO 9
<211> LENGTH: 322
<212> TYPE: DNA
<213> ORGANISM: Homo sapiens

<400> SEQUENCE: 9
gtcagctcag cctccaaagg agccagcctc tccccagttc ctgaaatcct gagtgttgcc       60
tgccagtcgc catgagaact tcctaccttc tgctgtttac tctctgctta cttttgtctg      120
agatggcctc aggtggtaac tttctcacag gccttggcca cagatctgat cattacaatt      180
gcgtcagcag tgagggcaa tgtctctatt ctgcctgccc gatctttacc aaaattcaag       240
gcacctgtta cagagggaag gccaagtgct gcaagtgagc tgggagtgac cagaagaaat      300
gacgcagaag tgaaatgaac tt                                               322

<210> SEQ ID NO 10
<211> LENGTH: 319
<212> TYPE: DNA
<213> ORGANISM: Homo sapiens

<400> SEQUENCE: 10
ggtgaagctc ccagccatca gccatgaggg tcttgtatct cctcttctcg ttcctcttca       60
```

```
tattcctgat gcctcttcca ggtgttttg gtggtatagg cgatcctgtt acctgcctta    120
agagtggagc catatgtcat ccagtctttt gccctagaag gtataaacaa attggcacct    180
gtggtctccc tggaacaaaa tgctgcaaaa agccatgagg aggccaagaa gctgctgtgg    240
ctgatgcgga ttcagaaagg gctccctcat cagagacgtg cgacatgtaa accaaattaa    300
actatggtgt ccaaagata                                                 319

<210> SEQ ID NO 11
<211> LENGTH: 266
<212> TYPE: DNA
<213> ORGANISM: Homo sapiens

<400> SEQUENCE: 11
catccagtct cagcgtgggg tgaagcctag cagctatgag gatccattat cttctgtttg     60
ctttgctctt cctgttttg gtgcctgttc caggtcatgg aggaatcata aacacattac    120
agaaatatta ttgcagagtc agaggcggcc ggtgtgctgt gctcagctgc cttccaaagg    180
aggaacagat cggcaagtgc tcgacgcgtg gccgaaaatg ctgccgaaga agaaataaa    240 aaccctgaaa catgacgaga gtgttg                                        266

<210> SEQ ID NO 12
<211> LENGTH: 3726
<212> TYPE: DNA
<213> ORGANISM: Homo sapiens

<400> SEQUENCE: 12
aagcttctcc atgtgtcatg ggatatgagc tcatccttat tatgttgggt gggggttgga     60
cagttaccca gacttgtcat gtggacctgg agcttatgag gtcattcaca taggcagtga    120
aagaacctct cccatatacg tgaatgcctg tctcccaaat ggggcaacct gtgggcagaa    180
taagggactt ctcagcccta gaatgttgag gtttccccaa cccctccctt gcatacacac    240
acacacaaac actccctcag ctgtatccac tgccctcttt cccacaccct agctttgccc    300
agcagtcaaa ggctcacaca taccatcttc tccttaaggc tcttattatg ccgtgagtca    360
gagggcggga ggcagatctg gcagatactg agcccctgct aacccataag accggtgtga    420
cttccttgat ctgagtctgc tgccccagac tgactgtcac gggctgggaa gaggcagatt    480
ccccccagat gaagtcagca gcagagcaca agggcatcag cgccaaagta aggatgcttg    540
attagttctt cagggcagag tgggctgtgc ttcctctgcc ccagaaaatg gcacagtccc    600
tgttctatgg gaaaaagaat gtgaggtccc tgggtgggct cagggaacag agaggtcatg    660
aggaggggat agcactgcag aaaccaaggg tgccttgtga gtcctccctc tgtctttta    720 ggcatgatcc aggaacatga caaaattagt gctttaaata gatttacttg gggctaagag    780
aaatgtgcct gtcaggaaaa ctatggggaa tcaggacact tctcaaaatt agccccactg    840
agtattgtct ttataattcc ttctttttgg attagattgt aaaaagaga gtgtaaatga    900 atgatgtcca tataataagt tattagccaa ccattaaaaa gaagggaag aaataaatca    960 gtttggtttt tacacacaca tacagacaca cacatataaa cattgatcaa cactgaaatg   1020
tttaatagtc attattttcg ggtcgtaaaa ttcactgttc ttcaatgaat acttgtagag   1080
cacatattat atgcagtagt tttgataggt tctaggggta tagtgaaaaa cataccaggt   1140
atacgctgct cttagcttat tttccagtgg gaaagataga caataagcaa gtgaacaaat   1200
gcaaataaat tactctagat tgttataagt gaaattaagt accaatcctt tagatatggt   1260
acacagagaa ggatctctga cagaccccaa cattgacact gaagctgaaa ggcataaaag   1320
```

```
aaccagagac ctggggaggg gccggtgggc agaaggagag caggtgccaa gcccccaggt    1380
ggagagctct gggctcatct caggaaccga aggccctcag tgaggtaaga atatacctct    1440
cagggagaga ttgacatgaa ttggggcccc agaagaaggc agaagccagg tacccagggt    1500
cttttaaacc acggcagtga gtttgaatgt tatttcaagt gtgctggtgc actgttggca    1560
cgggggagag atgtgctcaa atccccactc tgaaagattt cttaagctat ttctagagta    1620
tgatttacaa caggaaatgg atgatttgat tctgatcttt ataccttcat gcatttaaaa    1680
aagtacttaa gaaagtagtt tggtttgtca ttataaaaag caatacttat ttttatattg    1740
tgtagattca atcttgtttc cttgcctaga gtgggccgtg ctttggagtt cttatgagca    1800
tggcattcct gagaacttct ctaactgcag cctcgggcat agaggctggg cagcaagtgg    1860
cagcagcaga ggactcctag aagccttcta cttgactcta cttggcctaa agtcaaactc    1920
cctccaccaa agacagagtt tatttccaca taggatggag ttaaaaaata tattctgaga    1980
gaggaagggc ttgtggccca agagaacacc ccagaaatac cacccct tca tgggaagtga    2040 ctctatcttc aaacatataa cccagcctgg acatcccga aagacacata actttccatt    2100
tcatgccctt gaaagtgaat cttttggcct aataatgaga acaaactcat tttgaaagtg    2160
gaaaaattga gattcagagc agaagtttga ctaaggtcac aaaacagtag gatgcctcac    2220
tcagctccct gtgcctaggt cagaaaagca tcacaggaat agttgagcta ccagaatcct    2280
ctggccaggc aggagctgtg tgtccctggg aaatggggcc ctaaagggtt gctgcttaa     2340 gatgcctgtg gtgagtcagg aaggggttag aggaagttga ccaactagag tggtgaaacc    2400
tgtccatcac cttcaacctg gagggaggcc aggctgcaga atgatataaa gagtgccctg    2460
actcctgctc agctcagcac tccaccaaag cctctgcctc agccttactg tgagtctggt    2520
aagtgtcgga tggtagaacc agggttggga ctcgggacct ccaacagcat acgatgtggt    2580
gggggtgggc agcctgggtg ggggtgggca ttactctggg gctggattca gctggacttt    2640
cattctaggg ggactcgagt cagagtactg agagaaaagt gccttggcac agaagtgcag    2700
aacagagagt aatcatccta tgtcccatct tttcttgtga ccatattttt ggatttgtgt    2760
gtgagagaga attatggaag ggaggagggg aatagcattc aacttctttc ctaaacctct    2820
tgggttttga cagaccatca ttttgccttc tttatggagg gagaggttca gggaagagct    2880
tctacctttt ggctatgctg cacagaggga tggcagaatg gggaaacctt tctatttgga    2940
gaaacctagg cagagctggg acaggaaaac tcaacttaga agtataagac ttggaagaac    3000
aacctccaac tctcagcaac cttccagctc ccgcagcccc accccagaca caaggactgc    3060
agctaaacct cagaaggtca ggagagaaag cagccctggg gttgaatagg ccaacctgct    3120
ggctttacag gggggaaaac caaatcccag gagactaagt gacatgccca gaaacacaca    3180
gcattccaat gggagattca ggcctagagc atgtcctgtg gctccagtct ggaggtcaca    3240
ccatgacctc ttaggtcctc tctggcacgg cctattggtt ttctaggact tggtgttctc    3300
caagagacat ttcattccct aaggccttac tcctcactgt gacataatcc cagaacgcat    3360
ctctgctcct tggtcagtga agcgatgagg gtggacacaa ggactagaca agagcagaca    3420
gtgagctggc acctgaccca cccttgcaga acagccctgc agacagatct ccttgttggc    3480
tctcacctgg gaacaaggag gctcctagga ggacctttct ctgcccctcc acatttccac    3540
ccttctctct ctgctgcttt tgggaaatga tagtccagag gtggtagaac agtaccctgc    3600
ccaagggaag aggggatgct aaaaaaccag atacttctgc agattcccaa ggtttcatct    3660
atttcctttg ccttcagcct gtgcatcaga cctcttctgt ctttcaggtt gacagtagct    3720
```

-continued tctaag                                                              3726

<210> SEQ ID NO 13
<211> LENGTH: 68
<212> TYPE: PRT
<213> ORGANISM: Homo sapiens

<400> SEQUENCE: 13

Met Arg Thr Ser Tyr Leu Leu Leu Phe Thr Leu Cys Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65

<210> SEQ ID NO 14
<211> LENGTH: 64
<212> TYPE: PRT
<213> ORGANISM: Homo sapiens

<400> SEQUENCE: 14

Met Arg Val Leu Tyr Leu Leu Phe Ser Phe Leu Phe Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60

<210> SEQ ID NO 15
<211> LENGTH: 67
<212> TYPE: PRT
<213> ORGANISM: Homo sapiens

<400> SEQUENCE: 15

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65

<210> SEQ ID NO 16
<211> LENGTH: 64
<212> TYPE: PRT
<213> ORGANISM: Bos taurus

<400> SEQUENCE: 16

Met Arg Leu His His Leu Leu Leu Ala Leu Leu Phe Leu Val Leu Ser
1               5                   10                  15

```
Ala Gly Ser Gly Phe Thr Gln Gly Val Arg Asn Ser Gln Ser Cys Arg
         20                  25                  30

Arg Asn Lys Gly Ile Cys Val Pro Ile Arg Cys Pro Gly Ser Met Arg
     35                  40                  45

Gln Ile Gly Thr Cys Leu Gly Ala Gln Val Lys Cys Cys Arg Arg Lys
 50                  55                  60
```

<210> SEQ ID NO 17
<211> LENGTH: 24
<212> TYPE: PRT
<213> ORGANISM: Xenopus laevis

<400> SEQUENCE: 17

```
Gly Val Leu Ser Asn Val Ile Gly Tyr Leu Lys Lys Leu Gly Thr Gly
1               5                   10                  15

Ala Leu Asn Ala Val Leu Lys Gln
            20
```

<210> SEQ ID NO 18
<211> LENGTH: 81
<212> TYPE: PRT
<213> ORGANISM: Xenopus laevis

<400> SEQUENCE: 18

```
Met Tyr Lys Gly Ile Phe Leu Cys Val Leu Leu Ala Val Ile Cys Ala
1               5                   10                  15

Asn Ser Leu Ala Thr Pro Ser Ser Asp Ala Asp Glu Asp Asn Asp Glu
            20                  25                  30

Val Glu Arg Tyr Val Arg Gly Trp Ala Ser Lys Ile Gly Gln Thr Leu
        35                  40                  45

Gly Lys Ile Ala Lys Val Gly Leu Lys Glu Leu Ile Gln Pro Lys Arg
 50                  55                  60

Glu Ala Met Leu Arg Ser Ala Glu Ala Gln Gly Lys Arg Pro Trp Ile
65                  70                  75                  80

Leu
```

<210> SEQ ID NO 19
<211> LENGTH: 303
<212> TYPE: PRT
<213> ORGANISM: Xenopus laevis

<400> SEQUENCE: 19

```
Met Phe Lys Gly Leu Phe Ile Cys Ser Leu Ile Ala Val Ile Cys Ala
1               5                   10                  15

Asn Ala Leu Pro Gln Pro Glu Ala Ser Ala Asp Glu Asp Met Asp Glu
            20                  25                  30

Arg Glu Val Arg Gly Ile Gly Lys Phe Leu His Ser Ala Gly Lys Phe
        35                  40                  45

Gly Lys Ala Phe Val Gly Glu Ile Met Lys Ser Lys Arg Asp Ala Glu
 50                  55                  60

Ala Val Gly Pro Glu Ala Phe Ala Asp Glu Asp Leu Asp Glu Arg Glu
65                  70                  75                  80

Val Arg Gly Ile Gly Lys Phe Leu His Ser Ala Lys Lys Phe Gly Lys
            85                  90                  95

Ala Phe Val Gly Glu Ile Met Asn Ser Lys Arg Asp Ala Glu Ala Val
            100                 105                 110

Gly Pro Glu Ala Phe Ala Asp Glu Asp Leu Asp Glu Arg Glu Val Arg
        115                 120                 125
```

```
Gly Ile Gly Lys Phe Leu His Ser Ala Lys Lys Phe Gly Lys Ala Phe
            130                 135                 140

Val Gly Glu Ile Met Asn Ser Lys Arg Asp Ala Glu Ala Val Gly Pro
145                 150                 155                 160

Glu Ala Phe Ala Asp Glu Asp Leu Asp Glu Arg Glu Val Arg Gly Ile
                165                 170                 175

Gly Lys Phe Leu His Ser Ala Lys Lys Phe Gly Lys Ala Phe Val Gly
            180                 185                 190

Glu Ile Met Asn Ser Lys Arg Asp Ala Glu Ala Val Gly Pro Glu Ala
        195                 200                 205

Phe Ala Asp Glu Asp Phe Asp Glu Arg Glu Val Arg Gly Ile Gly Lys
    210                 215                 220

Phe Leu His Ser Ala Lys Lys Phe Gly Lys Ala Phe Val Gly Glu Ile
225                 230                 235                 240

Met Asn Ser Lys Arg Asp Ala Glu Ala Val Gly Pro Glu Ala Phe Ala
                245                 250                 255

Asp Glu Asp Leu Asp Glu Arg Glu Val Arg Gly Ile Gly Lys Phe Leu
                260                 265                 270

His Ser Ala Lys Lys Phe Gly Lys Ala Phe Val Gly Glu Ile Met Asn
            275                 280                 285

Ser Lys Arg Asp Ala Glu Ala Val Asp Asp Arg Arg Trp Val Glu
    290                 295                 300

<210> SEQ ID NO 20
<211> LENGTH: 17
<212> TYPE: PRT
<213> ORGANISM: Tachypleus gigas

<400> SEQUENCE: 20

Lys Trp Cys Phe Arg Val Cys Tyr Arg Gly Ile Cys Tyr Arg Arg Cys
1               5                   10                  15

Arg

<210> SEQ ID NO 21
<211> LENGTH: 17
<212> TYPE: PRT
<213> ORGANISM: Tachypleus gigas

<400> SEQUENCE: 21

Arg Trp Cys Phe Arg Val Cys Tyr Arg Gly Ile Cys Tyr Arg Lys Cys
1               5                   10                  15

Arg

<210> SEQ ID NO 22
<211> LENGTH: 129
<212> TYPE: PRT
<213> ORGANISM: Bufo bufo gagarizans

<400> SEQUENCE: 22

Met Ser Gly Arg Gly Lys Gln Gly Gly Lys Val Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ala Gln Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
```

```
              65                  70                  75                  80
Pro Arg His Leu Gln Leu Ala Val Arg Asn Asp Glu Glu Leu Asn Lys
                    85                  90                  95

Leu Leu Gly Gly Val Thr Ile Ala Gln Gly Gly Val Leu Pro Asn Ile
                    100                 105                 110

Gln Ala Val Leu Leu Pro Lys Thr Glu Ser Ser Lys Pro Ala Lys Ser
                    115                 120                 125

Lys

<210> SEQ ID NO 23
<211> LENGTH: 21
<212> TYPE: PRT
<213> ORGANISM: Bufo bufo gagarizans

<400> SEQUENCE: 23

Thr Arg Ser Ser Arg Ala Gly Leu Gln Phe Pro Val Gly Arg Val His
1               5                   10                  15

Arg Leu Leu Arg Lys
                20

<210> SEQ ID NO 24
<211> LENGTH: 63
<212> TYPE: PRT
<213> ORGANISM: Bombyx mori

<400> SEQUENCE: 24

Met Asn Phe Val Arg Ile Leu Ser Val Phe Ala Leu Val Leu Ala
1               5                   10                  15

Leu Gly Ala Val Ser Ala Ala Pro Glu Pro Arg Trp Lys Leu Phe Lys
                20                  25                  30

Lys Ile Glu Lys Val Gly Arg Asn Val Arg Asp Gly Leu Ile Lys Ala
                35                  40                  45

Gly Pro Ala Ile Ala Val Ile Gly Gln Ala Lys Ser Leu Gly Lys
            50                  55                  60

<210> SEQ ID NO 25
<211> LENGTH: 63
<212> TYPE: PRT
<213> ORGANISM: Bombyx mori

<400> SEQUENCE: 25

Met Asn Phe Ala Lys Ile Leu Ser Phe Val Phe Ala Leu Val Leu Ala
1               5                   10                  15

Leu Ser Met Thr Ser Ala Ala Pro Glu Pro Arg Trp Lys Ile Phe Lys
                20                  25                  30

Lys Ile Glu Lys Met Gly Arg Asn Ile Arg Asp Gly Ile Val Lys Ala
                35                  40                  45

Gly Pro Ala Ile Glu Val Leu Gly Ser Ala Lys Ala Ile Gly Lys
            50                  55                  60

<210> SEQ ID NO 26
<211> LENGTH: 63
<212> TYPE: PRT
<213> ORGANISM: Drosophila melanogaster

<400> SEQUENCE: 26

Met Asn Phe Tyr Lys Ile Phe Val Phe Val Ala Leu Ile Leu Ala Ile
1               5                   10                  15

Ser Ile Gly Gln Ser Glu Ala Gly Trp Leu Lys Lys Leu Gly Lys Arg
                20                  25                  30
```

```
Ile Glu Arg Ile Gly Gln His Thr Arg Asp Ala Thr Ile Gln Gly Leu
            35                  40                  45

Gly Ile Ala Gln Gln Ala Ala Asn Val Ala Ala Thr Ala Arg Gly
        50                  55                  60

<210> SEQ ID NO 27
<211> LENGTH: 31
<212> TYPE: PRT
<213> ORGANISM: Sus scrofa

<400> SEQUENCE: 27

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 28
<211> LENGTH: 13
<212> TYPE: PRT
<213> ORGANISM: Bos taurus

<400> SEQUENCE: 28

Ile Leu Pro Trp Lys Trp Pro Trp Trp Pro Trp Arg Arg
1               5                   10

<210> SEQ ID NO 29
<211> LENGTH: 34
<212> TYPE: PRT
<213> ORGANISM: Lactococcus lactis

<400> SEQUENCE: 29

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 30
<211> LENGTH: 20
<212> TYPE: PRT
<213> ORGANISM: Rana catesbeiana

<400> SEQUENCE: 30

Phe Leu Gly Gly Leu Ile Lys Ile Val Pro Ala Met Ile Cys Ala Val
1               5                   10                  15

Thr Lys Lys Cys
            20

<210> SEQ ID NO 31
<211> LENGTH: 25
<212> TYPE: PRT
<213> ORGANISM: Bos taurus

<400> SEQUENCE: 31

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 32
<211> LENGTH: 19
<212> TYPE: PRT
```

```
<213> ORGANISM: Sus scrofa
<220> FEATURE:
<221> NAME/KEY: misc_feature
<222> LOCATION: (19)..(19)
<223> OTHER INFORMATION: Xaa can be any naturally occurring amino acid

<400> SEQUENCE: 32

Arg Gly Gly Arg Leu Cys Tyr Cys Arg Arg Phe Cys Val Cys Val
1               5                   10                  15

Gly Arg Xaa

<210> SEQ ID NO 33
<211> LENGTH: 16
<212> TYPE: PRT
<213> ORGANISM: Sus scrofa

<400> SEQUENCE: 33

Gly Gly Arg Leu Cys Tyr Cys Arg Arg Phe Cys Ile Cys Val Gly
1               5                   10                  15

<210> SEQ ID NO 34
<211> LENGTH: 51
<212> TYPE: PRT
<213> ORGANISM: Homo sapiens

<400> SEQUENCE: 34

Met Lys Phe Phe Val Phe Ala Leu Ile Leu Ala Leu Met Leu Ser Met
1               5                   10                  15

Thr Gly Ala Asp Ser His Ala Lys Arg His His Gly Tyr Lys Arg Lys
            20                  25                  30

Phe His Glu Lys His His Ser His Arg Gly Tyr Arg Ser Asn Tyr Leu
        35                  40                  45

Tyr Asp Asn
    50

<210> SEQ ID NO 35
<211> LENGTH: 38
<212> TYPE: PRT
<213> ORGANISM: Macaca fascicularis

<400> SEQUENCE: 35

Asp Ser His Glu Glu Arg His His Gly Arg His Gly His Lys Tyr
1               5                   10                  15

Gly Arg Lys Phe His Glu Lys His His Ser His Arg Gly Tyr Arg Ser
            20                  25                  30

Asn Tyr Leu Tyr Asp Asn
            35

<210> SEQ ID NO 36
<211> LENGTH: 33
<212> TYPE: PRT
<213> ORGANISM: Phyllomedusa sauvagei

<400> SEQUENCE: 36

Ala Leu Trp Lys Thr Met Leu Lys Leu Gly Thr Met Ala Leu His
1               5                   10                  15

Ala Gly Lys Ala Ala Leu Gly Ala Ala Ala Asp Thr Ile Ser Gln Thr
            20                  25                  30

Gln

<210> SEQ ID NO 37
<211> LENGTH: 34
```

```
<212> TYPE: PRT
<213> ORGANISM: Phyllomedusa sauvagei

<400> SEQUENCE: 37

Ala Leu Trp Phe Thr Met Leu Lys Lys Leu Gly Thr Met Ala Leu His
1               5                   10                  15

Ala Gly Lys Ala Ala Leu Gly Ala Ala Ala Asn Thr Ile Ser Gln Gly
            20                  25                  30

Thr Gln

<210> SEQ ID NO 38
<211> LENGTH: 30
<212> TYPE: PRT
<213> ORGANISM: Phyllomedusa sauvagei

<400> SEQUENCE: 38

Ala Leu Trp Lys Asn Met Leu Lys Gly Ile Gly Lys Leu Ala Gly Lys
1               5                   10                  15

Ala Ala Leu Gly Ala Val Lys Lys Leu Val Gly Ala Glu Ser
            20                  25                  30

<210> SEQ ID NO 39
<211> LENGTH: 21
<212> TYPE: PRT
<213> ORGANISM: Misgurnus anguillicaudatus

<400> SEQUENCE: 39

Arg Gln Arg Val Glu Glu Leu Ser Lys Phe Ser Lys Lys Gly Ala Ala
1               5                   10                  15

Ala Arg Arg Arg Lys
            20

<210> SEQ ID NO 40
<211> LENGTH: 27
<212> TYPE: PRT
<213> ORGANISM: Apis mellifera

<400> SEQUENCE: 40

Gly Ile Gly Ala Val Leu Lys Val Leu Thr Thr Gly Leu Pro Ala Leu
1               5                   10                  15

Ile Ser Trp Ile Ser Arg Lys Lys Arg Gln Gln
            20                  25

<210> SEQ ID NO 41
<211> LENGTH: 33
<212> TYPE: PRT
<213> ORGANISM: Pardachirus pavoninus

<400> SEQUENCE: 41

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Glu Gln
            20                  25                  30

Glu

<210> SEQ ID NO 42
<211> LENGTH: 33
<212> TYPE: PRT
<213> ORGANISM: Pardachirus pavoninus

<400> SEQUENCE: 42

Gly Phe Phe Ala Leu Ile Pro Lys Ile Ile Ser Ser Pro Ile Phe Lys
```

-continued

```
                1               5                  10                 15
Thr Leu Leu Ser Ala Val Gly Ser Ala Leu Ser Ser Ser Gly Gly Gln
                20                 25                 30

Glu

<210> SEQ ID NO 43
<211> LENGTH: 176
<212> TYPE: PRT
<213> ORGANISM: Bos taurus

<400> SEQUENCE: 43

Met Glu Thr Gln Arg Ala Ser Leu Ser Leu Gly Arg Cys Ser Leu Trp
1               5                  10                 15

Leu Leu Leu Leu Gly Leu Val Leu Pro Ser Ala Ser Ala Gln Ala Leu
                20                 25                 30

Ser Tyr Arg Glu Ala Val Leu Arg Ala Val Asp Gln Phe Asn Glu Arg
            35                 40                 45

Ser Ser Glu Ala Asn Leu Tyr Arg Leu Leu Glu Leu Asp Pro Thr Pro
        50                 55                 60

Asn Asp Asp Leu Asp Pro Gly Thr Arg Lys Pro Val Ser Phe Arg Val
65                 70                 75                 80

Lys Glu Thr Asp Cys Pro Arg Thr Ser Gln Gln Pro Leu Glu Gln Cys
                85                 90                 95

Asp Phe Lys Glu Asn Gly Leu Val Lys Gln Cys Val Gly Thr Val Thr
            100                105                110

Leu Asp Pro Ser Asn Asp Gln Phe Asp Ile Asn Cys Asn Glu Leu Gln
        115                120                125

Ser Val Arg Phe Arg Pro Pro Ile Arg Arg Pro Pro Ile Arg Pro Pro
130                135                140

Phe Tyr Pro Pro Phe Arg Pro Ile Arg Pro Ile Phe Pro Pro
145                150                155                160

Ile Arg Pro Pro Phe Arg Pro Leu Gly Pro Phe Pro Gly Arg Arg
                165                170                175

<210> SEQ ID NO 44
<211> LENGTH: 155
<212> TYPE: PRT
<213> ORGANISM: Bos taurus

<400> SEQUENCE: 44

Met Glu Thr Pro Arg Ala Ser Leu Ser Leu Gly Arg Trp Ser Leu Trp
1               5                  10                 15

Leu Leu Leu Leu Gly Leu Ala Leu Pro Ser Ala Ser Ala Gln Ala Leu
                20                 25                 30

Ser Tyr Arg Glu Ala Val Leu Arg Ala Val Asp Gln Leu Asn Glu Gln
            35                 40                 45

Ser Ser Glu Pro Asn Ile Tyr Arg Leu Leu Glu Leu Asp Gln Pro Pro
        50                 55                 60

Gln Asp Asp Glu Asp Pro Asp Ser Pro Lys Arg Val Ser Phe Arg Val
65                 70                 75                 80

Lys Glu Thr Val Cys Ser Arg Thr Thr Gln Gln Pro Pro Glu Gln Cys
                85                 90                 95

Asp Phe Lys Glu Asn Gly Leu Leu Lys Arg Cys Glu Gly Thr Val Thr
            100                105                110

Leu Asp Gln Val Arg Gly Asn Phe Asp Ile Thr Cys Asn Asn His Gln
        115                120                125
```

```
Ser Ile Arg Ile Thr Lys Gln Pro Trp Ala Pro Gln Ala Ala Arg
        130                 135                 140

Leu Cys Arg Ile Val Val Ile Arg Val Cys Arg
145                 150                 155

<210> SEQ ID NO 45
<211> LENGTH: 29
<212> TYPE: PRT
<213> ORGANISM: Ceratitis capitata

<400> SEQUENCE: 45

Ser Ile Gly Ser Ala Leu Lys Lys Ala Leu Pro Val Ala Lys Lys Ile
1               5                   10                  15

Gly Lys Ile Ala Leu Pro Ile Ala Lys Ala Ala Leu Pro
            20                  25

<210> SEQ ID NO 46
<211> LENGTH: 29
<212> TYPE: PRT
<213> ORGANISM: Ceratitis capitata

<400> SEQUENCE: 46

Ser Ile Gly Ser Ala Phe Lys Lys Ala Leu Pro Val Ala Lys Lys Ile
1               5                   10                  15

Gly Lys Ala Ala Leu Pro Ile Ala Lys Ala Ala Leu Pro
            20                  25

<210> SEQ ID NO 47
<211> LENGTH: 170
<212> TYPE: PRT
<213> ORGANISM: Homo sapiens

<400> SEQUENCE: 47

Met Lys Thr Gln Arg Asn Gly His Ser Leu Gly Arg Trp Ser Leu Val
1               5                   10                  15

Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
            35                  40                  45

Arg Ser Ser Asp Ala Asn Leu Tyr Arg Leu Leu Asp Leu Asp Pro Arg
50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
        165                 170

<210> SEQ ID NO 48
<211> LENGTH: 170
<212> TYPE: PRT
<213> ORGANISM: Equus caballus
```

-continued

<400> SEQUENCE: 48

Met Glu Thr Gln Arg Asn Thr Arg Cys Leu Gly Arg Trp Ser Pro Leu
1               5                   10                  15

Leu Leu Leu Leu Gly Leu Val Ile Pro Pro Ala Thr Thr Gln Ala Leu
            20                  25                  30

Ser Tyr Lys Glu Ala Val Leu Arg Ala Val Asp Gly Leu Asn Gln Arg
        35                  40                  45

Ser Ser Asp Glu Asn Leu Tyr Arg Leu Leu Glu Leu Asp Pro Leu Pro
    50                  55                  60

Lys Gly Asp Lys Asp Ser Asp Thr Pro Lys Pro Val Ser Phe Met Val
65                  70                  75                  80

Lys Glu Thr Val Cys Pro Arg Ile Met Lys Gln Thr Pro Glu Gln Cys
                85                  90                  95

Asp Phe Lys Glu Asn Gly Leu Val Lys Gln Cys Val Gly Thr Val Ile
            100                 105                 110

Leu Asp Pro Val Lys Asp Tyr Phe Asp Ala Ser Cys Asp Glu Pro Gln
        115                 120                 125

Arg Val Lys Arg Phe His Ser Val Gly Ser Leu Ile Gln Arg His Gln
    130                 135                 140

Gln Met Ile Arg Asp Lys Ser Glu Ala Thr Arg His Gly Ile Arg Ile
145                 150                 155                 160

Ile Thr Arg Pro Lys Leu Leu Leu Ala Ser
                165                 170

<210> SEQ ID NO 49
<211> LENGTH: 159
<212> TYPE: PRT
<213> ORGANISM: Bos taurus

<400> SEQUENCE: 49

Met Glu Thr Gln Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
            20                  25                  30

Ser Tyr Arg Glu Ala Val Leu Arg Ala Val Asp Gln Leu Asn Glu Lys
        35                  40                  45

Ser Ser Glu Ala Asn Leu Tyr Arg Leu Leu Glu Leu Asp Pro Pro Pro
    50                  55                  60

Lys Glu Asp Asp Glu Asn Pro Asn Ile Pro Lys Pro Val Ser Phe Arg
65                  70                  75                  80

Val Lys Glu Thr Val Cys Pro Arg Thr Ser Gln Gln Ser Pro Glu Gln
                85                  90                  95

Cys Asp Phe Lys Glu Asn Gly Leu Leu Lys Glu Cys Val Gly Thr Val
            100                 105                 110

Thr Leu Asp Gln Val Gly Ser Asn Phe Asp Ile Thr Cys Ala Val Pro
        115                 120                 125

Gln Ser Val Gly Gly Leu Arg Ser Leu Gly Arg Lys Ile Leu Arg Ala
    130                 135                 140

Trp Lys Lys Tyr Gly Pro Ile Ile Val Pro Ile Ile Arg Ile Gly
145                 150                 155

<210> SEQ ID NO 50
<211> LENGTH: 156
<212> TYPE: PRT
<213> ORGANISM: Equus caballus

```
<400> SEQUENCE: 50

Met Glu Thr Gln Arg Asn Thr Arg Cys Leu Gly Arg Trp Ser Pro Leu
1               5                   10                  15

Leu Leu Leu Leu Gly Leu Val Ile Pro Pro Ala Thr Thr Gln Ala Leu
            20                  25                  30

Ser Tyr Lys Glu Ala Val Leu Arg Ala Val Asp Gly Leu Asn Gln Arg
        35                  40                  45

Ser Ser Asp Glu Asn Leu Tyr Arg Leu Leu Glu Leu Asp Pro Leu Pro
    50                  55                  60

Lys Gly Asp Lys Asp Ser Asp Thr Pro Lys Pro Val Ser Phe Met Val
65                  70                  75                  80

Lys Glu Thr Val Cys Pro Arg Ile Met Lys Gln Thr Pro Glu Gln Cys
                85                  90                  95

Asp Phe Lys Glu Asn Gly Leu Val Lys Gln Cys Val Gly Thr Val Ile
            100                 105                 110

Leu Gly Pro Val Lys Asp His Phe Asp Val Ser Cys Gly Glu Pro Gln
        115                 120                 125

Arg Val Lys Arg Phe Gly Arg Leu Ala Lys Ser Phe Leu Arg Met Arg
    130                 135                 140

Ile Leu Leu Pro Arg Arg Lys Ile Leu Leu Ala Ser
145                 150                 155

<210> SEQ ID NO 51
<211> LENGTH: 160
<212> TYPE: PRT
<213> ORGANISM: Ovis aries

<400> SEQUENCE: 51

Met Glu Thr Gln Arg Ala Ser Leu Ser Leu Gly Arg Cys Ser Leu Trp
1               5                   10                  15

Leu Leu Leu Leu Gly Leu Ala Leu Pro Ser Ala Ser Ala Gln Val Leu
            20                  25                  30

Ser Tyr Arg Glu Ala Val Leu Arg Ala Ala Asp Gln Leu Asn Glu Lys
        35                  40                  45

Ser Ser Glu Ala Asn Leu Tyr Arg Leu Leu Glu Leu Asp Pro Pro Pro
    50                  55                  60

Lys Gln Asp Asp Glu Asn Ser Asn Ile Pro Lys Pro Val Ser Phe Arg
65                  70                  75                  80

Val Lys Glu Thr Val Cys Pro Arg Thr Ser Gln Gln Pro Ala Glu Gln
                85                  90                  95

Cys Asp Phe Lys Glu Asn Gly Leu Leu Lys Glu Cys Val Gly Thr Val
            100                 105                 110

Thr Leu Asp Gln Val Arg Asn Asn Phe Asp Ile Thr Cys Ala Glu Pro
        115                 120                 125

Gln Ser Val Arg Gly Leu Arg Arg Leu Gly Arg Lys Ile Ala His Gly
    130                 135                 140

Val Lys Lys Tyr Gly Pro Thr Val Leu Arg Ile Ile Arg Ile Ala Gly
145                 150                 155                 160

<210> SEQ ID NO 52
<211> LENGTH: 12
<212> TYPE: PRT
<213> ORGANISM: Bos taurus

<400> SEQUENCE: 52

Arg Leu Cys Arg Ile Val Val Ile Arg Val Cys Arg
1               5                   10
```

<210> SEQ ID NO 53
<211> LENGTH: 30
<212> TYPE: PRT
<213> ORGANISM: Homo sapiens

<400> SEQUENCE: 53

Ala Cys Tyr Cys Arg Ile Pro Ala Cys Ile Ala Gly Glu Arg Arg Tyr
1               5                   10                  15
Gly Thr Cys Ile Tyr Gln Gly Arg Leu Trp Ala Phe Cys Cys
            20                  25                  30

<210> SEQ ID NO 54
<211> LENGTH: 29
<212> TYPE: PRT
<213> ORGANISM: Homo sapiens

<400> SEQUENCE: 54

Cys Tyr Cys Arg Ile Pro Ala Cys Ile Ala Gly Glu Arg Arg Tyr Gly
1               5                   10                  15
Thr Cys Ile Tyr Gln Gly Arg Leu Trp Ala Phe Cys Cys
            20                  25

<210> SEQ ID NO 55
<211> LENGTH: 30
<212> TYPE: PRT
<213> ORGANISM: Homo sapiens

<400> SEQUENCE: 55

Asp Cys Tyr Cys Arg Ile Pro Ala Cys Ile Ala Gly Glu Arg Arg Tyr
1               5                   10                  15
Gly Thr Cys Ile Tyr Gln Gly Arg Leu Trp Ala Phe Cys Cys
            20                  25                  30

<210> SEQ ID NO 56
<211> LENGTH: 33
<212> TYPE: PRT
<213> ORGANISM: Homo sapiens

<400> SEQUENCE: 56

Val Cys Ser Cys Arg Leu Val Phe Cys Arg Arg Thr Glu Leu Arg Val
1               5                   10                  15
Gly Asn Cys Leu Ile Gly Gly Val Ser Phe Thr Tyr Cys Cys Thr Arg
            20                  25                  30
Val

<210> SEQ ID NO 57
<211> LENGTH: 33
<212> TYPE: PRT
<213> ORGANISM: Oryctolagus cuniculus

<400> SEQUENCE: 57

Val Val Cys Ala Cys Arg Arg Ala Leu Cys Leu Pro Arg Glu Arg Arg
1               5                   10                  15
Ala Gly Phe Cys Arg Ile Arg Gly Arg Ile His Pro Leu Cys Cys Arg
            20                  25                  30
Arg

<210> SEQ ID NO 58
<211> LENGTH: 33
<212> TYPE: PRT
<213> ORGANISM: Oryctolagus cuniculus

```
<400> SEQUENCE: 58

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 59
<211> LENGTH: 34
<212> TYPE: PRT
<213> ORGANISM: Oryctolagus cuniculus

<400> SEQUENCE: 59

Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30

Arg Arg

<210> SEQ ID NO 60
<211> LENGTH: 34
<212> TYPE: PRT
<213> ORGANISM: Oryctolagus cuniculus

<400> SEQUENCE: 60

Gly Arg Cys Val Cys Arg Lys Gln Leu Leu Cys Ser Tyr Arg Glu Arg
1               5                   10                  15

Arg Ile Gly Asp Cys Lys Ile Arg Gly Val Arg Phe Pro Phe Cys Cys
            20                  25                  30

Pro Arg

<210> SEQ ID NO 61
<211> LENGTH: 34
<212> TYPE: PRT
<213> ORGANISM: Oryctolagus cuniculus

<400> SEQUENCE: 61

Val Ser Cys Thr Cys Arg Arg Phe Ser Cys Gly Phe Gly Glu Arg Ala
1               5                   10                  15

Ser Gly Ser Cys Thr Val Asn Gly Gly Val Arg His Thr Leu Cys Cys
            20                  25                  30

Arg Arg

<210> SEQ ID NO 62
<211> LENGTH: 33
<212> TYPE: PRT
<213> ORGANISM: Oryctolagus cuniculus

<400> SEQUENCE: 62

Val Phe Cys Thr Cys Arg Gly Phe Leu Cys Gly Ser Gly Glu Arg Ala
1               5                   10                  15

Ser Gly Ser Cys Thr Ile Asn Gly Val Arg His Thr Leu Cys Cys Arg
            20                  25                  30

Arg

<210> SEQ ID NO 63
<211> LENGTH: 32
<212> TYPE: PRT
<213> ORGANISM: Rattus norvegicus
```

<400> SEQUENCE: 63

Val Thr Cys Tyr Cys Arg Arg Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 64
<211> LENGTH: 30
<212> TYPE: PRT
<213> ORGANISM: Rattus norvegicus

<400> SEQUENCE: 64

Cys Ser Cys Arg Tyr Ser Ser Cys Arg Phe Gly Glu Arg Leu Leu Ser
1               5                   10                  15

Gly Ala Cys Arg Leu Asn Gly Arg Ile Tyr Arg Leu Cys Cys
            20                  25                  30

<210> SEQ ID NO 65
<211> LENGTH: 31
<212> TYPE: PRT
<213> ORGANISM: Rattus norvegicus

<400> SEQUENCE: 65

Ala Cys Thr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20                  25                  30

<210> SEQ ID NO 66
<211> LENGTH: 39
<212> TYPE: PRT
<213> ORGANISM: Guinea pig

<400> SEQUENCE: 66

Gly Ile Asn Glu Ala Pro Ile Gly Arg Arg Cys Ile Cys Thr Thr Arg
1               5                   10                  15

Thr Cys Arg Phe Pro Tyr Arg Arg Leu Gly Thr Cys Ile Phe Gln Asn
            20                  25                  30

Arg Val Tyr Thr Phe Cys Cys
        35

<210> SEQ ID NO 67
<211> LENGTH: 18
<212> TYPE: PRT
<213> ORGANISM: Macaca mulatta

<400> SEQUENCE: 67

Arg Cys Ile Cys Thr Arg Gly Phe Cys Arg Cys Leu Cys Arg Arg Gly
1               5                   10                  15

Val Cys

<210> SEQ ID NO 68
<211> LENGTH: 78
<212> TYPE: PRT
<213> ORGANISM: Helianthus annuus

<400> SEQUENCE: 68

Met Lys Ser Ser Met Lys Met Phe Ala Ala Leu Leu Leu Val Val Met
1               5                   10                  15

Cys Leu Leu Ala Asn Glu Met Gly Gly Pro Leu Val Val Glu Ala Arg
            20                  25                  30

```
Thr Cys Glu Ser Gln Ser His Lys Phe Lys Gly Thr Cys Leu Ser Asp
            35                  40                  45

Thr Asn Cys Ala Asn Val Cys His Ser Glu Arg Phe Ser Gly Gly Lys
 50                  55                  60

Cys Arg Gly Phe Arg Arg Arg Cys Phe Cys Thr Thr His Cys
 65                  70                  75
```

<210> SEQ ID NO 69
<211> LENGTH: 78
<212> TYPE: PRT
<213> ORGANISM: Helianthus annuus

<400> SEQUENCE: 69

```
Met Lys Ser Ser Met Lys Met Phe Ala Ala Leu Leu Val Val Met
 1               5                  10                  15

Cys Leu Leu Ala Asn Glu Met Gly Gly Pro Leu Val Val Glu Ala Arg
            20                  25                  30

Thr Cys Glu Ser Gln Ser His Lys Phe Lys Gly Thr Cys Leu Ser Asp
            35                  40                  45

Thr Asn Cys Ala Asn Val Cys His Ser Glu Arg Phe Ser Gly Gly Lys
 50                  55                  60

Cys Arg Gly Phe Arg Arg Arg Cys Phe Cys Thr Thr His Cys
 65                  70                  75
```

<210> SEQ ID NO 70
<211> LENGTH: 30
<212> TYPE: PRT
<213> ORGANISM: Macaca mulatta

<400> SEQUENCE: 70

```
Ala Cys Tyr Cys Arg Ile Pro Ala Cys Leu Ala Gly Glu Arg Arg Tyr
 1               5                  10                  15

Gly Thr Cys Phe Tyr Met Gly Arg Val Trp Ala Phe Cys Cys
            20                  25                  30
```

<210> SEQ ID NO 71
<211> LENGTH: 37
<212> TYPE: PRT
<213> ORGANISM: Androctonus australis hector

<400> SEQUENCE: 71

```
Gly Phe Gly Cys Pro Phe Asn Gln Gly Ala Cys His Arg His Cys Arg
 1               5                  10                  15

Ser Ile Arg Arg Arg Gly Gly Tyr Cys Ala Gly Leu Phe Lys Gln Thr
            20                  25                  30

Cys Thr Cys Tyr Arg
            35
```

<210> SEQ ID NO 72
<211> LENGTH: 38
<212> TYPE: PRT
<213> ORGANISM: Mytilus galloprovincialis
<220> FEATURE:
<221> NAME/KEY: misc_feature
<222> LOCATION: (28)..(28)
<223> OTHER INFORMATION: Xaa can be any naturally occurring amino acid

<400> SEQUENCE: 72

```
Gly Phe Gly Cys Pro Asn Asn Tyr Gln Cys His Arg His Cys Lys Ser
 1               5                  10                  15

Ile Pro Gly Arg Cys Gly Gly Tyr Cys Gly Gly Xaa His Arg Leu Arg
```

```
                    20                  25                  30

Cys Thr Cys Tyr Arg Cys
            35

<210> SEQ ID NO 73
<211> LENGTH: 54
<212> TYPE: PRT
<213> ORGANISM: Heuchera sanguinea

<400> SEQUENCE: 73

Asp Gly Val Lys Leu Cys Asp Val Pro Ser Gly Thr Trp Ser Gly His
1               5                   10                  15

Cys Gly Ser Ser Ser Lys Cys Ser Gln Gln Cys Lys Asp Arg Glu His
                20                  25                  30

Phe Ala Tyr Gly Gly Ala Cys His Tyr Gln Phe Pro Ser Val Lys Cys
            35                  40                  45

Phe Cys Lys Arg Gln Cys
        50

<210> SEQ ID NO 74
<211> LENGTH: 49
<212> TYPE: PRT
<213> ORGANISM: Clitoria ternatea

<400> SEQUENCE: 74

Asn Leu Cys Glu Arg Ala Ser Leu Thr Trp Thr Gly Asn Cys Gly Asn
1               5                   10                  15

Thr Gly His Cys Asp Thr Gln Cys Arg Asn Trp Glu Ser Ala Lys His
                20                  25                  30

Gly Ala Cys His Lys Arg Gly Asn Trp Lys Cys Phe Cys Tyr Phe Asn
            35                  40                  45

Cys

<210> SEQ ID NO 75
<211> LENGTH: 91
<212> TYPE: PRT
<213> ORGANISM: Mus musculus

<400> SEQUENCE: 75

Met Lys Lys Leu Val Leu Leu Phe Ala Leu Val Leu Leu Ala Phe Gln
1               5                   10                  15

Val Gln Ala Asp Ser Ile Gln Asn Thr Asp Glu Glu Thr Lys Thr Glu
                20                  25                  30

Glu Gln Pro Gly Glu Lys Asp Gln Ala Val Ser Val Ser Phe Gly Asp
            35                  40                  45

Pro Gln Gly Ser Ala Leu Gln Asp Ala Ala Leu Gly Trp Gly Arg Arg
        50                  55                  60

Cys Pro Gln Cys Pro Arg Cys Pro Ser Cys Pro Ser Cys Pro Arg Cys
65                  70                  75                  80

Pro Arg Cys Pro Arg Cys Lys Cys Asn Pro Lys
                85                  90

<210> SEQ ID NO 76
<211> LENGTH: 40
<212> TYPE: PRT
<213> ORGANISM: Bos taurus

<400> SEQUENCE: 76

Gln Gly Val Arg Asn Phe Val Thr Cys Arg Ile Asn Arg Gly Phe Cys
1               5                   10                  15
```

```
Val Pro Ile Arg Cys Pro Gly His Arg Arg Gln Ile Gly Thr Cys Leu
            20                  25                  30

Gly Pro Gln Ile Lys Cys Cys Arg
        35                  40

<210> SEQ ID NO 77
<211> LENGTH: 40
<212> TYPE: PRT
<213> ORGANISM: Bos taurus

<400> SEQUENCE: 77

Gln Gly Val Arg Asn Phe Val Thr Cys Arg Ile Asn Arg Gly Phe Cys
1               5                   10                  15

Val Pro Ile Arg Cys Pro Gly His Arg Arg Gln Ile Gly Thr Cys Leu
            20                  25                  30

Gly Pro Arg Ile Lys Cys Cys Arg
        35                  40

<210> SEQ ID NO 78
<211> LENGTH: 42
<212> TYPE: PRT
<213> ORGANISM: Bos taurus

<400> SEQUENCE: 78

Gln Gly Val Arg Asn His Val Thr Cys Arg Ile Tyr Gly Gly Phe Cys
1               5                   10                  15

Val Pro Ile Arg Cys Pro Gly Arg Thr Arg Gln Ile Gly Thr Cys Phe
            20                  25                  30

Gly Arg Pro Val Lys Cys Cys Arg Arg Trp
        35                  40

<210> SEQ ID NO 79
<211> LENGTH: 40
<212> TYPE: PRT
<213> ORGANISM: Bos taurus

<400> SEQUENCE: 79

Gln Val Val Arg Asn Pro Gln Ser Cys Arg Trp Asn Met Gly Val Cys
1               5                   10                  15

Ile Pro Ile Ser Cys Pro Gly Asn Met Arg Gln Ile Gly Thr Cys Phe
            20                  25                  30

Gly Pro Arg Val Pro Cys Cys Arg
        35                  40

<210> SEQ ID NO 80
<211> LENGTH: 41
<212> TYPE: PRT
<213> ORGANISM: Bos taurus

<400> SEQUENCE: 80

Gln Arg Val Arg Asn Pro Gln Ser Cys Arg Trp Asn Met Gly Val Cys
1               5                   10                  15

Ile Pro Phe Leu Cys Arg Val Gly Met Arg Gln Ile Gly Thr Cys Phe
            20                  25                  30

Gly Pro Arg Val Pro Cys Cys Arg Arg
        35                  40

<210> SEQ ID NO 81
<211> LENGTH: 42
<212> TYPE: PRT
<213> ORGANISM: Bos taurus
```

<400> SEQUENCE: 81

Gln Gly Val Arg Asn His Val Thr Cys Arg Ile Asn Arg Gly Phe Cys
1               5                   10                  15

Val Pro Ile Arg Cys Pro Gly Arg Thr Arg Gln Ile Gly Thr Cys Phe
            20                  25                  30

Gly Pro Arg Ile Lys Cys Cys Arg Ser Trp
        35                  40

<210> SEQ ID NO 82
<211> LENGTH: 40
<212> TYPE: PRT
<213> ORGANISM: Bos taurus

<400> SEQUENCE: 82

Gln Gly Val Arg Ser Tyr Leu Ser Cys Trp Gly Asn Arg Gly Ile Cys
1               5                   10                  15

Leu Leu Asn Arg Cys Pro Gly Arg Met Arg Gln Ile Gly Thr Cys Leu
            20                  25                  30

Ala Pro Arg Val Lys Cys Cys Arg
        35                  40

<210> SEQ ID NO 83
<211> LENGTH: 42
<212> TYPE: PRT
<213> ORGANISM: Bos taurus

<400> SEQUENCE: 83

Ser Gly Ile Ser Gly Pro Leu Ser Cys Gly Arg Asn Gly Gly Val Cys
1               5                   10                  15

Ile Pro Ile Arg Cys Pro Val Pro Met Arg Gln Ile Gly Thr Cys Phe
            20                  25                  30

Gly Arg Pro Val Lys Cys Cys Arg Ser Trp
        35                  40

<210> SEQ ID NO 84
<211> LENGTH: 38
<212> TYPE: PRT
<213> ORGANISM: Bos taurus

<400> SEQUENCE: 84

Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
            20                  25                  30

Lys Cys Cys Arg Ser Trp
        35

<210> SEQ ID NO 85
<211> LENGTH: 74
<212> TYPE: PRT
<213> ORGANISM: Zophobas atratus

<400> SEQUENCE: 85

Ser Leu Gln Gly Gly Ala Pro Asn Phe Pro Gln Pro Ser Gln Gln Asn
1               5                   10                  15

Gly Gly Trp Gln Val Ser Pro Asp Leu Gly Arg Asp Asp Lys Gly Asn
            20                  25                  30

Thr Arg Gly Gln Ile Glu Ile Gln Asn Lys Gly Lys Asp His Asp Phe
        35                  40                  45

Asn Ala Gly Trp Gly Lys Val Ile Arg Gly Pro Asn Lys Ala Lys Pro
            50                   55                  60

Thr Trp His Val Gly Gly Thr Tyr Arg Arg
 65                  70

<210> SEQ ID NO 86
<211> LENGTH: 40
<212> TYPE: PRT
<213> ORGANISM: Aedes aegypti

<400> SEQUENCE: 86

Ala Thr Cys Asp Leu Leu Ser Gly Phe Gly Val Gly Asp Ser Ala Cys
 1               5                  10                  15

Ala Ala His Cys Ile Ala Arg Gly Asn Arg Gly Gly Tyr Cys Asn Ser
            20                  25                  30

Lys Lys Val Cys Val Cys Arg Asn
         35                  40

<210> SEQ ID NO 87
<211> LENGTH: 35
<212> TYPE: PRT
<213> ORGANISM: Mytilus edulis
<220> FEATURE:
<221> NAME/KEY: misc_feature
<222> LOCATION: (28)..(28)
<223> OTHER INFORMATION: Xaa can be any naturally occurring amino acid

<400> SEQUENCE: 87

Gly Phe Gly Cys Pro Asn Asp Tyr Pro Cys His Arg His Cys Lys Ser
 1               5                  10                  15

Ile Pro Gly Arg Tyr Gly Gly Tyr Cys Gly Gly Xaa His Arg Leu Arg
            20                  25                  30

Cys Thr Cys
         35

<210> SEQ ID NO 88
<211> LENGTH: 40
<212> TYPE: PRT
<213> ORGANISM: Sarcophaga peregrina

<400> SEQUENCE: 88

Ala Thr Cys Asp Leu Leu Ser Gly Ile Gly Val Gln His Ser Ala Cys
 1               5                  10                  15

Ala Leu His Cys Val Phe Arg Gly Asn Arg Gly Gly Tyr Cys Thr Gly
            20                  25                  30

Lys Gly Ile Cys Val Cys Arg Asn
         35                  40

<210> SEQ ID NO 89
<211> LENGTH: 95
<212> TYPE: PRT
<213> ORGANISM: Oryctolagus cuniculus

<400> SEQUENCE: 89

Met Arg Thr Leu Ala Leu Leu Ala Ala Ile Leu Leu Val Ala Leu Gln
 1               5                  10                  15

Ala Gln Ala Glu His Val Ser Val Ser Ile Asp Glu Val Val Asp Gln
            20                  25                  30

Gln Pro Pro Gln Ala Glu Asp Gln Asp Val Ala Ile Tyr Val Lys Glu
         35                  40                  45

His Glu Ser Ser Ala Leu Glu Ala Leu Gly Val Lys Ala Gly Val Val
     50                  55                  60

```
Cys Ala Cys Arg Arg Ala Leu Cys Leu Pro Arg Glu Arg Ala Gly
 65                  70                  75                  80

Phe Cys Arg Ile Arg Gly Arg Ile His Pro Leu Cys Cys Arg Arg
                 85                  90                  95
```

<210> SEQ ID NO 90
<211> LENGTH: 92
<212> TYPE: PRT
<213> ORGANISM: Mus musculus

<400> SEQUENCE: 90

```
Met Lys Pro Leu Val Leu Leu Ser Ala Leu Val Leu Leu Ser Phe Gln
 1               5                  10                  15

Val Gln Ala Asp Pro Ile Gln Asn Thr Asp Glu Glu Thr Lys Thr Glu
             20                  25                  30

Glu Gln Ser Gly Glu Glu Asp Gln Ala Val Ser Val Ser Phe Gly Asp
         35                  40                  45

Arg Glu Gly Ala Ser Leu Gln Glu Ser Leu Arg Asp Leu Val Cys
 50                  55                  60

Tyr Cys Arg Thr Arg Gly Cys Lys Arg Arg Glu Arg Met Asn Gly Thr
 65                  70                  75                  80

Cys Arg Lys Gly His Leu Met Tyr Thr Leu Cys Cys
                 85                  90
```

<210> SEQ ID NO 91
<211> LENGTH: 93
<212> TYPE: PRT
<213> ORGANISM: Mus musculus

<400> SEQUENCE: 91

```
Met Lys Thr Phe Val Leu Leu Ser Ala Leu Val Leu Leu Ala Phe Gln
 1               5                  10                  15

Val Gln Ala Asp Pro Ile His Lys Thr Asp Glu Glu Thr Asn Thr Glu
             20                  25                  30

Glu Gln Pro Gly Glu Glu Asp Gln Ala Val Ser Ile Ser Phe Gly Gly
         35                  40                  45

Gln Glu Gly Ser Ala Leu His Glu Glu Leu Ser Lys Lys Leu Ile Cys
 50                  55                  60

Tyr Cys Arg Ile Arg Gly Cys Lys Arg Arg Glu Arg Val Phe Gly Thr
 65                  70                  75                  80

Cys Arg Asn Leu Phe Leu Thr Phe Val Phe Cys Cys Ser
                 85                  90
```

<210> SEQ ID NO 92
<211> LENGTH: 35
<212> TYPE: PRT
<213> ORGANISM: Mus musculus

<400> SEQUENCE: 92

```
Leu Arg Asp Leu Val Cys Tyr Cys Arg Ala Arg Gly Cys Lys Gly Arg
 1               5                  10                  15

Glu Arg Met Asn Gly Thr Cys Arg Lys Gly His Leu Leu Tyr Met Leu
             20                  25                  30

Cys Cys Arg
         35
```

<210> SEQ ID NO 93
<211> LENGTH: 43
<212> TYPE: PRT

<213> ORGANISM: Pyrrhocoris apterus

<400> SEQUENCE: 93

Ala Thr Cys Asp Ile Leu Ser Phe Gln Ser Gln Trp Val Thr Pro Asn
1               5                   10                  15

His Ala Gly Cys Ala Leu His Cys Val Ile Lys Gly Tyr Lys Gly Gly
            20                  25                  30

Gln Cys Lys Ile Thr Val Cys His Cys Arg Arg
        35                  40

<210> SEQ ID NO 94
<211> LENGTH: 32
<212> TYPE: PRT
<213> ORGANISM: Rattus norvegicus

<400> SEQUENCE: 94

Val Thr Cys Tyr Cys Arg Ser Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 95
<211> LENGTH: 31
<212> TYPE: PRT
<213> ORGANISM: Rattus norvegicus

<400> SEQUENCE: 95

Val Thr Cys Ser Cys Arg Thr Ser Ser Cys Arg Phe Gly Glu Arg Leu
1               5                   10                  15

Ser Gly Ala Cys Arg Leu Asn Gly Arg Ile Tyr Arg Leu Cys Cys
            20                  25                  30

<210> SEQ ID NO 96
<211> LENGTH: 34
<212> TYPE: PRT
<213> ORGANISM: Oryctolagus cuniculus

<400> SEQUENCE: 96

Gly Ile Cys Ala Cys Arg Arg Arg Phe Cys Leu Asn Phe Glu Gln Phe
1               5                   10                  15

Ser Gly Tyr Cys Arg Val Asn Gly Ala Arg Tyr Val Arg Cys Cys Ser
            20                  25                  30

Arg Arg

<210> SEQ ID NO 97
<211> LENGTH: 64
<212> TYPE: PRT
<213> ORGANISM: Pan troglodytes

<400> SEQUENCE: 97

Met Arg Val Leu Tyr Leu Leu Phe Ser Phe Leu Phe Ile Phe Leu Met
1               5                   10                  15

Pro Leu Pro Gly Val Phe Gly Gly Ile Ser Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60

<210> SEQ ID NO 98
<211> LENGTH: 64

```
<212> TYPE: PRT
<213> ORGANISM: Capra hircus

<400> SEQUENCE: 98

Met Arg Leu His His Leu Leu Leu Val Leu Phe Phe Leu Val Leu Ser
1               5                   10                  15

Ala Gly Ser Gly Phe Thr Gln Gly Ile Arg Ser Arg Ser Cys His
            20                  25                  30

Arg Asn Lys Gly Val Cys Ala Leu Thr Arg Cys Pro Arg Asn Met Arg
        35                  40                  45

Gln Ile Gly Thr Cys Phe Gly Pro Pro Val Lys Cys Cys Arg Lys Lys
    50                  55                  60

<210> SEQ ID NO 99
<211> LENGTH: 64
<212> TYPE: PRT
<213> ORGANISM: Capra hircus

<400> SEQUENCE: 99

Met Arg Leu His His Leu Leu Leu Ala Leu Phe Phe Leu Val Leu Ser
1               5                   10                  15

Ala Gly Ser Gly Phe Thr Gln Gly Ile Ile Asn His Arg Ser Cys Tyr
            20                  25                  30

Arg Asn Lys Gly Val Cys Ala Pro Ala Arg Cys Pro Arg Asn Met Arg
        35                  40                  45

Gln Ile Gly Thr Cys His Gly Pro Pro Val Lys Cys Cys Arg Lys Lys
    50                  55                  60

<210> SEQ ID NO 100
<211> LENGTH: 96
<212> TYPE: PRT
<213> ORGANISM: Macaca mulatta

<400> SEQUENCE: 100

Met Arg Thr Leu Val Ile Leu Ala Ala Ile Leu Leu Val Ala Leu Gln
1               5                   10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Val Ser Leu Ala
        35                  40                  45

Trp Asp Glu Ser Leu Ala Pro Lys Asp Ser Val Pro Gly Leu Arg Lys
    50                  55                  60

Asn Met Ala Cys Tyr Cys Arg Ile Pro Ala Cys Leu Ala Gly Glu Arg
65                  70                  75                  80

Arg Tyr Gly Thr Cys Phe Tyr Arg Arg Arg Val Trp Ala Phe Cys Cys
                85                  90                  95

<210> SEQ ID NO 101
<211> LENGTH: 96
<212> TYPE: PRT
<213> ORGANISM: Macaca mulatta

<400> SEQUENCE: 101

Met Arg Thr Leu Val Ile Leu Ala Ala Ile Leu Leu Val Ala Leu Gln
1               5                   10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Val Ser Leu Ala
        35                  40                  45
```

Trp Asp Glu Ser Leu Ala Pro Lys Asp Ser Val Pro Gly Leu Arg Lys
         50                  55                  60

Asn Met Ala Cys Tyr Cys Arg Ile Pro Ala Cys Leu Ala Gly Glu Arg
 65                  70                  75                  80

Arg Tyr Gly Thr Cys Phe Tyr Leu Gly Arg Val Trp Ala Phe Cys Cys
                 85                  90                  95

<210> SEQ ID NO 102
<211> LENGTH: 33
<212> TYPE: PRT
<213> ORGANISM: Mesocricetus auratus

<400> SEQUENCE: 102

Val Thr Cys Phe Cys Arg Arg Arg Gly Cys Ala Ser Arg Glu Arg His
 1               5                  10                  15

Ile Gly Tyr Cys Arg Phe Gly Asn Thr Ile Tyr Arg Leu Cys Cys Arg
                 20                  25                  30

Arg

<210> SEQ ID NO 103
<211> LENGTH: 31
<212> TYPE: PRT
<213> ORGANISM: Mesocricetus auratus

<400> SEQUENCE: 103

Cys Phe Cys Lys Arg Pro Val Cys Asp Ser Gly Glu Thr Gln Ile Gly
 1               5                  10                  15

Tyr Cys Arg Leu Gly Asn Thr Phe Tyr Arg Leu Cys Cys Arg Gln
                 20                  25                  30

<210> SEQ ID NO 104
<211> LENGTH: 39
<212> TYPE: PRT
<213> ORGANISM: Gallus gallus

<400> SEQUENCE: 104

Gly Arg Lys Ser Asp Cys Phe Arg Lys Asn Gly Phe Cys Ala Phe Leu
 1               5                  10                  15

Lys Cys Pro Tyr Leu Thr Leu Ile Ser Gly Lys Cys Ser Arg Phe His
                 20                  25                  30

Leu Cys Cys Lys Arg Ile Trp
             35

<210> SEQ ID NO 105
<211> LENGTH: 43
<212> TYPE: PRT
<213> ORGANISM: Allomyrina dichotoma

<400> SEQUENCE: 105

Val Thr Cys Asp Leu Leu Ser Phe Glu Ala Lys Gly Phe Ala Ala Asn
 1               5                  10                  15

His Ser Leu Cys Ala Ala His Cys Leu Ala Ile Gly Arg Arg Gly Gly
                 20                  25                  30

Ser Cys Glu Arg Gly Val Cys Ile Cys Arg Arg
             35                  40

<210> SEQ ID NO 106
<211> LENGTH: 31
<212> TYPE: PRT
<213> ORGANISM: Cavia porcellus

<400> SEQUENCE: 106

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30

<210> SEQ ID NO 107
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: This residue represents a nonconsecutive
      substituted amino acid which may be present or absent.
<220> FEATURE:
<221> NAME/KEY: MISC_FEATURE
<222> LOCATION: (3)..(3)
<223> OTHER INFORMATION: This residue represents a consecutive
      substituted amino acid which may be present or absent.
<220> FEATURE:
<221> NAME/KEY: MISC_FEATURE
<222> LOCATION: (6)..(6)
<223> OTHER INFORMATION: This residue represents two consecutive
      substituted amino acids which may be present or absent.
<220> FEATURE:
<221> NAME/KEY: MISC_FEATURE
<222> LOCATION: (8)..(8)
<223> OTHER INFORMATION: This residue represents three consecutive
      substituted amino acids which may be present or absent.
<220> FEATURE:
<221> NAME/KEY: MISC_FEATURE
<222> LOCATION: (11)..(11)
<223> OTHER INFORMATION: This residue represents four consecutive
      substituted amino acids which may be present or absent.
<220> FEATURE:
<221> NAME/KEY: MISC_FEATURE
<222> LOCATION: (13)..(13)
<223> OTHER INFORMATION: This residue represents five consecutive
      substituted amino acids which may be present or absent.
<220> FEATURE:
<221> NAME/KEY: MISC_FEATURE
<222> LOCATION: (15)..(15)
<223> OTHER INFORMATION: This residue represents six consecutive
      substituted amino acids which may be present or absent.
<220> FEATURE:
<221> NAME/KEY: MISC_FEATURE
<222> LOCATION: (18)..(18)
<223> OTHER INFORMATION: This residue represents two nonconsecutive
      substituted amino acids which may be present or absent.

<400> SEQUENCE: 107

Xaa Cys Asn Cys Arg Asn Cys Asn Glu Arg Asn Cys Asn Gly Asn Cys
1               5                   10                  15

Cys Xaa

<210> SEQ ID NO 108
<211> LENGTH: 27
<212> TYPE: DNA
<213> ORGANISM: Artificial Sequence
<220> FEATURE:
<223> OTHER INFORMATION: Synthetic

<400> SEQUENCE: 108
cttgcacttg tcacaaacag tgcacct                                            27

<210> SEQ ID NO 109
<211> LENGTH: 26
<212> TYPE: DNA
<213> ORGANISM: Artificial Sequence
<220> FEATURE:

<223> OTHER INFORMATION: Synthetic

<400> SEQUENCE: 109
gcggccgcat gtggaaatgg atactg    26

<210> SEQ ID NO 110
<211> LENGTH: 28
<212> TYPE: DNA
<213> ORGANISM: Artificial Sequence
<220> FEATURE:
<223> OTHER INFORMATION: Synthetic

<400> SEQUENCE: 110
gtcgacctat gagtgtacca ccattgga    28

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115
<211> LENGTH: 35
<212> TYPE: DNA
<213> ORGANISM: Artificial Sequence
<220> FEATURE:
<223> OTHER INFORMATION: Synthetic

<400> SEQUENCE: 115
gcagagtcag aggcgcccgg tgtgctgtgc tcagc    35

<210> SEQ ID NO 116
<211> LENGTH: 40
<212> TYPE: DNA
<213> ORGANISM: Artificial Sequence
<220> FEATURE:
<223> OTHER INFORMATION: Synthetic

<400> SEQUENCE: 116
cctcctttgg aagggcgctg agcacagcag cccggccgcc    40

<210> SEQ ID NO 117
<211> LENGTH: 46
<212> TYPE: DNA
<213> ORGANISM: Artificial Sequence
<220> FEATURE:
<223> OTHER INFORMATION: Synthetic

<400> SEQUENCE: 117

```
ctttcttcgg gcggcttttc ggccacgcgt cgaggccttg ccgatc                    46
```

<210> SEQ ID NO 118
<211> LENGTH: 67
<212> TYPE: PRT
<213> ORGANISM: Artificial Sequence
<220> FEATURE:
<223> OTHER INFORMATION: Synthetic

<400> SEQUENCE: 118

```
Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Ala Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65
```

<210> SEQ ID NO 119
<211> LENGTH: 67
<212> TYPE: PRT
<213> ORGANISM: Artificial Sequence
<220> FEATURE:
<223> OTHER INFORMATION: Synthetic

<400> SEQUENCE: 119

```
Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Ala Ala Val Leu Ser Ala Leu Pro Lys
        35                  40                  45

Glu Glu Gln Ile Gly Lys Ala Ser Thr Arg Gly Arg Lys Ala Ala Arg
    50                  55                  60

Arg Lys Lys
65
```

<210> SEQ ID NO 120
<211> LENGTH: 2346
<212> TYPE: DNA
<213> ORGANISM: Artificial Sequence
<220> FEATURE:
<223> OTHER INFORMATION: Synthetic

<400> SEQUENCE: 120

```
aagcttatat tccatgctag ggttctggtg ttggtgcgtg gggttggggt gggactgcag      60
aattcgccct taagattata ttccatgcta gggttctggt gttggtgcgt ggggttgggg    120
tgggactgca gaagtgcctt ttaagattat gtgattgact gatctgtcat tggttccctg    180
ccatctttat cttttggatt ccctcggag gaggggagg aaggagtttc ttttgggttt     240
tattgaatga aatgaaaggg aaagtagagc tgttcctatg tcccgggctc cggagcttct    300
attcctgatc cctgcataag aaggagacat ggtggtggtg gtggtgggtg gggtggtgg    360 ggcacagagg aagccggtac tgggctctgc accccattcc cgctcccaga tccctctgga    420
cacagcattt ttctccagtg agcacagcct cccttgccc cacagccaac agcaacatgc     480
ctcccaacaa aagcatctgt ccctcagcca aaaccctgt tgcctctctc tggggaaatt    540
```

```
gtagggctgg gccagggtgg ggggaccatt ctctgcaggg agattaggag tgtctgtcag      600
gggcgggtgg agcggggtgg ggccctggct tactcacatc cttgagagtc ctttgctggc      660
agatttgggg agcccacagc tcagatgtct gtctcagcat tgtcttccaa gctcctaggc      720
cacagtagtg gggggctccc ttctctggct tcttctttgg tgacagtcaa ggtgggttg       780 ggggtgacag agggtcctgc ttctgtacta ggagcagttg atcccaggaa gagcatcgga      840
gcctccagca ggggctgttg gggctgtct gaggagatag gatgcgtcag gcagcccag        900 acacgttcac attcctctca acatgcctgc cggggtctgt ggagcctagg ggctgatggg      960
agggtggggt gggggccgga agggtttgct tcgggaggtt gtctgggaga ttgctgaagt     1020
tttgatatac acacctccaa agcaggacca agtggactcc tagaaatgtc ccctgaccct     1080
tggggcttca ggagtcaggg accctcgtgt ccacctcacc ttgcccttgg cacagcccag     1140
ctccactcca gcctctactc ctccccagaa catctcctgg gccagttcca aaggggctc      1200 aaacgagggc gcctgagctg ccacactagg gatgttctgg gggtctgaga agatatctgg     1260
ggctggaaga ataaaaggcc ccctaggcct gttcctggat gcagctccag ccactttggg    1320
gctaagcctg ggctataaca atgccaacga ggcttcttgc catactcggt ttacaaaacc     1380 cttttcacata cattgtcgca ttggattctc agagctgact gcactaagca gaatagatgg     1440
tatgactccc actttgcaga tgagaacact gaggctcaga gaagtgccaa gccctgggtc     1500
acagaggcgt aaatggcaga gccaggaccc acctgactcc aggctggttc ctggcctcca     1560
tgaggccacc tgccctatgg tgtggttgat gtgagatcct caccataggg aggagattag     1620
ggtctgtgct cagggatggg gagggcttgc tggatttctc tttgatgggg atgttggggt     1680
gggaatcacg atacacctga ctagctgggt gtatttcagg gatgggacag acttctcagc     1740
acagcatggg aggtcaggcc tgggagggcc ccccagacct ccttgtctct aatagagggt     1800
catggtgagg gaggcctgtc tgtgcccaag gtgaccttgc catgccggtg ctttccagcc     1860
gggtatccat cccctgcagc agcaggcttc ctctacgtgg atgttaaagg cccattcagt     1920
tcatggagag ctagcaggta actaggttta aggtgcagag gccctgctct ctgtcaccct     1980
ggctaagccc agtgcgcggg ttcctgaggg ctgggactcc cagggtccga tgggaaagtg     2040
tagcctgcag gcccacacct ccccctgtga atcacgcctg cgggacaag gaagcccaaa      2100 acactccaaa caatgagttt ccagtaaaat atgcacagac tgatgaggcg gatgagagga     2160
gggacctggc tgggagttgg cgctagcctg tgggtgatga aagccaaggg gaatggaaag     2220
tgccagaccc gcccctacc cacgagtata aagcactcgc atccctttcc aatttacccg      2280
agcaccttct cttcactcag ccaactgctc gctcgctcac ctccctcctc tgcaccaadg     2340
gcgaat                                                                2346
```

<210> SEQ ID NO 121
<211> LENGTH: 67
<212> TYPE: PRT
<213> ORGANISM: Homo sapiens

<400> SEQUENCE: 121

Met Arg Thr Ser Tyr Leu Leu Leu Phe Thr Leu Cys Leu Leu Leu Ser
1               5                   10                  15

Glu Met Ala Ser Gly Asn Phe Leu Thr Gly Leu Gly His Arg Ser Asp
            20                  25                  30

His Tyr Asn Cys Val Ser Ser Gly Gly Gln Cys Leu Tyr Ser Ala Cys
        35                  40                  45

Pro Ile Phe Thr Lys Ile Gln Gly Thr Cys Tyr Arg Gly Lys Ala Lys

```
                    50                  55                  60
Cys Cys Lys
 65

<210> SEQ ID NO 122
<211> LENGTH: 65
<212> TYPE: PRT
<213> ORGANISM: Homo sapiens

<400> SEQUENCE: 122

Met Arg Val Leu Tyr Leu Leu Phe Ser Phe Leu Phe Ile Phe Leu Met
 1               5                  10                  15

Pro Leu Pro Gly Gly Val Phe Gly Gly Ile Gly Asp Pro Val Thr Cys
                20                  25                  30

Leu Lys Ser Gly Ala Ile Cys His Pro Val Phe Cys Pro Arg Arg Tyr
            35                  40                  45

Lys Gln Ile Gly Thr Cys Gly Leu Pro Gly Thr Lys Cys Cys Lys Lys
        50                  55                  60

Pro
 65

<210> SEQ ID NO 123
<211> LENGTH: 67
<212> TYPE: PRT
<213> ORGANISM: Homo sapiens

<400> SEQUENCE: 123

Met Arg Ile His Tyr Leu Leu Phe Ala Leu Leu Phe Leu Phe Leu Val
 1               5                  10                  15

Pro Val Pro Gly His Gly Gly Ile Ile Asn Thr Leu Gln Lys Tyr Tyr
                20                  25                  30

Cys Arg Val Arg Gly Gly Arg Cys Ala Val Leu Ser Cys Leu Pro Lys
            35                  40                  45

Glu Glu Gln Ile Gly Lys Cys Ser Thr Arg Gly Arg Lys Cys Cys Arg
        50                  55                  60

Arg Lys Lys
 65

<210> SEQ ID NO 124
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(21)
<223> OTHER INFORMATION: The residues at these positions may be present
      or absent.

<400> SEQUENCE: 124

Lys Leu Ala Lys Lys Leu Ala Lys Leu Ala Lys Lys Leu Ala Lys Leu
 1               5                  10                  15

Ala Lys Lys Leu Ala
            20

<210> SEQ ID NO 125
<211> LENGTH: 21
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (8)..(21)
<223> OTHER INFORMATION: The residues at these positions may be present
      or absent.

<400> SEQUENCE: 125

Lys Leu Ala Lys Leu Ala Lys Lys Leu Ala Lys Leu Ala Lys Lys Leu
1               5                   10                  15

Ala Lys Leu Ala Lys
            20

<210> SEQ ID NO 126
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(21)
<223> OTHER INFORMATION: The residues at these positions may be present
      or absent.

<400> SEQUENCE: 126

Lys Ala Leu Lys Ala Leu Lys Lys Ala Leu Lys Ala Leu Lys Lys Ala
1               5                   10                  15

Leu Lys Ala Leu Lys
            20

<210> SEQ ID NO 127
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(21)
<223> OTHER INFORMATION: The residues at these positions may be present
      or absent.

<400> SEQUENCE: 127

Lys Leu Gly Lys Lys Leu Gly Lys Leu Gly Lys Lys Leu Gly Lys Leu
1               5                   10                  15

Gly Lys Lys Leu Gly
            20

<210> SEQ ID NO 128
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(21)
<223> OTHER INFORMATION: The residues at these positions may be present
      or absent.

<400> SEQUENCE: 128

Lys Ala Ala Lys Lys Ala Ala Lys Ala Ala Lys Lys Ala Ala Lys Ala
1               5                   10                  15

Ala Lys Lys Ala Ala
            20
```